United States Patent [19]
Benderev et al.

[11] Patent Number: 6,001,104
[45] Date of Patent: *Dec. 14, 1999

[54] BONE ANCHOR IMPLANTATION DEVICE

[75] Inventors: Theodore V. Benderev, San Juan Capistrano; Neil H. Naves; Mark J. Legome, both of Mission Viejo, all of Calif.

[73] Assignee: Boston Scientific Technology, Inc., Maple Grove, Minn.

[ * ] Notice: This patent is subject to a terminal disclaimer.

[21] Appl. No.: 08/803,060

[22] Filed: Feb. 20, 1997

Related U.S. Application Data

[63] Continuation of application No. 08/345,003, Nov. 23, 1994, Pat. No. 5,749,884, which is a continuation of application No. 07/862,847, Apr. 3, 1992, abandoned, which is a continuation-in-part of application No. 07/801,747, Dec. 3, 1991, abandoned.

[51] Int. Cl.[6] .................................................. A61B 17/00
[52] U.S. Cl. .............................................. 606/80; 606/96
[58] Field of Search ................................ 606/1, 79, 80, 606/96, 98, 167, 170, 172

[56] References Cited

U.S. PATENT DOCUMENTS

| 1,030,530 | 6/1912 | Palmer . |
| 2,200,120 | 5/1940 | Nauth . |

(List continued on next page.)

FOREIGN PATENT DOCUMENTS

| 389 044 | 3/1989 | Austria . |
| 0 059 044 A3 | 9/1982 | European Pat. Off. . |
| 0 153 831 A3 | 9/1985 | European Pat. Off. . |
| 0 241 240 A2 | 10/1987 | European Pat. Off. . |
| 0 281 763 A2 | 9/1988 | European Pat. Off. . |
| 0 440 991 A1 | 8/1991 | European Pat. Off. . |
| 0 558 993 A2 | 9/1993 | European Pat. Off. . |
| 2 552 655 A1 | 4/1985 | France . |
| 28 30 566 A1 | 1/1980 | Germany . |
| 29 01 962 A1 | 7/1980 | Germany . |
| 34 12 362 C1 | 10/1985 | Germany . |
| 1090377 | 5/1984 | U.S.S.R. . |
| 1 448 111 | 1/1973 | United Kingdom . |
| 2 069 846 | 9/1981 | United Kingdom . |
| 2 252 732 | 8/1992 | United Kingdom . |
| WO 92/00773 | 1/1992 | WIPO . |
| WO 93/10715 | 6/1993 | WIPO . |

OTHER PUBLICATIONS

T.V. Benderev, "Anchor Fixation and Other Modifications of Endoscopic Bladder Neck Suspension," *Urology* 40(5):409–418 (1992).

T.V. Benderev, "A Modified Percutaneous Outpatient Bladder Neck Suspension System," *The Journal of Urology* 152:2316–2320 (1994).

R.F. Gittes, et al., "No–Incision Pubovaginal Suspension for Stress Incontinence," *The Journal of Urology* 138:568–570 (1987).

R. Hancock, et al., "Transpubic Suspension of the Bladder Neck for Urinary Incontinence," *The Journal of Urology* 123:667–668 (1980).

(List continued on next page.)

*Primary Examiner*—William Lewis
*Attorney, Agent, or Firm*—Testa, Hurwitz & Thibeault, LLP

[57] ABSTRACT

The surgical treatment of stress urinary incontinence is disclosed. The disclosed methods include: 1) a technique of probe passage to avoid injuring the bladder and to provide a more accurate and reproducible capture of the pubocervical fascia lateral to the bladder neck and urethra, 2) anchor fixation of the suspending sutures to the pubic bone to decrease the risk of suture pull through from above and to decrease post-operative pain and 3) a simple and reproducible technique to set a limited tension of the suspending sutures. A description of these methods and results of procedures with some of these methods are disclosed. Novel drill guides, suture passers, suture tensioners, and various related tools and devices for use in the surgical method are also disclosed.

23 Claims, 35 Drawing Sheets

U.S. PATENT DOCUMENTS

| | | |
|---|---|---|
| 2,400,251 | 5/1946 | Nagel . |
| 2,454,680 | 11/1948 | Stephens . |
| 2,666,430 | 1/1954 | Gispert . |
| 2,707,783 | 5/1955 | Sullivan . |
| 3,835,849 | 9/1974 | McGuire . |
| 3,842,825 | 10/1974 | Wagner . |
| 3,892,232 | 7/1975 | Neufeld . |
| 3,995,619 | 12/1976 | Glatzer . |
| 4,172,458 | 10/1979 | Pereyra . |
| 4,257,411 | 3/1981 | Cho . |
| 4,323,057 | 4/1982 | Jamieson . |
| 4,325,373 | 4/1982 | Slivenko et al. . |
| 4,383,527 | 5/1983 | Asnis et al. . |
| 4,421,112 | 12/1983 | Mains et al. . |
| 4,527,726 | 7/1985 | Assell et al. . |
| 4,535,768 | 8/1985 | Hourahane et al. . |
| 4,545,374 | 10/1985 | Jacobson . |
| 4,672,957 | 6/1987 | Hourahane . |
| 4,686,972 | 8/1987 | Kurland . |
| 4,708,139 | 11/1987 | Dunbar, IV . |
| 4,713,077 | 12/1987 | Small . |
| 4,722,331 | 2/1988 | Fox . |
| 4,739,751 | 4/1988 | Sapega et al. . |
| 4,744,353 | 5/1988 | McFarland . |
| 4,784,126 | 11/1988 | Hourahane . |
| 4,788,970 | 12/1988 | Kara et al. . |
| 4,872,451 | 10/1989 | Moore et al. . |
| 4,883,048 | 11/1989 | Purnell et al. . |
| 4,899,743 | 2/1990 | Nicholson et al. . |
| 4,901,711 | 2/1990 | Goble et al. . |
| 4,911,153 | 3/1990 | Border . |
| 4,920,958 | 5/1990 | Walt et al. . |
| 4,940,467 | 7/1990 | Tronzo . |
| 4,945,904 | 8/1990 | Bolton et al. . |
| 4,960,420 | 10/1990 | Goble et al. . |
| 4,978,351 | 12/1990 | Rozas . |
| 4,985,032 | 1/1991 | Goble . |
| 4,997,434 | 3/1991 | Seedhom et al. . |
| 5,026,376 | 6/1991 | Greenberg . |
| 5,027,793 | 7/1991 | Engelhardt et al. . |
| 5,030,219 | 7/1991 | Matsen, III et al. . |
| 5,108,397 | 4/1992 | White . |
| 5,112,337 | 5/1992 | Paulos et al. . |
| 5,116,338 | 5/1992 | Poggie et al. . |
| 5,141,513 | 8/1992 | Fortune et al. . |
| 5,149,329 | 9/1992 | Richardson . |
| 5,163,940 | 11/1992 | Bourque . |
| 5,203,784 | 4/1993 | Ross et al. . |
| 5,207,679 | 5/1993 | Li . |
| 5,207,753 | 5/1993 | Badrinath . |
| 5,217,486 | 6/1993 | Rice et al. . |
| 5,256,133 | 10/1993 | Spitz . |
| 5,258,016 | 11/1993 | DiPoto et al. . |
| 5,268,001 | 12/1993 | Nicholson et al. . |
| 5,582,188 | 12/1996 | Benderev et al. . |
| 5,611,515 | 3/1997 | Benderev et al. . |
| 5,620,012 | 4/1997 | Benderev et al. . |

OTHER PUBLICATIONS

S.R. Kovac, et al., "Instruments & Methods Pubic Bone Suburethral Stabilization Sling for Recurrent Urinary Incontinence," *Obstetrics & Gynecology* 89:624–627 (1997).

G.E. Leach, "Bone Fixation Technique for Transvaginal Needle Suspension," *Urology* XXXI(5):388–390 (1988).

V.C. Mascio, "Therapy of Urinary Stress Incontinence in Women Using Mitek GII Anchors," Mitek Surgical Products, Inc. (1993).

S.A. Scheuer, Videotape: "Mitek Modified Pereyra BNS" (1993).

C.C. Winter, "Peripubic Urethropexy for Urinary Stress Incontinence in Women," *Urology* XX(4):408–411 (1982).

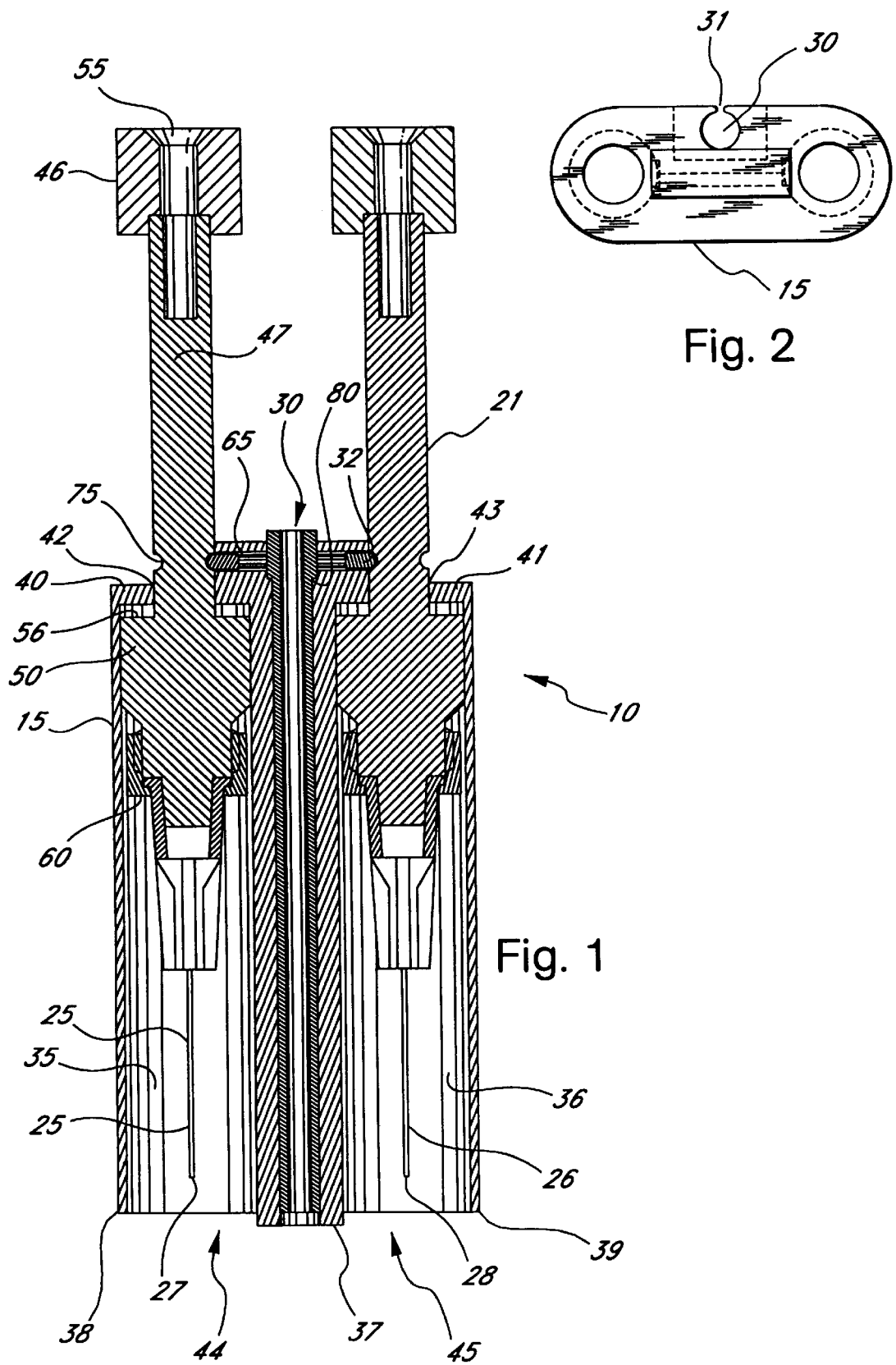

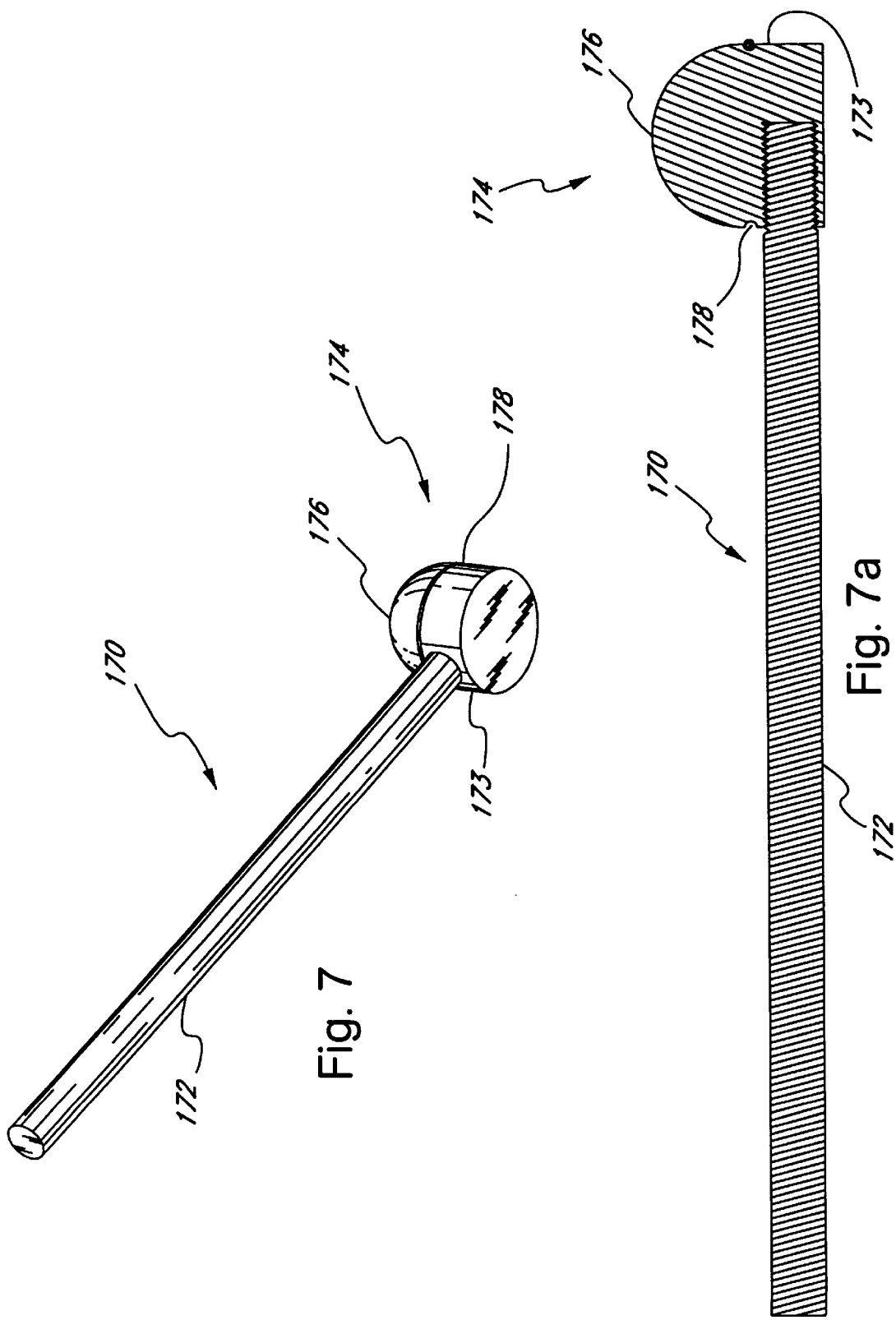

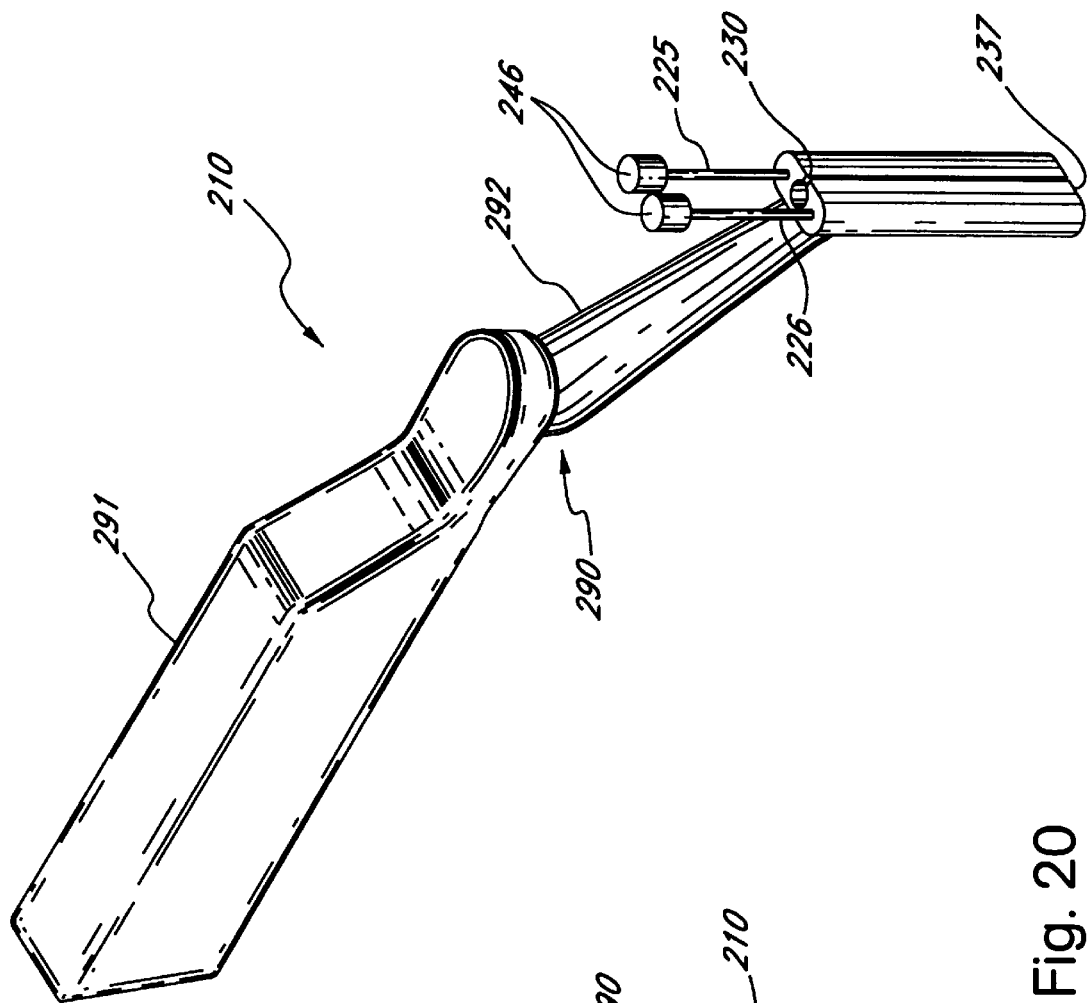
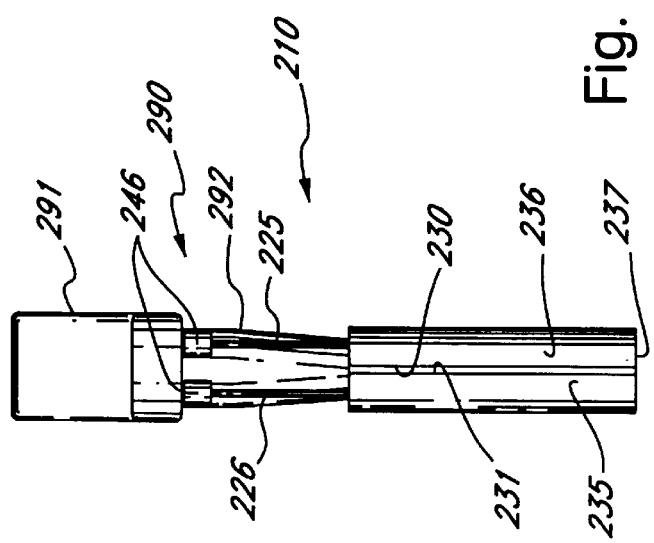
Fig. 19
Fig. 20

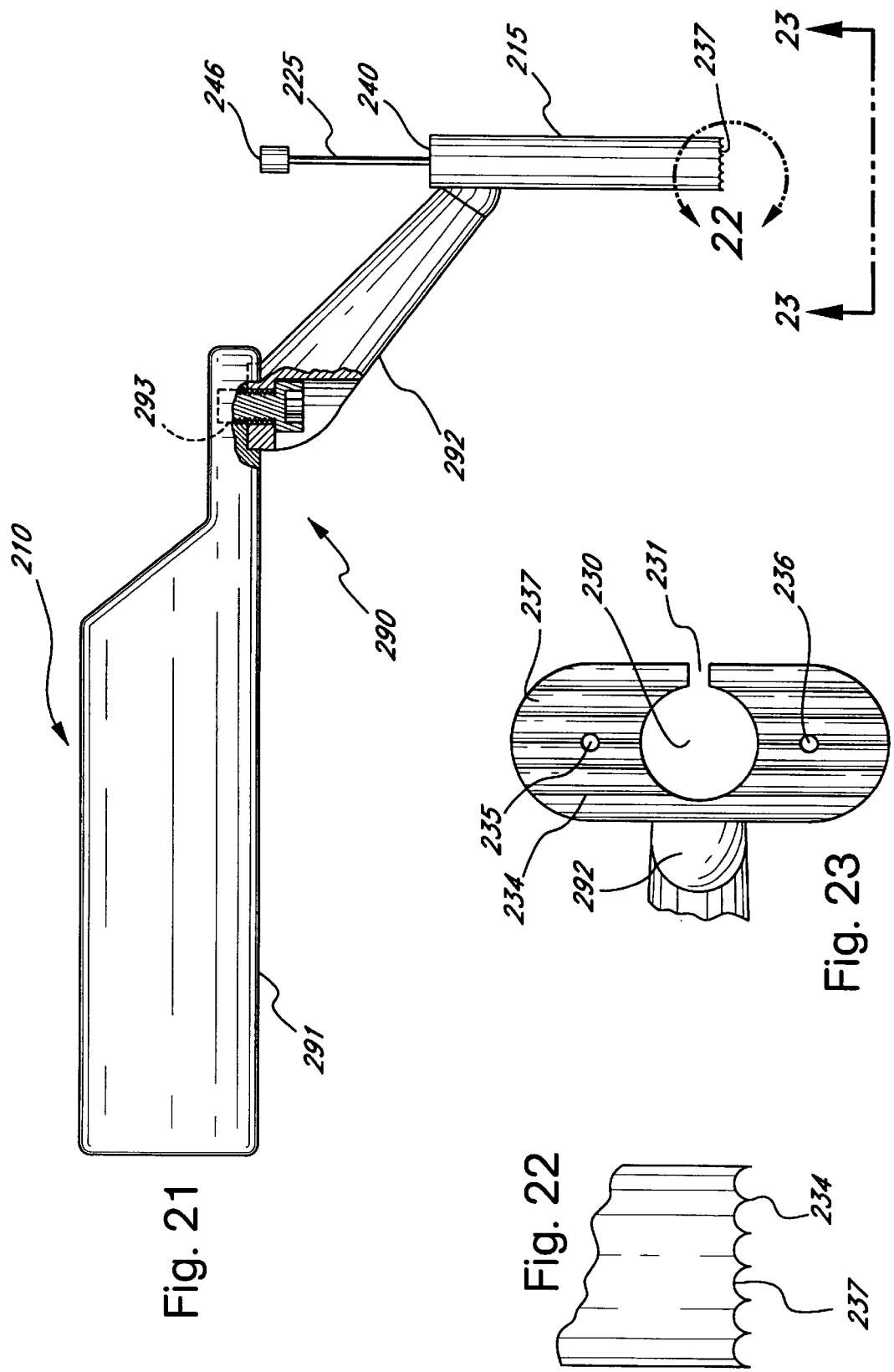

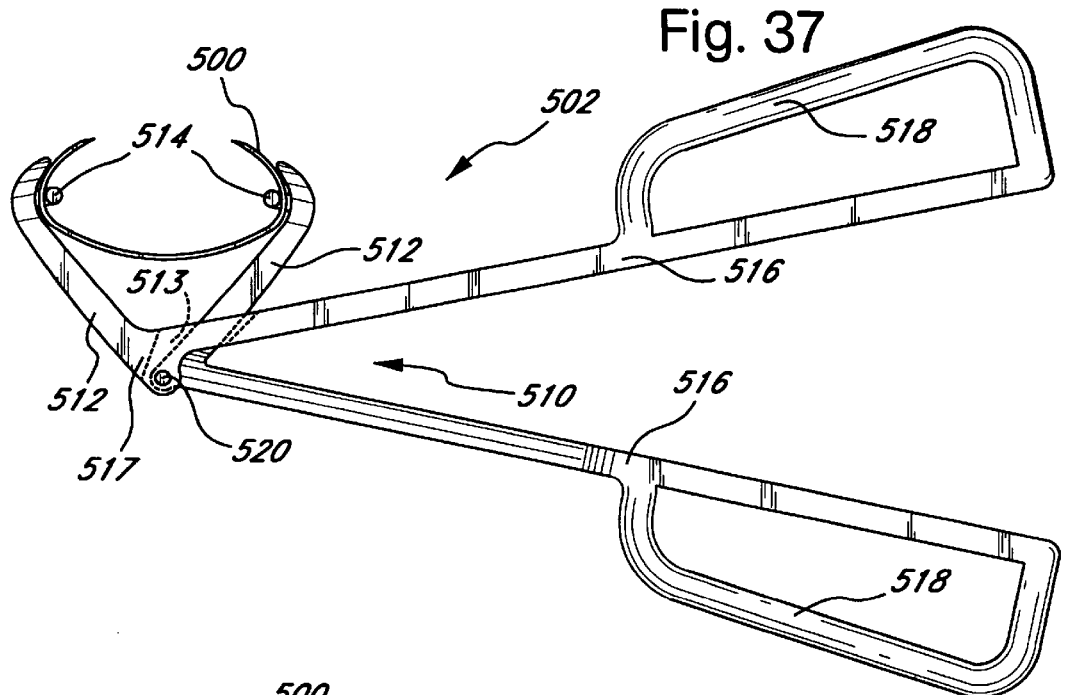
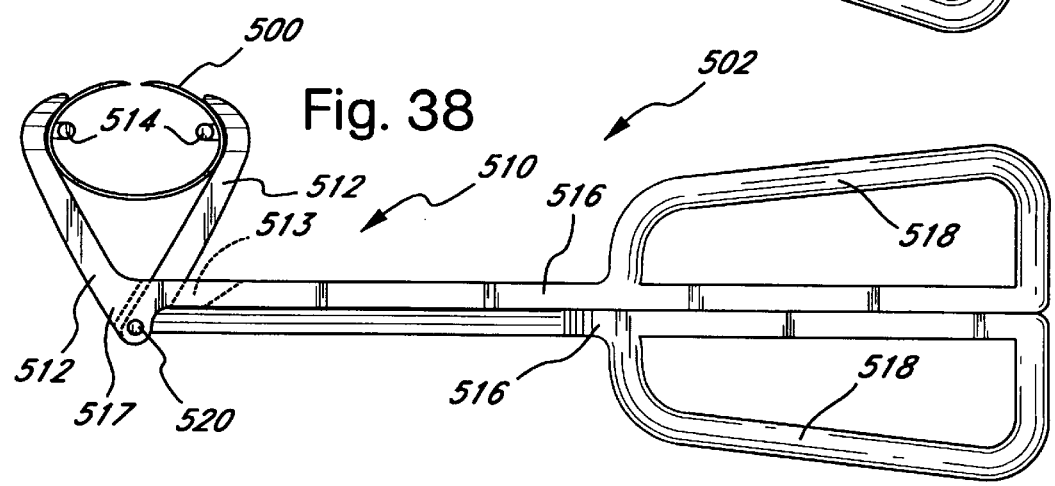
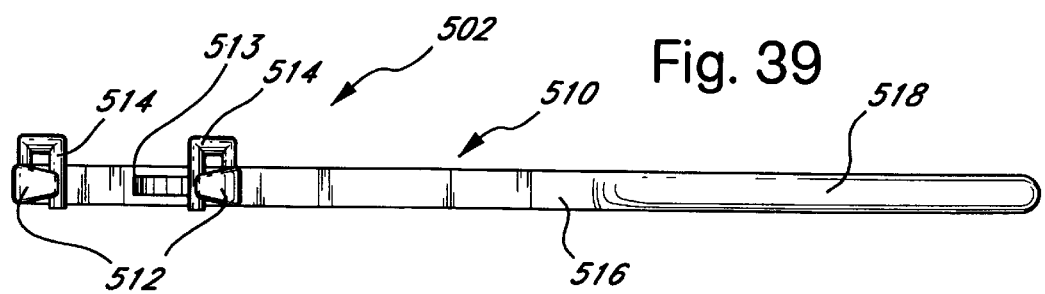

BONE ANCHOR IMPLANTATION DEVICE

This application is a continuation of U.S. patent application Ser. No. 08/345,003, filed Nov. 23, 1994, now U.S. Pat. No. 5,749,884 which is a continuation of U.S. patent application Ser. No. 08,862,847, filed Apr. 3, 1992, now abandoned; which is a continuation-in-part of application Ser. No. 07/801,747, filed Dec. 3, 1991, now abandoned.

BACKGROUND OF THE INVENTION

The present invention relates to the treatment of stress urinary incontinence "SUI," and, in particular, to improved methods and surgical devices for the surgical treatment of SUI in females. The devices disclosed herein are additionally useful in a wide variety of other surgical procedures.

Genuine stress incontinence is the involuntary loss of urine due to a sudden rise in intra-abdominal pressure. It has been estimated that between 40% and 50% of young, healthy nulliparous women admit to occasional mild stress incontinence; however, at least 80% of stress incontinence patients are in the perimenopausal age group and are multiparous. Raz[3] has suggested that the female urethral continence mechanism is dependent on the interaction of four urethral factor: urethral closing pressure, urethral length, urethrotrigonal anatomy, and urethral reception of intra-abdominal pressure.

The urethral closing pressure is predominantly a result of the interaction of smooth and striated muscle sphincter activity, but there is also some contribution by nonmuscular urethral factors such as the submucosal vascular plexus, the elastin and collagen content of the urethral tissues, and a sphincter like effect of the mucosa. There has been considerable diversity of opinion regarding the anatomic structure and the innervation of the urethral sphincters, and a variety of views have been expressed in the literature.

Lapides and associates have stressed the importance of urethral length in the maintenance of continence in the female. However, although it certainly interacts with other factors to contribute to continence, a short urethra alone will not produce incontinence. Urethral length varies considerably in normal women, and women with proven genuine stress urinary incontinence do not invariably have urethral shortening.

Urethrotrigonal anatomy, which can be demonstrated by lateral cystourethrography, should fulfill certain criteria. The bladder base should lie above the level of the inferior ramus of the symphysis, and with straining should not descend more than 1.5 cm. There should be a normal urethrotrigonal alignment with an angle normally less than 100 degrees, and the urethral axis should be approximately 35 degrees from the vertical. In the hypermobile situation loss of all of the normal anatomic features may occur, a radiologic finding that correlates with the clinical finding of cystourethrocele. However, clinical experience has shown that the coexistence of cystourethrocele and incontinence does not predict that the incontinence is of a genuine stress variety.

The transmission of intra-abdominal pressure to the intra-abdominal portion of the proximal urethra is also reported to be important in the maintenance of continence. This is a passive phenomenon, and is the result of the normal anatomic configuration just described. Whenever there is a rise in intra-abdominal pressure during such stresses as coughing or straining, the pressure is transmitted not only to the bladder but also to the proximal urethra, with resultant increase in the closing pressure, and prevention of leakage. If the urethral axis is altered, rotational descent will drop the proximal urethra and bladder base from its intra-abdominal location, and will obviously impair such pressure transmission.

A wide variety of operations have been used to correct this condition, generally involving the principles of elevating the bladder neck anteriorly and/or elongating and narrowing the proximal urethra. Two of the most popular operations today for female stress incontinence are the Marshall-Marchetti-Krantz and Birch vesicourethropexies. The Marshall-Marchetti-Krantz technique has at least an eighty-five percent success rate, against which other operative success rates must be measured. Recently, the Pereyra operation and its modifications have enjoyed some popularity, but less than basic techniques.

Notwithstanding the foregoing, however, there remains a need for an improved treatment for SUI. Preferably, the treatment is as noninvasive as possible under the circumstances, and will eliminate or minimize hospitalization and the use of general anesthetics. In addition, there remains a need for improved medical instrumentation such as drill guides and suture passers for use in connection with SUI treatment and other medical procedures.

SUMMARY OF THE INVENTION

There is provided in accordance with one aspect of the present invention a drill guide for directing a drill bit at a selected site on a bone. The drill guide comprises a housing, and at least two chambers extending axially within the housing. Each of the chambers has an opening at the distal end. A plunger is provided in each of the chambers, each plunger axially movable from a first retracted position to a second extended position. A probe is mounted on the distal end of each of the plungers, and adapted for retraction within the open end of the chamber and extension outside of the open end of the chamber. In a simplified embodiment, each of two or more probes is axially movably disposed within the housing, without the use of a distinct plunger. A drill guide channel extends axially through the housing, within a plane parallel to the plane joining the axes of the first and second chambers, and in between the axes of the first and second chambers.

Preferably, one or both of the plungers is provided with a releasable lock for releasably retaining the plunger in the retracted position, thereby minimizing the likelihood of accidental needle sticks. The preferred probe comprises a hypodermic needle or a sharpened solid wire. In a two probe embodiment, the axes of the first and second probes are separated by a distance within the range from about 5 mm to about 15 mm. Preferably, the axis of the drill guide channel is approximately equidistant from the axes of each of the probes.

In accordance with another aspect of the present invention, there is provided an alternate embodiment of a drill guide for use in locating drill sites in a patient's body. The drill guide comprises a body, a handle connected thereto, and one or more bores extending through said body. Each bore has an opening at a distal end. A probe is provided in each bore, the probe being axially movable from a retracted to an extended position. A drill guide bore, which may also act as one of the probe bores, extends axially through the body. A suture slot extends from outside of the body to the drill guide bore along the length of the body. Serrations are provided on the distal end of the body, aiding in maintaining the opening of a drilled hole. In a two probe embodiment, the axes of the probes are separated by a distance of about 5 to 10 mm. Preferably, the probes of this embodiment are a unitary element, such as a wire or needle. Further, it is desired that the drill guide bore and any probe bores lie in a line perpendicular to the longitudinal axis of the body.

In accordance with the further aspect of the present invention, there is provided a method of positioning a drill guide over a drilling site on bone, comprising the steps of providing a drill guide of the type having a housing, at least two axially extendable probes within the housing, and a drill guide extending through the housing. A first probe is extended from the retracted position to the extended position, and advanced through the tissue until it contacts a bone. The second probe is thereafter extended from the retracted position to the extended position, until the second probe contacts the bone. If the first extension of the second probe does not result in a contact, both probes are retracted within the housing, and the drill guide is translated along the sagittal or other axis. The first probe is thereafter reextended and the foregoing steps are repeated until both the first and second probes contact the bone.

In accordance with another aspect of the present invention, there is provided a method of installing a bone anchor in a bone, utilizing the drill guide defined above. In accordance with the installation method, each of the probes is sequentially extended and advanced through tissue as described until each of said probes is in contact with the bone. A drill bit is thereafter advanced through the drill guide channel and a hole is drilled in the bone. The drill bit is thereafter withdrawn from the drill guide channel, and a suture anchor is advanced through the drill guide shaft and into the bone.

In accordance with another aspect of the present invention, there is provided a suture passer of the type adapted for releasably retaining a suture. The suture passer comprises a handle, and an elongate tubular probe guide extending in a distal direction straight or curved from the handle. An elongate probe is axially movably disposed within the tubular probe guide, for motion between a first retracted position and a second extended position in which the sharpened distal tip of the probe is exposed. An annular recess is provided on the probe, to cooperate with an opening on the tubular guide for receiving a suture. The probe is axially movable with respect to the probe guide between a first position in which the annular recess is aligned with the opening for receiving a suture therein, a second position wherein the annular recess is out of alignment with the opening, to trap or retain a suture therein and a third position in which the distal probe tip is exposed.

In accordance with another aspect of the present invention, there is provided a drape and exposure system comprising a vaginal drape, speculum and buttock plate for isolating the surgical field, providing a mounting surface for surgical instruments, and opening the surgical area for access. The vaginal drape comprises a large section of flexible, sterilizable material. Preferably, the drape has a large abdominal drape connected to a moisture barrier. The drape has a transparent surgical window with an adhesive backing for viewing the surgical area. An opening is provided below the window to allow a gloved hand access through the drape to aid in placement of the drape. A vaginal flap or stretchable moisture-proof fabric is provided in the drape to allow a speculum to be placed therein.

The drape is secured to and about the patient's body by adhesive strips and cable or velcro ties. Further, a plate pocket is provided in the moisture barrier for attachment of the drape to the buttock plate.

The buttock plate is a mainly flat support surface. A mounting arm is provided in one end of the plate, extending upwards about 50 mm and being about 50 mm in width. A bore is provided in the mounting arm to accept a threaded knob for securing various tools to the plate.

The speculum is a member having a support stem with a slot therein to allow mounting to the plate, and a concave engaging member attached to the top of the stem. The concave member is an arcuate shaped member for placement in the vagina. Preferably, the concave member is inserted into the vaginal flap of the drape and then extended into the vagina to aid in isolating the surgical field.

In accordance with yet another aspect of the present invention, there is provided a suture support for providing a structure to which sutures may be anchored inside the body so as to reduce trauma to body tissue. In one form, the suture support comprises a circular plate about 15 mm in diameter and less than about 1 mm in thickness, having a small tab mounted on one side thereof for attachment of a suture. In another form, the support comprises a lattice constructed from wire having a diameter of about 1 mm. In another embodiment the support comprises a hub area with spokes radiating outwardly thereto.

In accordance with another aspect of the present invention there is provided a tissue staple and staple applier for use in suspending tissue in transvaginal bladder suspension procedures.

The tissue staples are arcuate elliptical structures preferably made of spring wire. Sharpened ends are provided on the staple for penetration of tissue. The body of the staple is located in between the ends and may have an enlarged center section in order to aid in distribution of forces on the tissue, and it may have openings to allow ingrowth of tissue.

The staple applier comprises a scissor like body provided with two arms having handles at one end, and a pair of pressing support members at the other end. The arms are about 160 mm long and are rotatably attached to one another by a pin located at the end of the arms opposite the handles.

The pressing members extend upwards from the pinned ends of the arms, mounted generally perpendicular to the longitudinal axis of the applier. The pressing members are arcuate in shape, their inside surface shape mirroring the shape of the staples, and their free tips being sharp to allow tissue penetration. The pressing members are designed such that when the arms of the applier are open, the members are a distance away from one another to allow the introduction of a staple therebetween. When the arms of the applier are pressed together, the members move towards one another to press the sharp ends of the staple closed.

An opposing pair of staple removal prongs are mounted to, and between, the pressing members. The prongs are generally U-shaped shafts extending from the members outwardly and then back in between the members perpendicular to the axis of the applier. The prongs may be advanced towards one another or drawn apart from each other by the movement of the arms.

There is a "C" clamp provided in accordance with another aspect of the present invention. The "C" clamp is an alternative to the drill guide and is designed for use with the buttock plate. The "C" clamp aids in locating a drill bit through the pubic region.

The "C" clamp comprises a support arm, attachment member, and guide arm. The attachment member is a plate having a slot therein to allow passage of a knob therethrough for securing the clamp to the buttock plate. The support arm is a primarily L shaped member extending from the attachment member to a distal end where a drill stop is located. The support arm is shaped so that when used in a bladder neck suspension procedure, in use, it extends from the attachment member located outside the body to its distal end located in the vagina. A bore is provided in the support arm near its connection with the attachment member for acceptance of the guide arm.

The guide arm is shaped like an inverted L, having a shaft-like stem which engages the support arm through the bore. The shaft is threaded and may be locked in relation to the support arm by knobs. The drill guide portion of the guide is a wide block. A drill guide bore and one or more probe bores are located in the drill guide. Probes are provided for engaging the probe bores. The probes and bores are similar to those described in the drill guide. The drill guide bore is oriented such that a line passing along its axis encounters the drill step on the support arm.

In accordance with another aspect of the present invention, there is provided a surgical bladder neck suspension procedure involving use of the tissue staples and drape and exposure system. This method is accomplished entirely transvaginally through a tissue suspension procedure. In accordance with this procedure, the patient is first placed in the lithotomy position and sterily prepared. The vaginal drape is positioned over the abdomen and secured thereto. The buttock plate is inserted into the buttock plate pocket, which lies under the patient and with the guide arm extending upwards between the legs. The speculum is inserted into the vaginal flap and inserted into the vagina. The speculum is secured to the arm of the buttock plate.

A staple is loaded into the applier with the arms of the applier in the open position. The pivot end of the applier is inserted into the vagina. Once aligned to one side of the bladder neck, the staple and support members are pressed into the vaginal mucosa and upwards into the iliopectineal or other ligament. The arms of the applier are pressed together to close the staple. The applier may then be removed and the process repeated in the other side of the bladder neck.

In accordance with another aspect of the present invention, there is provided a bladder neck suspension procedure involving use of the suture supports, anchors, and the "C" clamp or drill guide or suture passer.

In accordance with this procedure, the drape and exposure system are prepared on the patient as before. The suture passer is passed through an incision made over the pubic bone into the vagina. A suture that is attached to a suture support is captured in the suture channel of the passer at the other. The passer is passed back out of the patient, until the suture is pulled slightly taut. The free end of the suture is then affixed to the pubic bone with a knot, plug, or anchor. The anchor may be placed by pressing it into a hole drilled into the bone, as located by the "C" clamp or drill guide.

Alternatively, the drill guide or "C" clamp may be used to position a drill bit for drilling a passageway from the pubic area to the vagina. The free end of the suture is then passed through the drilled hole up from the vagina to the pubic area. The free end of the suture may then be tied off or affixed by a plug or anchor to prevent it from pulling back through.

In accordance with a further aspect of the present invention, there is provided a surgical bladder neck suspension procedure, for the treatment of stress urinary incontinence. In accordance with the method, a technique of creating a suspension web comprising a plurality of lengths of suture is constructed extending between the pubocervical fascia and the pubic bone, on each of the right and left sides of the midline. Sutures are carried through tissue utilizing the suture passer disclosed herein, and sutures are tied down to the pubic bone utilizing a bone anchor positioned on each of the right and left sides of the midline by a drill guide as disclosed herein. Prior to tying, sutures are appropriately tensioned by advancing the suture around the suture tensioner disclosed herein and tying in a conventional manner. Thereafter, the suture tensioner is removed and the surgical site prepared and closed in a conventional manner.

These and additional features and advantages of the present invention will become apparent from the detailed description of preferred embodiments which follows, when taken together with the attached drawings and claims.

BRIEF DESCRIPTION OF THE DRAWINGS

FIG. 1 is an elevational partial cross sectional schematic view of a drill guide in accordance with the present invention.

FIG. 2 is an end view of the drill guide of FIG. 1.

FIG. 7 is a perspective and detailed view of the suture tensioner in accordance with the present invention.

FIG. 7a is a cross sectional side view of the suture tensioner of FIG. 7.

FIG. 19 is a perspective view of an alternate embodiment drill guide of the present invention.

FIG. 20 is a front elevational view of the drill guide of FIG. 19.

FIG. 21 is a side view with a partial cross section of the drill guide of FIG. 19.

FIG. 22 is an enlarged side view of the end of the drill guide of FIG. 21.

FIG. 23 is an enlarged end view of the drill guide of FIG. 21.

FIG. 37 is a side elevational view of the staple applier with a staple before application, in accordance with the present invention.

FIG. 38 is a side elevational view of the staple applier and staple of FIG. 37 in a closed position.

FIG. 39 is a top view of the staple applier of FIG. 38.

DETAILED DESCRIPTION OF PREFERRED EMBODIMENTS

Figure 4:
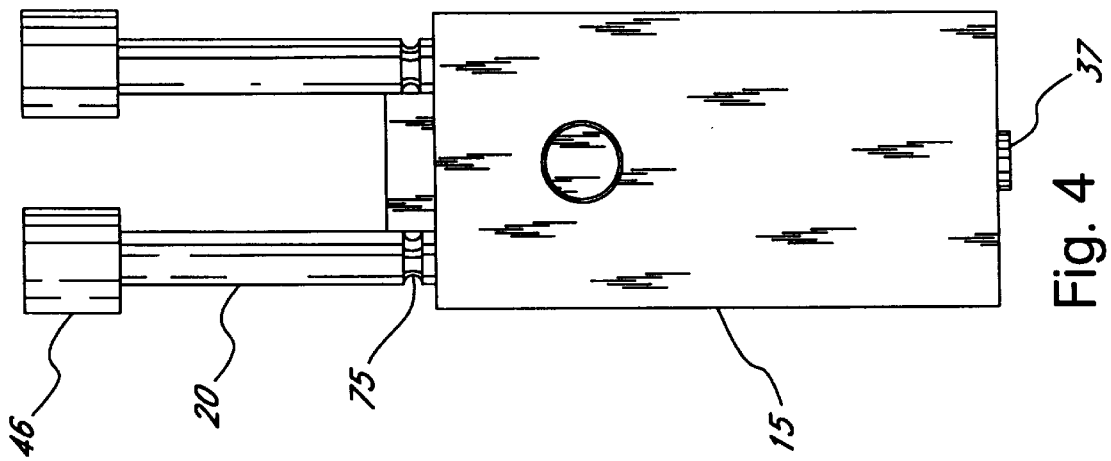
FIG. 4 is a front elevational view of the drill guide shown in FIG. 3.

SUI is generally curable with any of a variety of surgical procedures that properly suspends the bladder neck. However, limitations of known procedures include 1) the extent of surgical morbidity 2) the ever present threat of long term failures and 3) the reproducibility between different surgeons.

Pereyra[1] introduced the transvaginal bladder neck suspension as a less invasive alternative to open retropubic procedures. Stamey[2] limited morbidity and improved the reproducibility of the transvaginal bladder neck suspension by introducing endoscopic control and confirmation of suture placement. Raz[3] has improved reproducibility by introducing full palpatory control of needle passage through the retropubic space, thereby limiting disability through injury to the bladder or other retropubic structures.

The distal passage of the suture passer disclosed herein or other needle followed by a sweep back to the bladder neck area described herein accomplishes a similar goal but without the necessity of entering the retropubic space. Passage of the needle point to the level of the introitus along the underside of the pubic bone obviates the need to turn the needle down toward a bladder neck that has been digitally elevated, thereby reducing the risk of bladder injury. Extraction of the needle from the pubourethral ligament is necessary to allow a "capture" of the more pliable pubocervical fascia alongside the urethra. The subsequent, gentle sweep back of the needle along the surface of the pubocervical fascia provides an easy and safe means of introducing the needle to the bladder neck area under the vaginal digital guidance.

Gittes and Loughlin[5] have further popularized the technique of Pereyra and demonstrated an advantage of increased long-term efficacy by creating an autologous bolster with the transvaginal passage of a curved needle. As an alternative manner of creating an autologous bolster, the proposed modification described herein uses the suture passer disclosed herein, or a Stamey needle through a suprapubic approach to carry the suture through all of its vaginal passes. The full carriage of the suture by the suture passer needle offers the benefits of 1) improving accuracy and reproducibility by allowing palpation of the needle at each vaginal entry point in reference to the bladder neck and catheter, 2) potentially decreasing morbidity by reducing the risk of injury and/or irritation through inadvertent entry into any part of the urethra or bladder and 3) possibly contributing to long term efficacy by assuring that a full thickness layer of pubocervical fascia is captured. This technique permits the capture of a large lateral volume of pubocervical fascia similar in an area to that available for suturing in an open retropubic urethropexy.

Leach[4] has limited morbidity by decreasing post-operative pain and has potentially improved long-term efficacy with pubic fixation of the suspending sutures. However, the trochar needle passage through the pubic bone as described by Leach can be difficult through the limited exposure that is used with some forms of endoscopic bladder neck suspension. Other various forms of pubic bone fixation have also been described with transvaginal and open bladder neck suspension surgery[6,7,8]. To facilitate the anchoring of the suspensory suture to the pubic bone with minimal soft tissue dissection, the present inventor has used a new set of devices called the Mitek Anchor System. The latest generation of Mitek anchor, the G2, consists of a titanium body coupled to nickel-titanium arcs. These anchors have recently been used most commonly for tenodesis and ligamentous reconstruction of the shoulder and foot[9,10].

In the present setting of bladder neck suspensions, the Mitek anchor with attached suture is passed into a hole drilled in the pubic bone. Care must be taken to assure that the hole has been drilled into the pubic bone and not inferiorly through the tendon of the adductor longus or superiorly through the rectus fascia over the surface of the pubis. Proper location of the drill and placement of the bone anchor in the bone is facilitated by the drill guide illustrated in FIGS. 1–4 and discussed infra.

Once the anchor is passed into the bone, the anchor's unique memory forces the arcs to spring open to their original shape and to engage in the cancellous portion of the pubic bone. The complication of infection with use of the anchor has not been noted, which may, in part, be due to the emphasis on broad spectrum antibiotics and sterile technique with use of video endoscopy, when possible.

Anchor pubic bone fixation in one study by the inventor herein was associated with a limitation of post-operative pain allowing the procedure to be performed on an outpatient basis in many of the patients. Pubic anchor fixation may limit suspending suture pull through at the level of the rectus fascia. Any assessment of resultant improvement of long term efficacy will require longer follow-up.

Certain specific embodiments of the methods and devices of the present invention will follow, together with an example of the inventive bladder neck suspension procedure.

I. DRILL GUIDE

In accordance with one aspect of the present invention, there is provided a drill guide for locating drill sites inside a patient's body. More specifically, the invention relates to a multi-probe bone locator and drill guide centering device for locating a desired site on a bone, guiding a drill bit to the located site, retaining access to the site following drilling, and installation of a bone anchor for anchoring sutures.

Referring to FIG. 1, there is shown a surgical drill guide 10 in accordance with one aspect of the invention. Generally, drill guide 10 comprises a body 15 carrying two or more plungers 20, 21, each having a bone probe 25, 26 at its end. A guide shaft 30 is located between two adjacent bone probes 25, 26. Alternatively, one or more of the plungers 20, 21 can be eliminated, so that one or more probes 25, 26 is directly mounted within or to body 15. Thus, in a simplified design, a drill guide channel is held in proximity to two or more elongate probes such as hypodermic needles which are preferably axially movable.

Body 15 is the support structure for the drill guide 10. The body 15 may have any of a variety of exterior configurations; however, it is preferred that the body be sufficiently axially elongate to facilitate withdrawal of the sharpened distal tips 27, 28 of the probes 25, 26 therein to minimize accidental needle sticks, and generally oval or rectangular in cross section. See, e.g., FIG. 2. The inside of the body 15 has two or more identical chambers 35, 36 spaced apart from each other to accommodate a drill guide shaft 30, as will be discussed. Preferably, an annular tissue compression portion 37 of body 15 adjacent the guide shaft 30 extends slightly farther in the distal direction than the lateral sidewalls 38, 39 of the body 15. Tissue compression portion 37 is optimally provided with a rough or serrated edge surface for contacting the tissue surrounding the drill site as will be discussed.

Each chamber 35, 36 extends from the distal end of the body 15 to a point near the proximal end of the body 15. In this manner, chambers 35, 36 are provided with open distal ends to permit reciprocal axial motion of the bone probes 25, 26 therethrough. Proximal ends of chambers 35, 36 are provided with a stop such as end walls 40, 41 having central passageways 42, 43 therethrough for movably accepting the plungers 20, 21. Similarly, distal ends 44, 45 of chambers 35, 36 can be provided with an end wall (not illustrated) having a probe opening therein, or a pierceable septum for permitting passage of probes 25, 26 therethrough.

The exact distance between the axes of adjacent chambers 35, 36 depends on the procedure for which the device is to be used. For example, in a bladder neck suspension procedure, the axes of chambers 35 should be separated by a distance of no more than about 10 mm from their centerlines, in an embodiment having coaxial probes and plungers, so that the corresponding probe separation is also no more than about 10 mm. Preferably, the separation between adjacent probes is within the range of from about 5 mm to about 15 mm.

Due to the bilateral symmetry of the illustrated embodiment, only one side will be particularly described below. The plunger 20 preferably comprises three main portions: an engaging knob 46, a main shaft 47 and a stop 50. The knob 46 is generally a cylindrical body attached to the top of the shaft 47 and shaped for easy engagement with a thumb or hand. This knob 46 may be attached to shaft 47 in a variety of manners. For example, knob 46 is illustrated as having a recessed portion on its distal surface for accepting the proximal end of shaft 47. A screw 55, preferably flat headed, is then passed through the top of the knob into the top of the shaft 47 to securely lock them together. Alternatively, the shaft 47, knob 46 and stop 50 can be integrally molded from any of a variety of thermoplastic materials well know in the art of surgical instrument manufacturing.

The plunger shaft 47 extends from the knob 46 through the opening 42 in the proximal end wall 40 of the body 15 and into chamber 35. Shaft 47 preferably is at least about 25 mm long from the distal surface of the knob 46 to the proximal surface of end wall 40 on body 15. In this manner, the plungers 20, 21 have a sufficient range of axial travel between a first, retracted position in which the distal tips 27, 28 of probes 25, 26 are shielded, and a second, extended position in which the distal tips 27, 28 of probes 25, 26 are exposed. It is contemplated, however, that the length of the shaft 47, probe 25 and axial travel may vary depending on the intended procedure.

A stop 50 is positioned on the distal end of the shaft 47. The stop 50 and shaft 47 may either be separately fabricated or may be fashioned from one piece of material such as by known molding or lathing techniques. The illustrated stop 50 comprises a radially outwardly extending portion of the plunger 20 which travels within the chamber 35 to produce a transverse abutment surface 56. The stop 50 thus limits the proximal range of travel of the plunger 20 by engagement of the abutment surface 56 with the distal surface of end wall 40 of the body 15. The stop 50 is preferably provided at its distal end with a connector such as a standard luer for attachment of a probe 25. As will be appreciated by one of skill in the art, any of a wide variety of interlocking or complementary surface structures can be devised to accomplish the function of stop 50.

In the illustrated embodiment, the probe 25 is inserted into a threaded cap 60. This cap 60 is preferably threaded on its interior surface so that it may be attached to the correspondingly threaded distal end of stop 50. Alternatively, the probe 25 can be connected to the stop 50 or shaft 47 such as by molding the proximal end of the probe 25 therein.

Each probe 25, 26 extends from the corresponding shaft 47 towards the distal end of the chamber 35. Probe 25 may comprise standard hypodermic tubing such as a standard needle, or a solid wire probe preferably having a sharpened distal end.

The length of the probe 25 is preferably such that when the plunger 20 is in a fully retracted state, the distal end of the probe 25 is spaced by at least about 4 mm from the open distal end of the chamber 35. In this manner, the probe end is protected against contamination and the user of the drill guide 10 is protected against accidental probe sticks. Alternatively, the probes 25, 26 can be rigidly secured to the body 15 or directly to a tubular drill guide shaft 30 as will be apparent to one of skill in the art.

In an embodiment having axially movable plungers, the plunger 20 is normally retracted proximally such that the distal tip 27 of probe 25 connected thereto is recessed from the distal end 44 of the chamber 35. This position is preferably releasably maintained by engaging rods 65 which are biased in the direction of annular recess 75 in the shaft 47 of the plunger 20.

In the illustrated embodiment, annular recess 75 is provided in the plunger shaft 47 at a point adjacent the proximal end of the body 15. When the plunger 20 is retracted, recess 75 releasably receives rod 65. This rod 65 is biased such as by a spring so that it provides an interference fit within recess 75 and holds the plungers 20 in their retracted position. The rods 65 and springs are preferably mounted within a housing adjacent the proximal end of the body 15.

A drill guide shaft 30 extends axially in between the two chambers 35, 36 containing the plungers 20, 21. Preferably, drill guide shaft 30 is disposed approximately equidistant from the longitudinal axis of each of chambers 35, 36 so that when each of the probes 25, 26 is in contact with a bone, the axis of drill guide shaft 30 will be spaced well away from the edge of the bone. In addition, in the illustrated embodiment, the axis of shaft 30 is offset laterally from the plane connecting the axes of chambers 35 so that the axes of the two probes and the drill guide shaft 30 are disposed on vertices of a triangle. See FIG. 2. This configuration facilitates the use of a slot 31 extending the length of guide shaft 30 for receiving a suture during the installation of the suture anchor.

Drill guide shaft 30 is optionally surrounded by an elongate tubular bushing 80 extending throughout at least a portion of the body 15, and preferably positioned so that the distal end of the bushing 80 is slightly recessed from the distal portion 37 of body 15. This bushing 80 aids in properly centering a later installed drill bit and acts as a channel through which a suture anchor is introduced into the hole after drilling.

Figure 3:
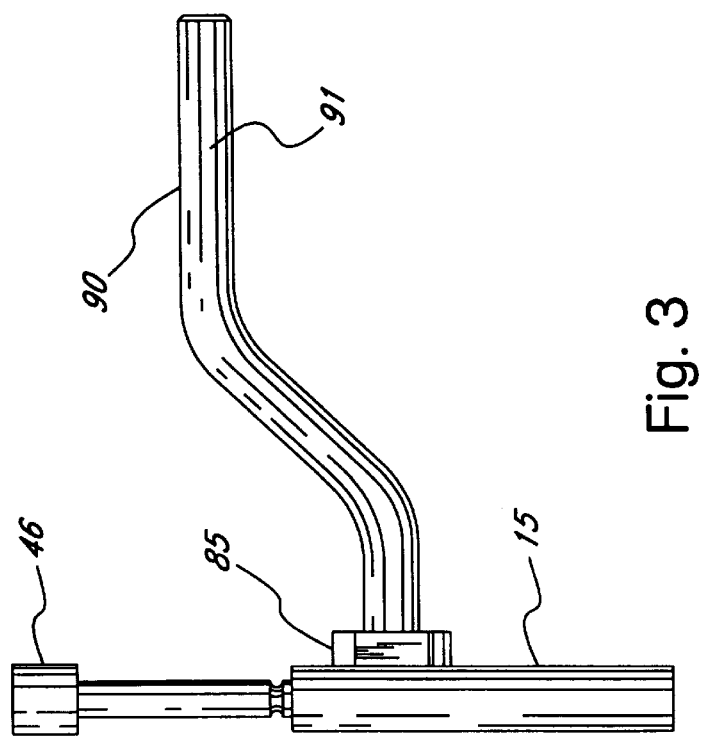
FIG. 3 is a side elevational schematic view of the drill guide of FIG. 1.

Referring to FIG. 3, there is disclosed a handle 90 connected to the outside of the body 15 for maneuvering the drill guide 10. This handle 90 is preferably generally tubular in shape, and approximately 10 mm in diameter for easy gripping by the user. The handle 90 as illustrated extends from its connection with the body 15 laterally away from said body, then upward and outward at an angle, and finally ends in a gripping section 91 which extends generally along a perpendicular to the axis of the body 15. This handle design permits the user to forcefully press the drill guide 10 against the body, as well as to facilitate controlled translation of the drill guide along a sagittal axis.

The handle 90 may be connected to the body 15 in any of a variety of conventional manners. In the illustrated embodiment, the handle extends into a small recess in the body 15 and then is locked in place such as with a nut 85. The nut 85 as illustrated has a threaded portion for engaging the body, and a locking portion for pushing the handle 90 into the body 15. Alternatively, the handle 90 can conveniently be integrally molded with body 15, or secured thereto such as by thermal or solvent bonding techniques or by adhesives well known in the art.

It is preferred that the components of the drill guide 10 be made of a material which is sterilizable, relatively rigid and biocompatible, such as stainless steel or any of a variety of polymers conventionally used for medical instruments of the type designed to enter the sterile field.

The operation of the surgical drill guide 10 will now be described. When it is desired to locate a bone for attachment of a suture anchor therein, the drill guide is placed on the body over the area of the bone. The drill guide 10 is centered after visualization or digital palpation over the bone.

The user pushes one or both of the knobs 46 to distally extend at least a first probe 25. The probe 25 is extended into the body by pushing the plunger 20 down, until either the plunger has been fully extended or the bone is contacted.

If the plunger extends fully without the probe contacting the bone, the probe is retracted and drill guide 10 is then repositioned for another attempt at locating the bone.

When the first probe 25 does engage the bone, pressure is released from the knob 46. The user then extends the second probe 26 by pushing on the corresponding knob of the second plunger 20. Once again, the second probe 26 will either engage the bone or the plunger 20 will fully extend without contact. If no contact is made by the second probe 26, both probes 25, 26 are retracted again by pulling upward on the appropriate knob. The drill guide 10 may then be translated along the sagittal axis and one or both probes reextended.

This process is continued until both probes 25, 26 contact the bone. At this time, the user will be assured that the bone has been located and that the guide shaft 30 is properly centered over the bone.

A drill bit is then extended through the drill bushing 80 and into the patient. The drill bit is used to drill through adjacent tissue and produce a small hole in the bone. Preferably, a step drill or other limiting structure is utilized for producing a hole having a predetermined and reproducible depth into the bone. For installation of the preferred Mitek G2 anchors disclosed herein, a 2.5 mm diameter drill bit is used to produce a hole of 15 mm depth into the bone.

The desirability of having a tissue compression portion 37 which extends distally slightly beyond the distal end of the adjacent body is now apparent. At the time the drill bit is retracted, the hole drilled would normally close upon itself because of the resiliency of the surrounding tissue. However, by maintaining pressure on the body 15 in the direction of the bone, the tissue compression portion 37 tends to compress the adjacent tissue thereby minimizing migration and maintaining the hole open.

In this manner, the tissue located directly under the guide shaft is prevented from closing, and the anchor can be readily advanced through guide shaft 30 and into the bone. Even without distally extending tissue compression portion 37, installation of the anchor is greatly simplified using the drill guide of the present invention because the axis of drill guide shaft 30 remains directed at the drill hole.

Following retraction of the drill bit, a suture anchor is advanced into the body through the drill bushing 80 and then connected within the hole in the bone. An installation tool which facilitates holding the anchor body by means of an interference fit at the gripping point and guiding said anchor through the guide hole and compressed tissue into the bone hole is preferably utilized. The suture, typically previously connected to the anchor, is permitted to trail out through the slot 31 provided for that purpose.

Referring to FIGS. 19–23, there is shown an alternative embodiment of a drill guide for use in locating drill sites inside a patient's body. As illustrated, the drill guide 210 comprises a body 215 carrying one or more probes 225, 226. A drill guide bore 230 is preferably located between the bone probes 225, 226.

The body 215 is the support structure for the drill guide 210. The body 215 may have any of a variety of exterior configurations; however, it is preferred that the body be sufficiently axially elongated to facilitate withdrawal of the sharp distal tips 227, 228 of the probes 225, 226 therein to minimize accidental needle sticks. Body 215 is generally oval or rectangular in cross section.

Body 215 is provided with one or more bores 235, 236 extending therethrough (FIG. 20). As illustrated, the bores 235, 236 are spaced apart from each other to accommodate a drill guide bore 230. It is contemplated that the drill guide bore 230 may coincidentally be one of the bores 235, 236, in which case the spacing between bores 235, 236 can be reduced. If only one probe 225 is used, there may only be one bore 235, and this bore 235 may coincidentally be the drill guide bore 230 also.

Preferably, the distal end 237 of the body 215 is provided with a number of serrations 234 (FIGS. 22 and 23). In the illustrated embodiment, serrations 234 are located approximately 1 mm apart and run generally parallel to the longest dimension longitudinally across the face of distal end 237. The serrations 234 are sharp ridges formed between curved grooves which have a diameter of about 0.5 mm and extend into the face of the distal end 237.

The exact distance between the axes of the adjacent bores 235, 236 depends on the procedure for which the device is to be used. As illustrated in FIG. 23 and as used in a bladder neck suspension technique, the axes of the bores 235, 236 should be separated by a distance of no more than about 9 mm between centerlines. In this manner, the corresponding probe separation in a two probe embodiment is also no more than about 9 mm. While this is the preferred separation distance, it is also possible for the separation to be anywhere within the range of between about 5 mm and about 10 mm.

Each probe 225, 226 preferably comprises a unitary element such as a wire or needle. An engaging knob 246 is mounted to the proximal end of each probe 225, 226. Knob 246 is a generally cylindrical body which is shaped for easy engagement with a thumb or hand. Knob 246 may be attached to the probes 225, 226 in any of a variety of manners well known in the art. As illustrated, the knob 246 is stainless steel, but may be molded from a thermoplastic material, and provided with a recess for receiving the top of the corresponding probe 225, 226.

The probes 225, 226 extend distally from each knob 246 and into the body 215 through the bores 235, 236. The probes 225, 226 are preferably at least approximately 75 mm long from the distal surface of the knobs 246 to their tips 227, 228. In addition, the axial length of the body 215 is within the range of from about 50 mm to about 60 mm long, and preferably about 50 mm long. The probes 225, 226 thus have a sufficient range of axial travel between a first retracted position in which the distal tips 227, 228 of the probes 225, 226 are shielded inside the bores 235, 236, and a second extended position in which the distal tips of the probes are exposed. It is contemplated, however, that the length of the probes 225, 226 and axial travel may vary depending on the intended procedure.

The knobs 246 act as limits on distal travel of the probes 225, 226, by engagement with the proximal surface of the end wall 240 of the body 215.

The length of the bores 235, 236 is preferably such that the distal tips 227, 228 of the probes 225, 226 are spaced by at least about 3 mm from the open distal end of the bores 235, 236 at the distal end 237 of the body 215 when the probes are retracted. In this manner the probe end is protected against damage, and the patient and user of the drill guide 210 are protected against accidental probe sticks.

Probes 225, 226 are preferably provided with a means for providing a bias in the proximal direction, to releasably retain the probes in the retracted state when not in use. In addition, sufficiently strong biasing means can assist in retraction of the probe from body tissue. The bias may be provided in any of a variety of ways known in the art such as with the use of coil springs. Preferably, a tapered conical section (not shown) is provided on the body of the probes 225, 226. A matching tapered step (not shown) is provided in each bore 235, 236. The conical section and step are arranged to engage each other so that the probes 225, 226 are maintained in a retracted state during non-use because of friction. The probes 225 and 226 may easily be released upon light finger pressure on the knobs 246. Alternatively, any of a variety of releasably retention structures for opposing a bias may be utilized as will be apparent to one of skill in the art.

As illustrated in FIGS. 19, 20 and 23 a drill guide bore 230 extends axially in between the bores 235, 236 which contain the probes 225, 226. Drill guide bore 230 in the illustrated embodiment is essentially coplanar with bores 235, 236. However, depending upon the desired diameter of drill guide bore 230 and spacing of bores 235, 236, drill guide bore 230 can be offset from the plane of bores 235 and 236. In general, the minimum diameter of drill guide bore 230 is set by the desired drill bit size and by the desired bone anchor, as has been previously discussed. Typical bone anchors of the type used herein are on the order of 2 mm in diameter.

Preferably, the drill guide bore 230 is disposed approximately equidistant from the longitudinal axis of each of the bores 235, 236 so that when each of the probes 225, 226 is in contact with a bone, the axis of the drill guide bore 230 will be spaced well away from the edge of the bone. In addition, the drill guide bore 230 preferably has a slot 231 extending the length of the guide bore 230 for receiving a suture, and for removing the drill guide after an anchor and suture have been installed.

As illustrated in FIG. 21, a handle 290 is connected to the outside of the body 215 for maneuvering the drill guide 210. The handle 290 preferably comprises two sections: a gripping portion 291 and an attachment portion 292. The attachment portion 292 extends from its connection with the body 215 upward at an angle of about 45 degrees to its connection with the gripping portion 291 which extends generally along a line parallel to the axis of the body 215.

The attachment portion 292 can be connected to the body 215 in any of a variety of conventional manners. In the illustrated embodiment, the attachment portion 292 is brazed to the outside of the body 215. The attachment portion 292 could alternatively be integrally molded with the body 215, or it could be otherwise secured to the body 215 by conventional welding, solvent, thermal or adhesive bonding techniques, or fastened with screws or the like.

The gripping portion 291 is preferably approximately 140 mm in length and about 20 mm wide. The gripping portion is about 30 mm thick throughout most of its length, however, near its connection with the attachment portion 291 it tapers at approximately a 45° angle to a thin section of 10 mm thickness and 30 mm length which acts as a thumb rest for the user.

The gripping portion 291 is preferably rotatable about an axis which is perpendicular to the axis of the probes 225, 226. The gripping portion 291 is thus, as illustrated, mounted on a pin 293 which extends from the bottom surface of the attachment portion 292 into a matching hole in the gripping portion 291 and clamped with a centrally located screw.

It is preferred that the components of the drill guide 210 as embodied be made of a material which is sterilizable, relatively rigid and biocompatible, such as stainless steel or any of a variety of polymers conventionally used for medical instruments of the type designed to enter the sterile field.

The operation of drill guide 210 is the same as that described for the embodiment illustrated in FIGS. 1–4. Operation of the single probe embodiment (not illustrated), will be apparent to one of skill in the art in view of the disclosure herein.

If the drill guide 210 has only one probe, the guide is pressed firmly against the skin in the area over where the bone is believed to be located. The probe 225 is pressed into the body with the knob 246. If the probe 225 does not contact bone firmly, the guide 210 is moved and the probe is re-inserted. Once contact has been established, the probe 225 may be removed from the bone 235 and the drill bit is preferably inserted through the same bore for drilling the hole. Once drilled, pressure is maintained on the drill guide 210 in the distal direction. Tissue will be restrained from occluding the hole by the serrations 234 located on the distal end 237 of the probe 225.

II. SUTURE PASSER

In accordance with another aspect of the present invention, there is provided a suture passer adapted for grasping and passing internal sutures, such as to construct the sling disclosed herein. The suture passer of the present invention is particularly suited for use in connection with such surgery as the bladder suspension procedure disclosed herein, where sutures are required to be advanced and withdrawn without direct visualization and through relatively long distances. Alternatively, the suture passer may be used with other techniques such as Pereyra, Stamey and Gittes methods.

The suture passer of the present invention enables the clinician to avoid accidental damage to the patient's internal structures and accidental needle sticks to himself and operating room personnel. The passive retraction of the needle point within the cannula, which will be discussed, facilitates the foregoing safety features, and secure capture of the suture material. The ability to advance the cannula with a blunt (retracted needle tip) end also facilitates internal suturing without direct visualization. Safe direct tactile feedback is provided along organ surfaces to localize placement of the suture. These and other features and advantages of the suture passer of the present invention will be discussed below.

Figure 5:
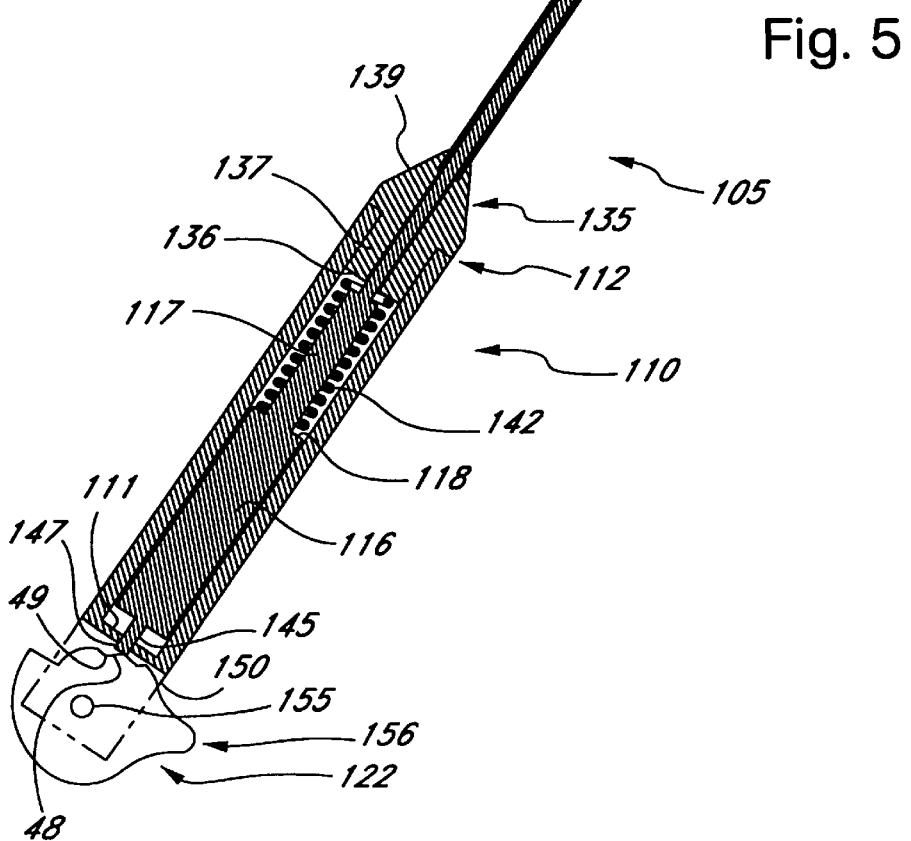
FIG. 5 is a cross sectional view of a suture passer in accordance with the present invention.

Referring to FIG. 5, there is disclosed a suture passer 105 in accordance with one aspect of the present invention. In general, suture passer 105 comprises a handle 110, an axially movable probe 115, and a probe guide 125 having a suture channel 130. Details of suture channel 130 and related structures can be seen in the enlarged view in FIG. 6.

Handle 110 serves both as a gripping area for the user and as a support structure for the suture passer 105. Handle 110 preferably comprises a hollow tubular body having proximal end wall 111 and distal end wall 112. Handle 110 is preferably of such a size to be easily gripped by a user. A handle 110 being at least approximately 0.75 inches (20 mm) in diameter and 4 inches (110 mm) in length has been found to work well. Preferably, handle 110 is provided with knurling or other surface texturing to produce a high friction gripping surface.

A support 135 is preferably mounted such that it extends from the distal end of the handle 110 to provide a mounting support for probe guide 125. The support 135 as illustrated is provided with a generally cylindrical proximal section 137 for engagement within the distal end of the handle 110 and a tapered distal section 139 for securing probe guide 125. The support 135 acts as a transition member from the handle 110 to support the probe guide 125.

The probe guide 125 comprises an elongated tubular member which is at its proximal end inserted within or secured to the support 135. The probe guide 125 may be fixed to the support 135 in any variety of manners, including brazing, threading or others known in the art.

The probe guide 125 extends distally therefrom and is preferably within the range of from about 6 inches to about 8 inches in length and may be straight or curved. The length of probe guide 125 may vary, of course, depending on the exact intended procedure.

At its distal end, the probe guide 125 is provided with a smooth tapered engaging face 140. The distal extreme of tapered face 140 is slightly rounded or polished so that it can be pressed lightly against and swept along the surface of tissue such as the pubocervical fascia without cutting or traumatizing the tissue.

The probe guide 125 is preferably no more than about 0.1 inches (2.5 mm) in diameter and is provided with at least one central lumen for acceptance of an axially movable probe 115. An elongate probe 115 is mounted within the handle 110 and extends through the support 135 and the probe guide 125. Probe 115 is preferably provided at its proximal end with a relatively large diameter body portion 116 adapted for reciprocal motion within tubular handle 110. Body portion 116 is preferably provided with a slightly smaller diameter recessed portion 117 for receiving a return spring 142 which biases the probe in the proximal direction. Alternatively, any of a variety of means can be utilized to provide a proximal bias on probe 115.

The length of body portion 116 is less than the axial length of the cavity within handle portion 110 so that the body portion 116 has an axial range of motion within the range of from about 2 mm to about 10 mm, and preferably about 0.12 inch (3 mm). The proximal end wall 136 of support 135 which extends into the handle 110 acts as one limiting stop for distal travel of body 116. The distal surface of end wall 111 limits proximal travel of body 116. Spring 140 pushes against an annular shoulder 118 on body portion 116, biasing the probe 115 proximally.

Figure 6:
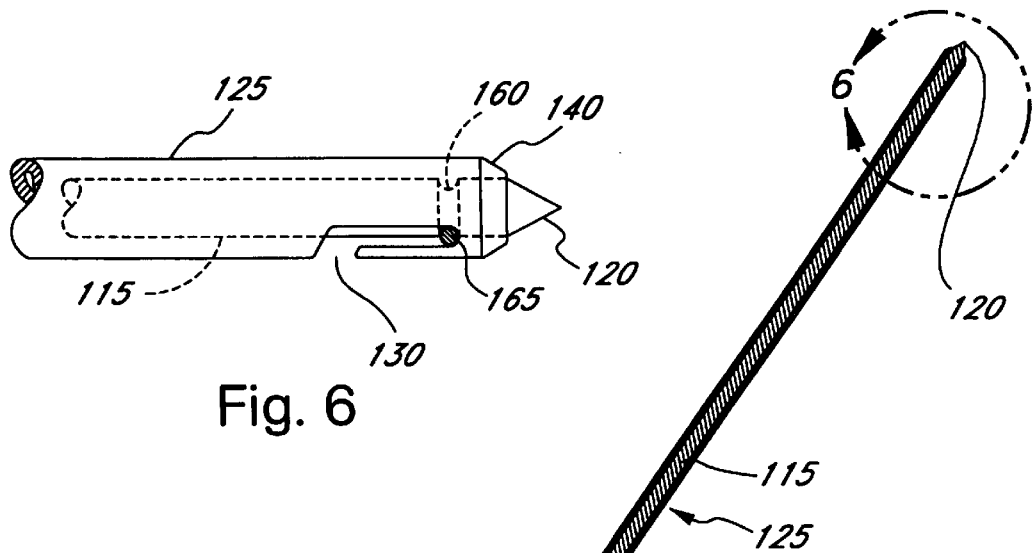
FIG. 6 is an enlargement of the distal tip of the suture passer illustrated in FIG. 5.

The distal end of probe 115 is provided with a sharpened tip 120. Spring 142 normally biases tip 120 towards a first retracted position within the distal end of probe guide 125. Axial distal force on body portion 116 extends tip 120 into a second exposed position as illustrated in FIGS. 5 and 6. Although the probe 115 may be actuated in any number of ways, such as by use of a knob or button, it is presently preferred that a rotatable cam 122 be used.

The cam 122 is attached to a post 150 which extends proximally from the handle 110. The cam 120 is rotatably mounted about a pin 155 which extends in an axis perpendicular to the longitudinal axis of the probe 115. The proximal end of the body portion 116 has a rod 145 which extends proximally through an opening 147 in the proximal end wall 111 of the handle 110.

The cam 122 has at least a two position engaging surface which, when rotated into position, engages the rod 145 of the body 116. In a first position, the bias imposed by return spring 142 is overcome and the sharpened distal end 120 of probe 115 is extended outwardly from the probe guide 125. In a second engaged position, the distal end 120 remains within probe guide 125, but the suture lock is actuated as will be discussed. In a third position, the distal tip 125 is passively fully retracted within guide 125, and the suture lock is open such as for receiving or releasing a suture.

The cam 120 is preferably provided with an actuator portion 156 which extends radially outwardly and which may be used by the operator for rotating the cam 122.

A suture channel 130 is provided near the distal end of probe guide 125. Channel 130 cooperates with an annular or slotted recess 160 near the distal end of the probe 115. Suture channel 130 comprises an opening in the probe guide 125 which extends radially inwardly into the guide 125 and then generally axially along the guide 125 towards the distal end. The annular or slotted recess 160 in the probe 115 is located such that when the probe 115 is retracted to the proximal limit, the recess 160 and the opening in the channel 130 are aligned for receiving a suture therein.

At least a portion of the suture channel 130 extends generally axially along the guide 125 such that when a suture 165 is located in the recess 160 of the probe 115, the probe 115 may be extended to an intermediate, "locked" position, or to a distal position in which tip 120 is exposed outside of the probe guide 125. In this extended probe position and at all positions between the proximal and distal limits, the suture 165 is trapped within the recess 160 in the probe 115.

As with the drill guide discussed supra, it is preferred that this instrument be manufactured from a sterilizable material having sufficient rigidity for its intended purpose. Many acceptable materials are well known in the art, such as stainless steel for the needle and needle guide, and stainless steel or a plastic for the handle portion.

The suture passer 105 is operated first by rotating the cam 122 that engages the rod 145 and extends the probe end 120 distally of the probe guide 125. The passer 105 is then extended into a patient's body by gripping the handle 110 and pushing the free end of the probe guide 125 into the body and through the layers of tissue in the same manner as the Stamey needle discussed in Example I, infra, and illustrated in FIGS. 9A–10H. The cam 122 is then released and rotates to its neutral position 148 via action of spring 142 against the body 116 in turn pressing the rod 145 proximally against the cam ramp 149. The probe end 120 is thereby retracted into the probe guide 125 so that the suture passer can be manipulated without injury to surrounding tissue while keeping the suture 165 trapped in channel 130.

The suture passer 105 is then guided as discussed in Example I, to the desired capture point (see FIG. 10A) and the cam 122 rotated to a position in which the suture channel 130 is aligned with the recess 160 of the probe 115. A length of suture 165 is transvaginally introduced at the introitus and digitally pressed against the outside of the probe guide 125 at a point proximal to the suture channel opening 130.

The suture 165 is then moved proximally until the suture 165 falls into the channel opening 130 and the annular or slotted recess 160 on the probe 115. The cam 122 is then released so that rod 145 slides down cam ramp 149 under the bias of spring 142. At this time, the suture 165 is held securely within the channel 130, and distal tip 120 is retracted within guide 125. Preferably, channel 130 and recess 160 are dimensioned so that the suture 165 is slidably retained therein. The passer 105 may then be retracted from the body, thus drawing the suture 165 from inside the body. The construction of a bladder neck suspension web utilizing the suture passer will become apparent from the method disclosed in Example I, infra.

III. SUTURE TENSIONING

In accordance with another aspect of the present invention, a reproducible technique of tying the suspending suture is described. Tying down on something with the approximate dimension of the distal pulp of an index finger leaves a small amount of slack in the suture which permits a controlled and limited suspension of the bladder neck when suspended in this way. The slack is acceptable because of the large volume of pubocervical fascia lending support to the bladder neck. In the prior art, it has been observed to be relatively easy to place excessive tension on the bladder neck. Chronic urinary retention is avoided by utilizing the suture tensioner disclosed herein, and the chance of acute retention is minimized, thereby promoting a reduction in periods of indwelling and intermittent catheterization.

Chronic retention with endoscopic bladder neck suspension has been reported in as many as 5 to 18.9 percent of patients in other series[11,12]. Excessive tension with overcorrection of the bladder neck is also known to account for bladder instability[13]. In the study by the present inventor, urinary urgency and urgency incontinence diminished following surgery with the limitation of suture tension described herein. This reduction in irritative urinary symptoms was also associated with the lateral placement of the pubocervical sutures.

The period of hospitalization was reduced within the tension limiting group in the experimentation conducted by the inventor herein. A limit on suture tension may be found, over time, to decrease suture pull through at the pubocervical fascia and, therefore, enhance long term efficacy. The one failure in the study conducted by the present inventor occurred in a patient who had the suspending suture tied in the prior art tighter and more arbitrary manner.

The modifications described herein attempt to further reduce the limitations of the present forms of bladder neck suspension in a select group of patients with SUI (grade 1 and 2). Safety and short term efficacy of the modifications were good. Patient inconvenience in terms of the period of hospitalization and intermittent catheterization was limited. The period of indwelling catheter drainage will be shortened in the future. Satisfaction in the patient group was high. The priority of improved long term efficacy is stressed in these techniques that allow the accurate and secure placement of suspending sutures in a reproducible manner that minimizes the tensions placed upon those tissues that are suspended.

As an alternative to tying down against the index finger, there is provided herein a suture tensioner for providing consistent, repeatable amounts of slack (tension) in the suture sling. As with the use of the index finger described supra, the use of the suture tensioner minimizes post-operative urinary blockage caused by excessive tension, and minimizes post-operative urinary incontinence due to insufficient tension. In addition, the suture tensioner permits the visualization of suture knots during tying, thereby ensuring consistency of alignment and tension of knot loops.

Referring to FIG. 7, there is disclosed one embodiment of a suture tensioner in accordance with the present invention. The suture tensioner 170 may be constructed in any of a variety of ways which will be well understood by one of skill in the art of constructing medical devices, such as by injection molding or lathing processes.

The suture tensioner 170 comprises generally an elongate handle 172 and a body portion 174. The handle 172 may be integrally formed with the body 174, or may be separately produced and affixed such as by insertion into an opening 173 in the body 174, and retained therein such as by threads, adhesives or other conventional means.

The main body 174 comprises a generally cylindrical mass, having a relatively blunt distal end 176 and an annular or semi-annular recess 178 extending about an axis of the main body 174 which is generally perpendicular to the longitudinal axis of handle 172. Other configurations will also become apparent to one of skill in the art in view of the present disclosure.

In the illustrated embodiment, the annular recess 178 extends into the main body 174 to a minimum depth of about 0.2 mm to 3.0 mm, and has a radius of approximately 0.5 mm. These dimensions have been found suitable for holding the first throw of the knot while maintaining suture tension, when tying down the sutures typically utilized in the bladder suspension procedure, which typically have a diameter of about 0.5 mm. The main body 174 has an axial length of about 15 mm, and a distance between distal end 176 of main body 174 and annular recess 178 of about 8 mm.

The handle 172 extends into the main body 174 to a depth of approximately 14 mm, and the remaining exposed handle has a length of approximately 100 mm. The diameter of the main body 174 is approximately 16 mm.

As will be apparent to one of skill in the art in view of the foregoing disclosure, any of a wide variety of modifications can be made to the basic dimensions recited herein, and still permit accruing the advantages of this aspect of the present invention.

In addition to providing a reproducible amount of slack in the tied suture, the use of suture tensioner 170, spaces the knot tying region apart from the tissue during tying. The suture tensioner 170 also allows visualization of the knot while being tied. Further, the suture tensioner 170 allows the user to apply variable tension in relation to the size of the suture body.

IV. VAGINAL/ABDOMINAL DRAPE AND EXPOSURE SYSTEM

In accordance with another aspect of the present invention, there is provided a drape and exposure system comprising a vaginal drape, speculum and buttock plate adapted for isolating the surgical field, providing a mounting surface for surgical instruments, and opening the surgical area for access. More particularly, the drape, speculum and plate are particularly suited for use in connection with pubo-vaginal surgery such as a bladder suspension procedure.

The drape and speculum protect the surgical area to reduce the risk of contamination, especially from the anal area. The speculum additionally protects the posterior internal structures of the patient from needle or other damage. The buttock plate provides a mounting surface for the speculum and other surgical instruments. These and other features and advantages will become apparent as discussed below.

Referring to FIGS. 24–29, there is disclosed the vaginal/abdominal drape and exposure system of the present invention. In general, the drape and exposure system comprises a vaginal drape 302, vaginal speculum 304, and buttock plate 306.

Figure 24:
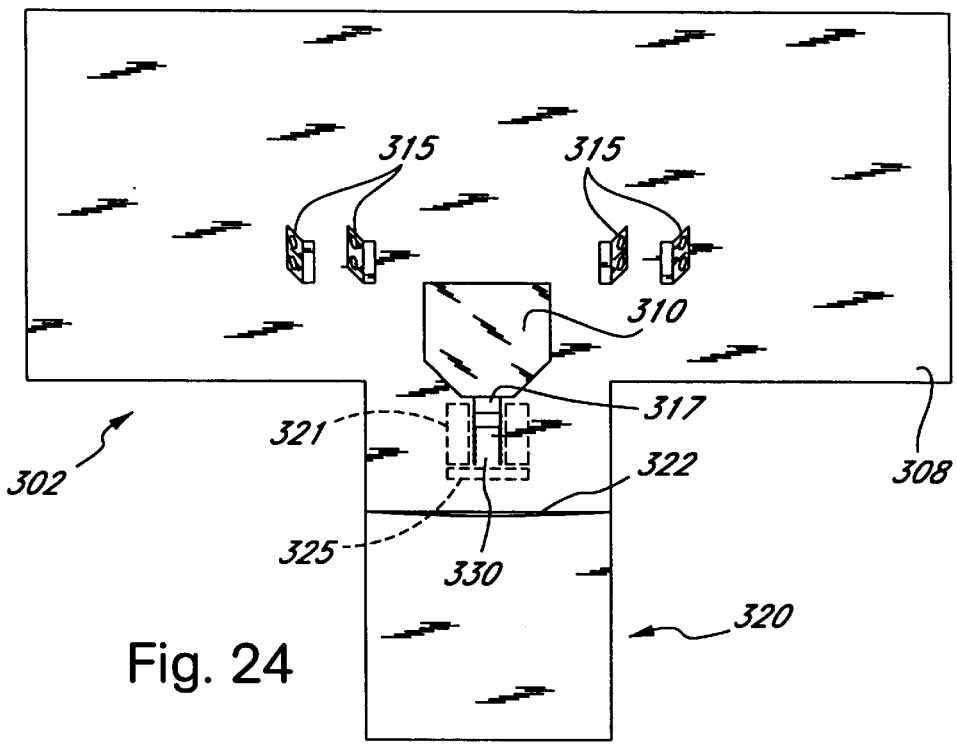
FIG. 24 is a top view of a vaginal drape of the present invention when laid flat.
Figure 25:
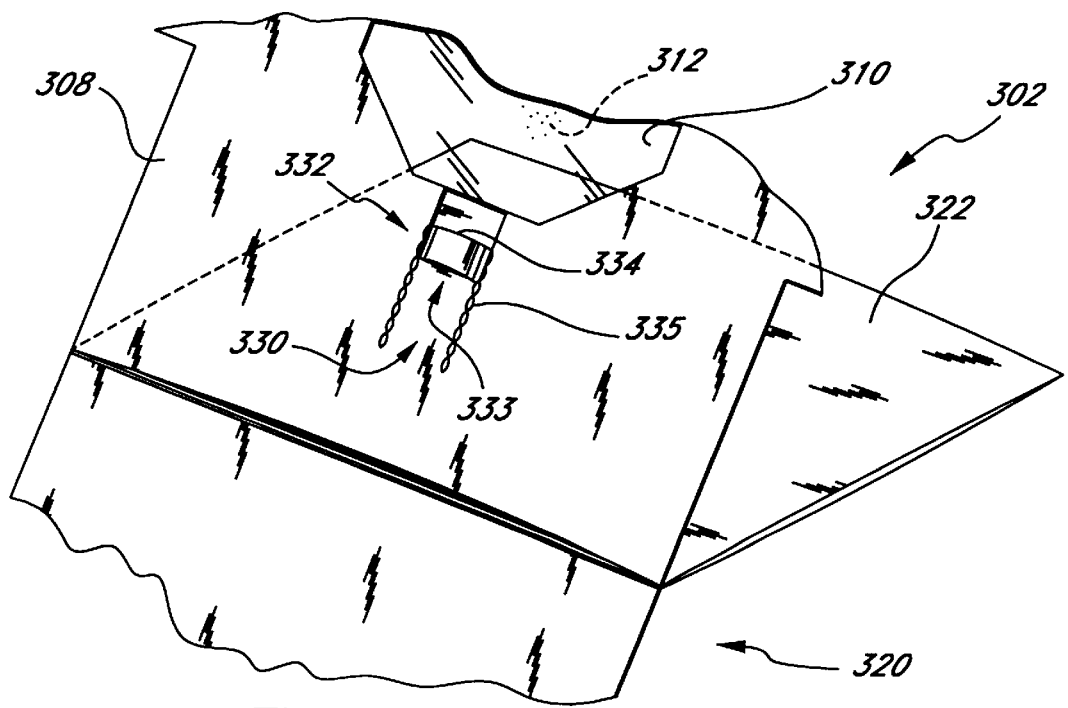
FIG. 25 is a perspective view of the vaginal drape of FIG. 24.

The vaginal drape 302, as illustrated in FIGS. 24 and 25 generally comprises an abdominal drape 308, a surgical window 310, a moisture barrier 320, and a vaginal flap 330. The abdominal drape 302 is a large, flexible, sterilizable membrane which is about 2400 mm wide and 1000 mm tall. Other dimensions may be used as will be apparent to one of skill in the art. A number of cable ties 315 are provided on the back of the drape 302. As illustrated the ties 315 are rectangular projections having holes for acceptance of tiedown cables. Alternatively the ties 315 could have a velcro surface for quick and easy attachment to a corresponding pad (not shown).

The surgical window 310 comprises a generally rectangular transparent membrane. The surgical window 310 is located in the abdominal drape 308 approximately equidistant from the lateral sides and at a distance of about 760 mm from the top edge. The surgical window 310, as illustrated, is 120 mm wide and 120 mm inches high, having the bottom 50 mm tapered inward at 45 degrees so that the base is only 100 mm wide. The window 310 may, however, be of any size or dimension depending on the particular procedure engaged in, as well as the size of the particular patient being operated on. The dimensions of the illustrated embodiment are particularly well suited for use in a bladder suspension procedures.

The surgical window 310 is preferably made from a transparent plastic which is flexible, and yet resistant to bacterial penetration and tearing. The surgical window 310 has an adhesive backing 312. Before the vaginal drape 302, and thus the surgical window 310 are installed for use, adhesive backing 312 is preferably covered with a protective sheet 314 which prevents the adhesive backing 312 from adhering to undesired items. Protective sheet 314 is preferably precut so it may be easily peeled laterally away in two or more strips approximately 120 mm wide to expose the adhesive backing 312.

An alignment opening 317 is provided just below the surgical window 310 in the moisture barrier 320. The alignment opening 317 is 50 mm by 50 mm to allow the passage of a sterile glove covered hand through it so that the user may palpate the pubic bone and guide the drape 300 into its proper position.

When installed for use, the surgical window 310 is placed over the surgical incision site. The adhesive backing 312 is exposed by removing the protective sheet 314. The surgical window 310 is then adhered to the area of the incision site.

As illustrated, the moisture barrier 320 is attached to the lower center portion of the abdominal drape 308. The moisture barrier 320 is, as illustrated, rectangular in shape, preferably being about 600 mm wide where it connects with the drape 308. The barrier 320 is approximately 900 mm long. Once again, these dimensions are variable depending on the size of the particular patient and the particular procedure being performed.

Preferably, the moisture barrier 320 is made from a material which is flexible and sterilizable, such as vinyl or polyethylene, available from Dow Chemical, or other suitable surgical drape material.

A buttock plate pocket 322 extends from about the center of the moisture barrier 320. The pocket 322 extends along the width of the barrier 320 and is preferably about 26 cm deep, being closed on its sides, back, and top. The pocket 322 allows the sterile placement of the buttock plate 306 under the patient.

The vaginal flap 330 is mounted in the moisture barrier 320 in an area near the surgical window 310. The vaginal flap 330 as illustrated in FIG. 25 is generally flat in shape, having a speculum pocket 332 at its superior end. The flap 330 is loosely connected to the moisture barrier 320 along the lateral edges of the flap with easily torn serrations. Alternatively, the flap 330 may be made of an elastic material, with or without a speculum pocket 332, which allows the vaginal speculum 304 and stretched flap 330 to easily be placed into the vagina, providing a positive barrier against anal contamination.

The vaginal flap 330 is approximately 110 mm long and has a width of approximately 50 mm. The vaginal flap 330 is preferably formed as part of the moisture barrier 320 and thus is made of the same material as the moisture barrier. The speculum pocket 332 is generally flat with an open end 333 at its connection with the vaginal flap 330 extending to a closed end 334.

Adhesive backing strips 321 are located on the rear side of the moisture barrier 320 adjacent either side of the vaginal flap 330. The adhesive strips 321 are preferably approximately 50 mm wide and covered with protective sheets. Additionally, another adhesive strip 325 covered with a protective sheet 326 during non-use, is located just below the vaginal flap 330. This strip 325 is approximately 25 mm wide and extends 75 mm to either side of the centerline of the vaginal flap 330.

Figure 26:
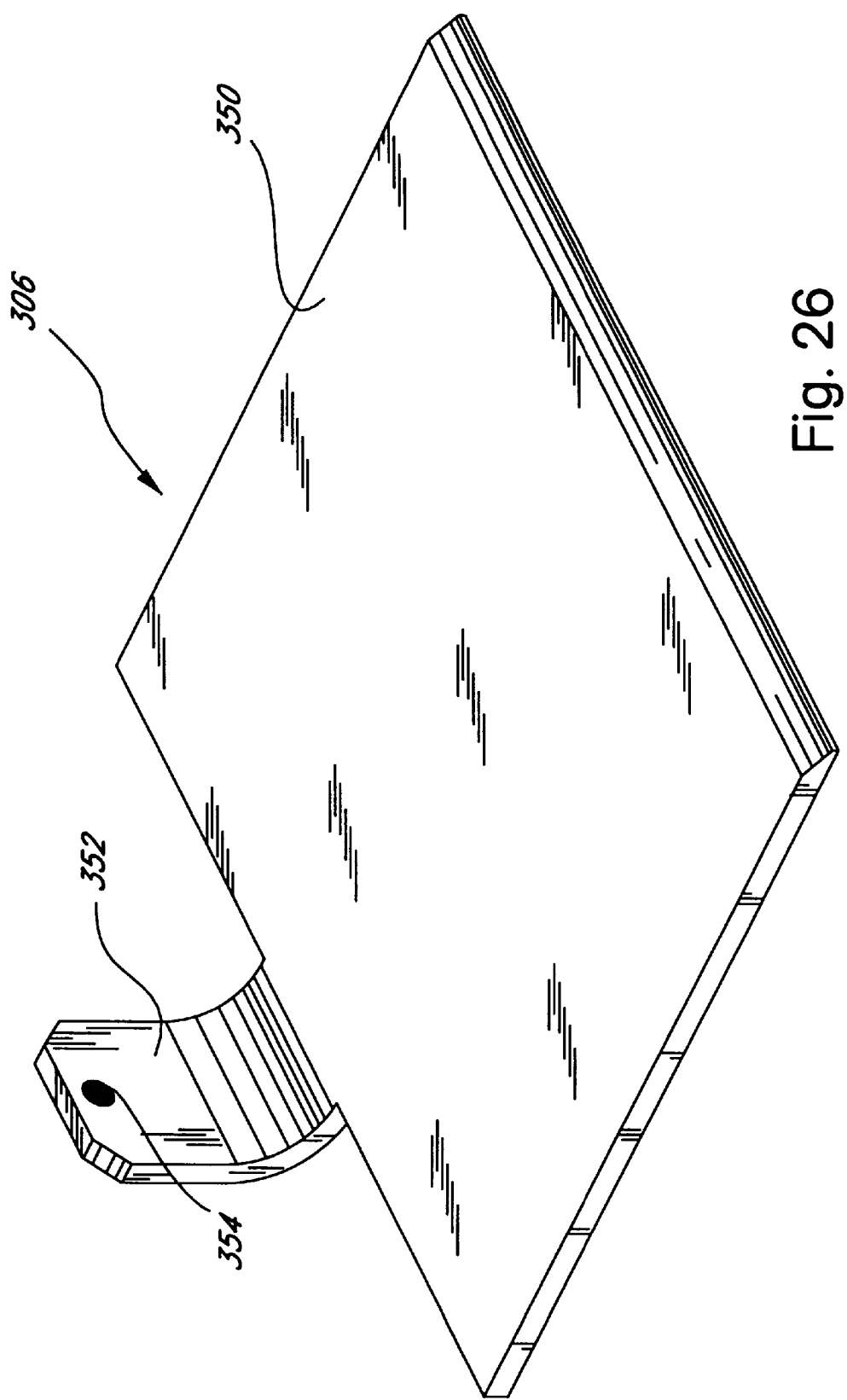
FIG. 26 is a perspective view of a buttock plate in accordance with the present invention.
Figure 29:
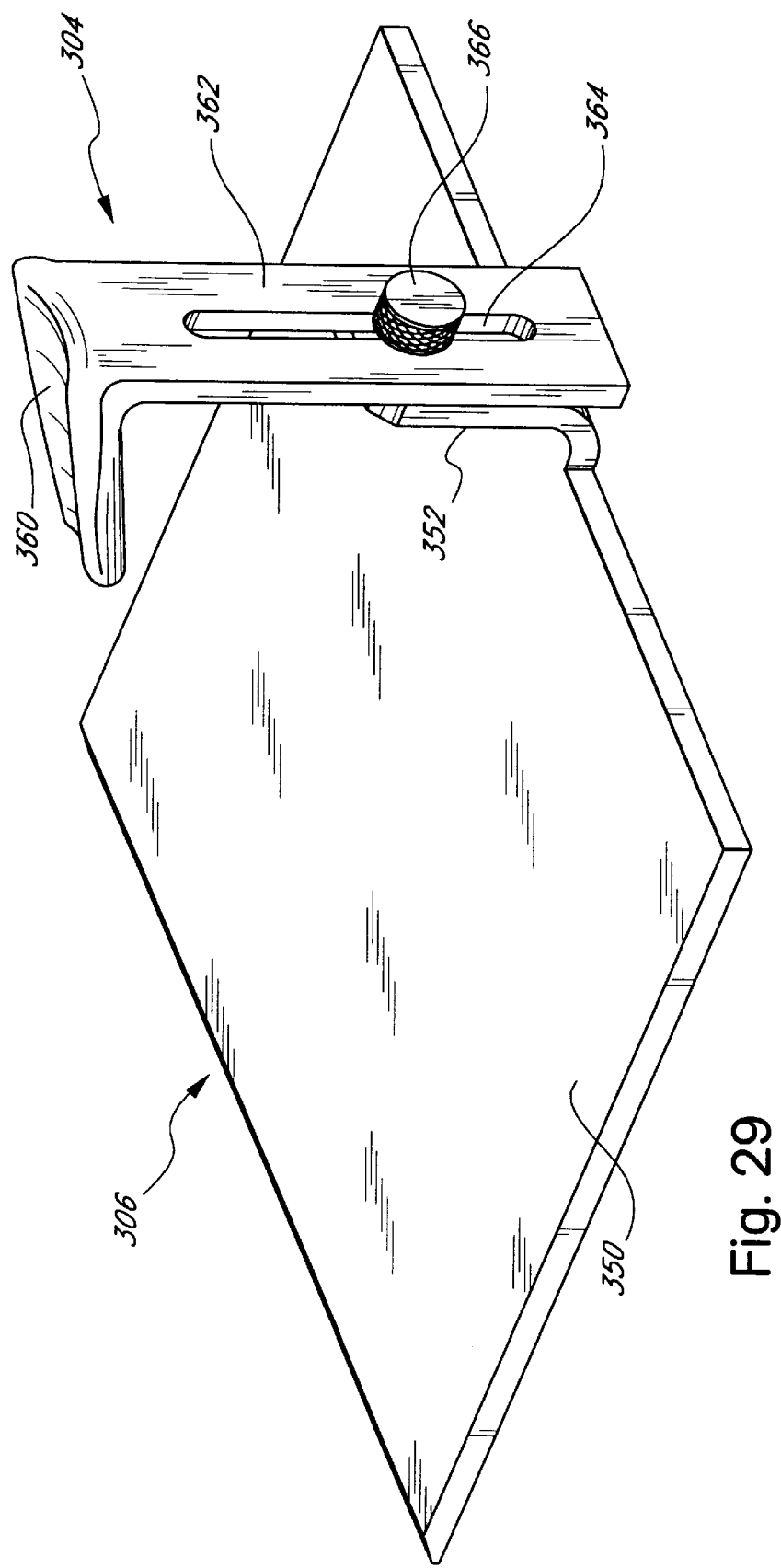
FIG. 29 is a perspective view of the buttock plate of FIG. 26 and the speculum of FIG. 27 attached in combination.

The buttock plate 306 is illustrated in FIGS. 26 and 29. The plate 306 comprises mainly a flat, rectangular support surface 350, and an upwardly extending mounting arm 352.

In the illustrated embodiment, the support surface 350 of the plate 306 is about 220 mm wide and nearly 180 mm long. The support surface 350 has a thickness of about 3 mm, although this and other dimensions dictated primarily by desired structural integrity may be varied depending upon the construction material. At one end the support surface 350 is tapered at about a 45 degree angle. The upwardly extending mounting arm 352 is located opposite the tapered end of the support surface 350.

The upwardly extending mounting arm 352 of the plate 306, as illustrated, is part of the support surface 350, however it is contemplated that the upwardly extending mounting arm 352 could be a separate member which is connected to the support surface 350. The upwardly extending mounting arm 352 is approximately 50 mm tall and 50 mm wide.

The upwardly extending mounting arm 352 has a bore 354 located in it along the centerline axis of the width of the plate 306 and at a height of 40 mm above the bottom of the support surface 350. This bore 354 is preferably threaded and has a diameter of about 0.250 inches.

It is preferred that the entire buttock plate 306 be made from a material, such as stainless steel, which is sterilizable and relatively rigid.

Figure 28:
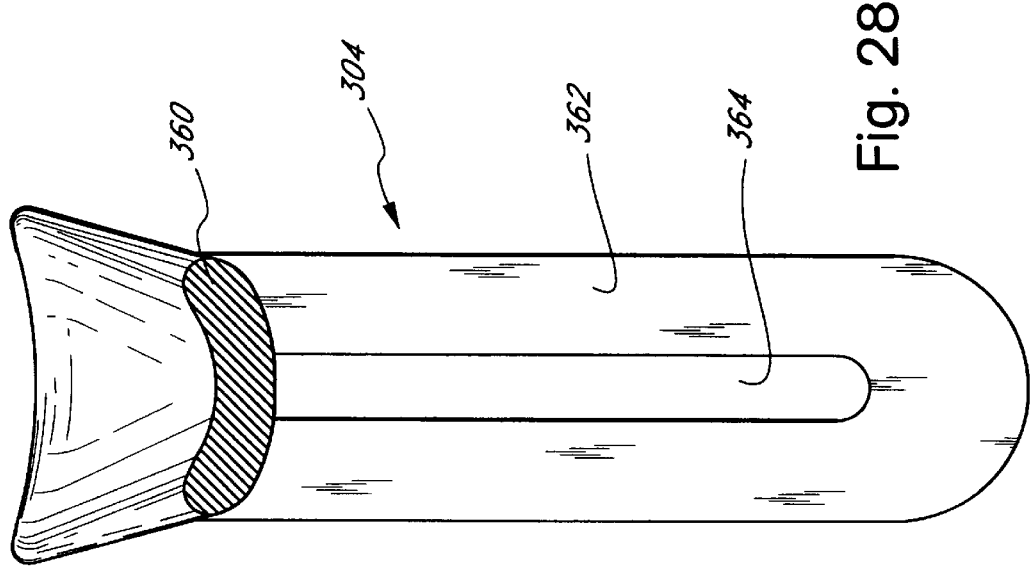
FIG. 28 is a front view of the speculum of FIG. 27 taken along line C—C.
Figure 27:
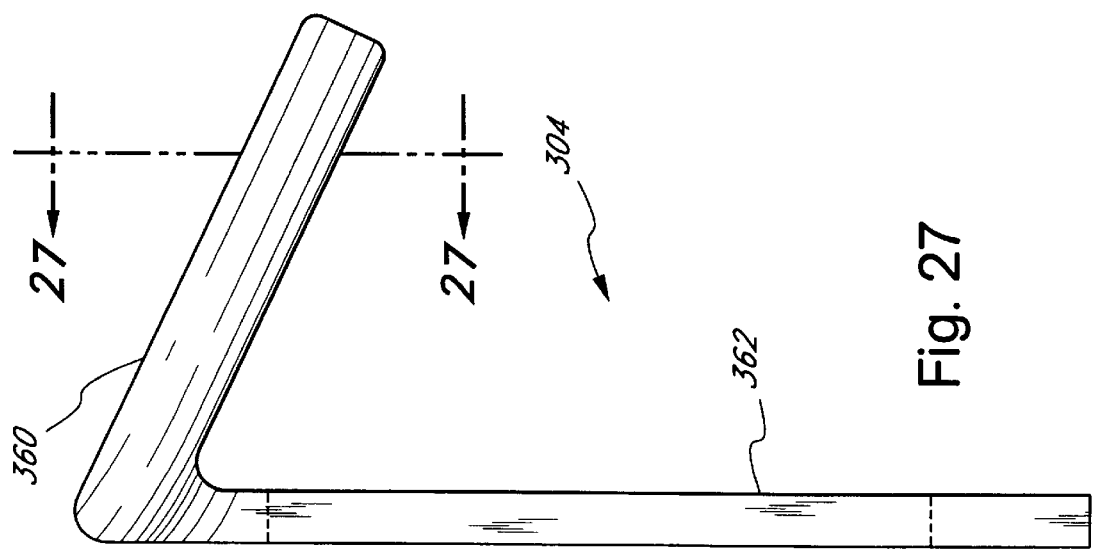
FIG. 27 is a side elevational view of a speculum of the present invention.

Referring to FIGS. 27–29, there is shown the vaginal speculum 304 of the present invention. The vaginal speculum 304 generally comprises an elongated concave member 360 and a support stem 362. The concave member 360 is a semicircular plate approximately 110 mm long. The member 360 has a semi-circular cross section which would be 90 mm in diameter at its proximal and distal ends if the member formed a complete circle. However, the member 360 forms only a partial circle, extending such that its proximal end width is 45 mm and its distal end width is 38 mm. These dimensions are fairly typical of those that will provide a speculum 304 which may be used on most patients. However, due to variation in patient size, etc., it is contemplated that these dimensions may be readily changed to accommodate such variations.

The support stem 362 is mounted to the proximal end of the concave member 360. The support stem 362, as illustrated, is molded as part of the concave member 360, although it is contemplated that the support stem could be a separate piece which is later attached to the concave member.

The support stem 362 is about 150 mm in height from the highest point on the concave member 360 to the bottom of the stem 362. The stem 362 is approximately 5 mm thick, and after extending down from its connection with the concave member is approximately 40 mm wide. The stem 362 is connected to the concave member 360 such that the concave member inclines downward and inward towards the plate 306 at an angle of 25 degrees from a perpendicular to the stem 362. While the concave member 360 may extend uniformly down from the stem 362 at a 25° angle, the member 360 may also be nearly perpendicular to the stem 362 and then become arcuate in shape until it slopes at approximately a 25° angle from the horizontal.

While the stem 362 may be 5 mm thick, a thinner stem is allowable as long as its rigidity and strength are not compromised. Further, while the concave member 360 may be thick in order to retain rigidity, a thinner member allows the vaginal opening space to be maximized. Lastly, if the concave member 360 meets the stem 263 nearly horizontal and with a low profile, the ease of entry and exit into the vagina is maximized.

A slot 364 is provided in the stem 362 a short distance from its base, and extends 100 mm upwardly along the center axis of the stem. Slot 364 is about 7 mm in width. A knurled knob 366 is provided for extension through the slot 364. Knob 366 has a stem which is threaded, has an outer diameter of 0.25 inches, and is approximately 20 mm long.

It is preferred that the speculum 304 may be made from a material, such as stainless steel or aluminum, which is sterilizable and sufficiently rigid for its intended purpose.

The use of the vaginal drape 302, vaginal speculum 304, and buttock plate 306 will now be described as used in a bladder suspension procedure in conjunction with FIGS. 24–29.

When the patient is placed in the lithotomy position and sterilely prepared for the procedure, the sterile drape 300 is opened to expose the opening 317. The surgeon's fingers are inserted through the opening 317 and placed onto the area of the interior portion of the vaginal introitus. The drape 300 is then guided over the fingers and into place. At this time the surgical window 310 is aligned over the surgical area, and the protective sheet (not shown) covering the adhesive backing 312 is removed. The surgical window 310 is then pressed against the patient to adhere it securely over the surgical area. The moisture barrier 320 is then attached via the adhesive 321 and 325 to the patient's skin.

The remaining portion of the vaginal drape 302 is then pulled downward between the legs of the patient securely. The buttock plate 306 is installed in the buttock pocket 322 with the flat support surface 350 laying flat on the table. under the patient. The upwardly extending mounting arm 352 of the plate is located between the patient's legs.

As is evident, the adhesive backing 312 both secures the window 310 over the surgical site, as well as secures this end of the vaginal drape 302 to the patient so as to create a tight barrier from the buttock plate 306 to the surgical area.

Preferably, flap 330 is stretchably increased in size with the positioning of the speculum 304 into the vagina. Alternatively, the distal end of the speculum 304 is placed in the speculum pocket 333 of the drape 302. The speculum 304 and pocket 322 are then inserted into the vagina of the patient. Once in place, the speculum 304 is attached to the buttock plate 306. Referring to FIG. 29, the slot 364 in the stem 362 of the speculum 304 is located over the threaded hole 356 on the upwardly extending mounting arm 352 of the buttock plate 306. The speculum 304 is adjusted by sliding the slot 364 vertically until properly adjusted. The knob 366 is then threaded into the hole 354 and tightened to lock the speculum 304 to the plate 306. Additionally other surgical instruments may be mounted to the mounting arm 352 such as tissue retractors, clamps, etc. Alternately, the speculum 304 may be clamped in a flexible mount to allow for small movements of the patient relative to the buttock plate 306, and to provide for adjustments to the angle and orientation of the speculum 304. This may be accomplished by, for example, locating a slotted rubber hemispheres or other flexible structures (not shown) on the stem of the knob 366 on either side of the speculum stem.

V. SUTURE SUPPORT

In accordance with yet another aspect of the present invention, there is provided a suture support which is used to anchor sutures with respect to soft tissue inside the body. The suture support reduces the trauma to internal body tissue which can occur when a suture is tied off solely in tissue, by increasing the tissue area which supports the forces exerted by the suture. In the context of a bladder neck suspension procedure, the suture support is intended to keep a suture from pulling though the vaginal wall tissue.

Figure 30:
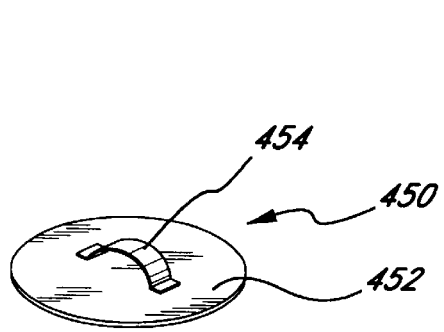
FIG. 30 is a perspective view of one embodiment of a suture support in accordance with the present invention.

As illustrated in FIG. 30, there is shown one embodiment of the suture support 450. This suture support 450 comprising a support plate 452 and a suture tab 454. The plate 452 is about 15 mm in diameter and it is preferred that the thickness of the support 450 not be greater than the diameter of the suture, or about 1 mm. It is contemplated that the plate 452 be made in any variety of shapes, the shape dictated primarily by the location in which the suture support 450 is to be placed. The plate 452 is preferably made from plastic, stainless steel, or a poly coated stainless steel, so as to be biocompatible and sterilizable.

The suture tab 454 is a small loop connected to the plate 452 for accepting sutures. The tab 454 is preferably molded or punched as part of plate 452, however, the tab 454 could be made separately and attached to the plate 454 as would be apparent to one skilled in the art.

Figure 31:
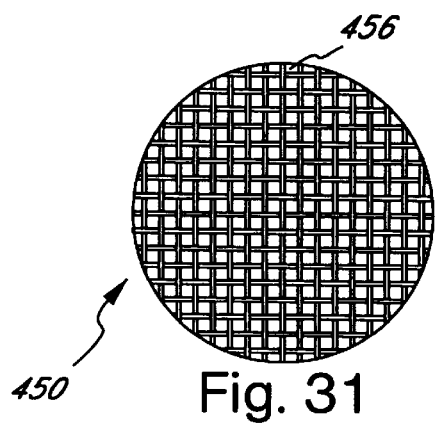
FIG. 31 is a top view of a lattice suture support in accordance with the present invention.

Referring to FIG. 31, there is shown an alternate embodiment of the suture support 450. This support 450 comprises a lattice 456 or mesh framework. Mesh type suture supports may be preferred since the tissue contact area is minimized for a given load distribution are compared to a solid plate type embodiment. This can facilitate tissue ingrowth, and tends to minimize localized necrosis beneath the support.

Figure 32:
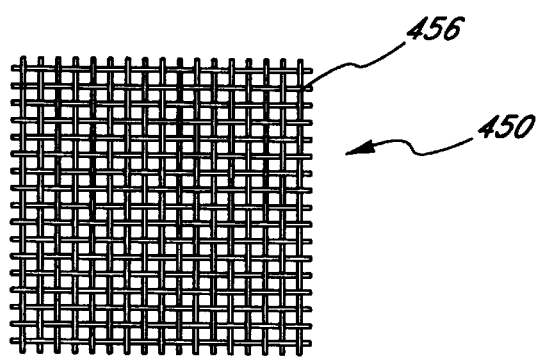
FIG. 32 is a top view of an alternate embodiment of the lattice suture support in accordance with the present invention.

The lattice 456 is preferably constructed from plastic, such as polypropylene, or stainless steel wire having a diameter of about 1 mm. The illustrated lattice 456 has a circular outer edge, with a diameter of about 15 mm. The lattice 456 could be made into the form of a square (See FIG. 32) or any other shape, depending upon the use of the suture support 450. In the illustrated embodiment, the lattice 456 itself provides a suitable tie off for sutures, and thus no other suture connector would be needed. The suture can be premolded into the lattice 456.

Figure 33:
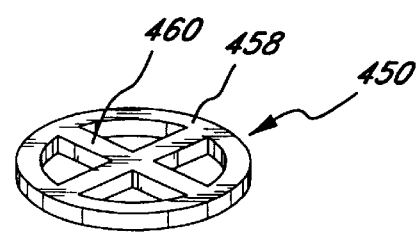
FIG. 33 is a perspective view of a spoked suture support in accordance with the present invention.
Figure 34:
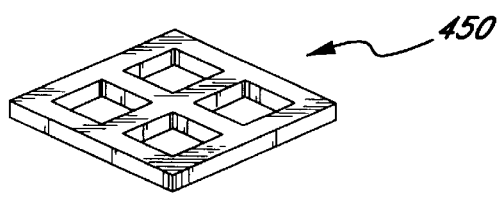
FIG. 34 is a perspective view of an alternate embodiment of the spoked suture support in accordance with the present invention.

Referring to FIG. 33, there is shown yet another embodiment of the suture support 450 of the present invention. This support 450 comprises an outer ring 458 (although the support can, of course, be square or ovoidal as shown in FIG. 34) and inner spokes 460. The outer ring 458 is a washer like member which rests against the tissue in order to support the suture. The ring 458 has an outer diameter of about 15 mm, and an inner diameter of about 13 mm. The ring 458 may, of course, be made in other shapes, such as a square or ovoidal, and may have a wider or thinner support surface depending upon the particular use of the support 450. The ring 458 is about 2 mm thick and is preferably made from polypropylene or stainless steel.

A number of spokes 460 radiate from the inner portion of the ring 458 to its center. As illustrated, four spokes 460 each 2 mm in diameter connect to one another and the ring 458. The center of the ring 458 where the spokes 460 meet, is used for attaching sutures.

It is possible that in the above embodiment of the suture support, that there only be spokes 460 and no ring 458. In this case, the suture is again tied off to a center convergence point for spokes 460, and the support for the suture is provided merely by the spokes, as no outer ring is present. In this form the suture support 450 allows for more rapid tissue ingrowth.

In the context of a bladder neck suspension procedure, the suture support can effectively be used in two ways. Placement of a suture support 450 may be made merely by pulling the suture and support upward against the tissue, such as the vaginal wall, snugly. It is also permissible for a small incision to be made in the vaginal mucosa, thus creating a mucosal flap, beneath which the suture support may be placed and then closed. Lastly, it is contemplated that more than one suture be used in conjunction with any of the above embodiments of the suture support 450. Further, it is contemplated that one end of a suture may be integrally molded with any of the above embodiments constructed of plastic.

VI. STAPLE APPLIER AND TISSUE STAPLES

In accordance with a further aspect of the present invention, there is provided a variety of tissue staples and a staple applier. The staples are an alternative to sutures and are used to connect and support tissue. In particular, the staples may be used in a transvaginal bladder suspension procedure for supporting tissue from the iliopectineal ligament or other suitable nearby ligamentous tissue or bone.

Figure 35:
FIG. 35 is a perspective view of a tissue staple in accordance with the present invention.

Referring to FIG. 35, there is disclosed a tissue staple 500 for use in the bladder neck suspension procedure of this aspect of the present invention. The staple 500 is in the form of a partial ellipse having the approximate dimensions of 10 mm along the longitudinal axis and 7 mm along the short axis. However, the precise dimensions of the staple 500 may be varied to suit particular applications, and to provide for a suitable gap between the supporting tissue and the iliopectineal ligament, as will be apparent to one of skill in the art.

Figure 36:
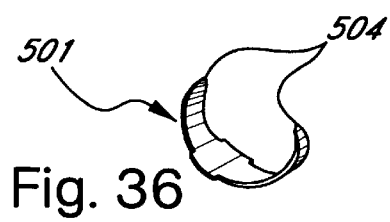
FIG. 36 is a perspective view of an alternate embodiment of the tissue staple in accordance with the present invention.

The lateral ends 504 of the staple 500 are preferably sharpened to provide easy penetration of tissue. The staples 500 are preferably stamped from a material such as stainless steel, titanium or other sheeting, with or without an outer polymeric coating, or molded or formed from a material which is biocompatible, sterilizable and which will exhibit relatively long term integrity. Alternatively, staple 500 may be formed from wire or ribbon stock, such as 0.25 mm diameter spring wire. The staples may, of course, have an enlarged center portion such as staple 501 in FIG. 36 in order to distribute the forces about a larger area of tissue. The enlarged area preferably has one or more openings to allow ingrowth of tissue.

The staple applier 502, as illustrated in FIGS. 37–39, comprises a scissor like body 510 having an opposing pair of pressing support members 512, and preferably the body 510 is also provided with a pair of releasing prongs 514. The body 510 comprises two arms 516 and two handles 518. The arms 516 may be constructed in any of a variety of dimensions, and, in one embodiment, are about 160 mm in length and 4 mm in diameter. In one embodiment, the upper arm 516 has a small flange 517 on its distal end, as well as a hole 513 extending through the flange and along the arm to a point proximal of the flange, to allow the passage of a support member 512, as will be discussed below. The arms 516 are pivotally connected about a pin 520 or other conventional fastener which passes through bores in the flange 517 in the upper arm and through the distal end of the other arm.

Handles 518 are disposed on the proximal end of each arm 516. The handles 518 are slightly elliptically shaped loops which are sized to facilitate the introduction of a fingers for manipulation of the handles. Preferably, handles 518 are formed with a loop in the proximal extension of the corresponding arm 516.

A support member 512 is mounted on the distal end of each of the arms 516. The support members 512 generally are mounted perpendicular to the longitudinal axis of the body 510, being generally concave toward each other, curving first laterally from their point of attachment with the arms 516, and then medially as will be understood from the intended function. The support members 512 are connected such that the proximal of the two members extends upwards from its connection with the lower arm through the hole 513 in the upper arm. In this manner, the proximal member is allowed to move with respect to the distal member. The support members 512 are thin curved members having a width of about 6 mm at their base which connects with the arms 516. Preferably, the remainder of the members 512 have widths corresponding with the width of the staples 500, and thus taper to a width of about 3 mm near their distal ends. The distal ends of the support members 512 are thus narrow, thin, and concave to match the curve of the staple 500, providing guidance so as to allow easy entry and closure of the staple 500 into tissue. The support members 512 should be shaped, however, so that when the arms 516 are open, the distal ends of the members 512 are approximately 15 mm from one another, thus leaving a gap between them for entry about a section of tissue. The exact radius of curvature of each of the members 512 should be such that they nearly mirror the shape of the staples 500.

Preferably, to permit removal or widening of the radius of an installed staple, an opposing pair of staple removal prongs 514 are mounted one on each member 512. The prongs 514 are solid shafts which may be generally U shaped, and comprise a component which extends generally perpendicular to both the longitudinal axis of the body 510 and the members 512. The prongs 514 thus have one end which is attached to one of the members 512, and one end which is exposed and is located a distance from the member 512. In this manner, the opposing staple removal prongs 514 are advanced towards each other and drawn apart from each other by relative manipulation of the arms 516 about pivot 520.

It is preferred that the entire staple applier 502 be made from a material which is relatively biocompatible, and sterilizable, as is well known in the surgical instrument art. The applier 502 must also be made from a material which is sufficiently rigid to accomplish the intended purpose, such as stainless steel.

The operation of the staple applier 502 will now be described in connection with FIGS. 37 and 38. The arms 516 are first distanced from one another, so that the support members 512 are also apart. A staple 500 is inserted in between the members 512 and prongs 514. The staple applier 502 is inserted into or against the portion of the body where the staple 500 is to be used. The ends 504 of the staple 500 and the distal ends of the support members 512 are pressed into the tissue in the area to be stapled. It can now be seen that because the support members 512 are mounted 90 degrees to the arms 516, the staple 500 may be applied in areas, such as the vagina, where the tissue to be stapled is located approximately perpendicular to the axis of the arms 516.

Once the staple 500 has been pressed into the tissue a sufficient distance, the staple 500 is closed by compressing the handles 518, and thus the arms 516 and members 512, together to engage the internal support structure. When this occurs, the members 512 push upon the staple 500 so as to press the free ends of the staple 500 together, thus locking material, such as tissue, inside the staple 500.

If it is necessary to remove a staple 500 from tissue or other material, the prongs 514 are used. The applier 502 is located such that the placed staple 500 is in between the members 512 and prongs 514. The handles 518, and thus the arms 516 are pulled apart. This causes the prongs 514 to move apart and pull on each side of the staple 500, causing it to expand as its free ends separate.

Alternatively, the staples 500 may be shaped so as to have straight rigid parallel lateral ends that allow the staple to be driven straight into a bone, such as the pubic bone, as would be apparent to one skilled in the art. In a further variation, a single nail-like attachment device (not shown) may be used to affix any of the suture supports 450 described in Section V. above. When using these staples 500, a slap hammer, or power driven device such as that commonly used in orthopedics and well known to those skilled in the art, may be used to place the staple, and a suitable gap between the staple and the bone is provided by the staple applier 502 so as not to crush the tissue between the bone and the staple.

Alternatively, the staples 500 may be preformed of a suitable spring material such as Nitinol in approximately the final relaxed and desired shape of a closed oval, as would be apparent to one skilled in the art. In this mode, the staple applier 502 is used to hold the staple 500 between the prongs 514 in an open state with the sharpened ends of the staple separated to allow passage through the layers of tissue. When the staple 500 is in the desired location, the handles 518 are allowed to open, which in turn allows the staple to close into its final desired shape, thus capturing and locking the desired tissue.

VII. "C" CLAMP

In accordance with another aspect of the present invention, there is provided a "C" clamp for locating and aligning a drill bit. The "C" clamp is an alternative to the drill guide of the present invention, and is designed for use with the buttock plate. The "C" clamp has a drill guide which aids in locating a drill bit through the pubic region and into the vaginal area.

Figure 40:
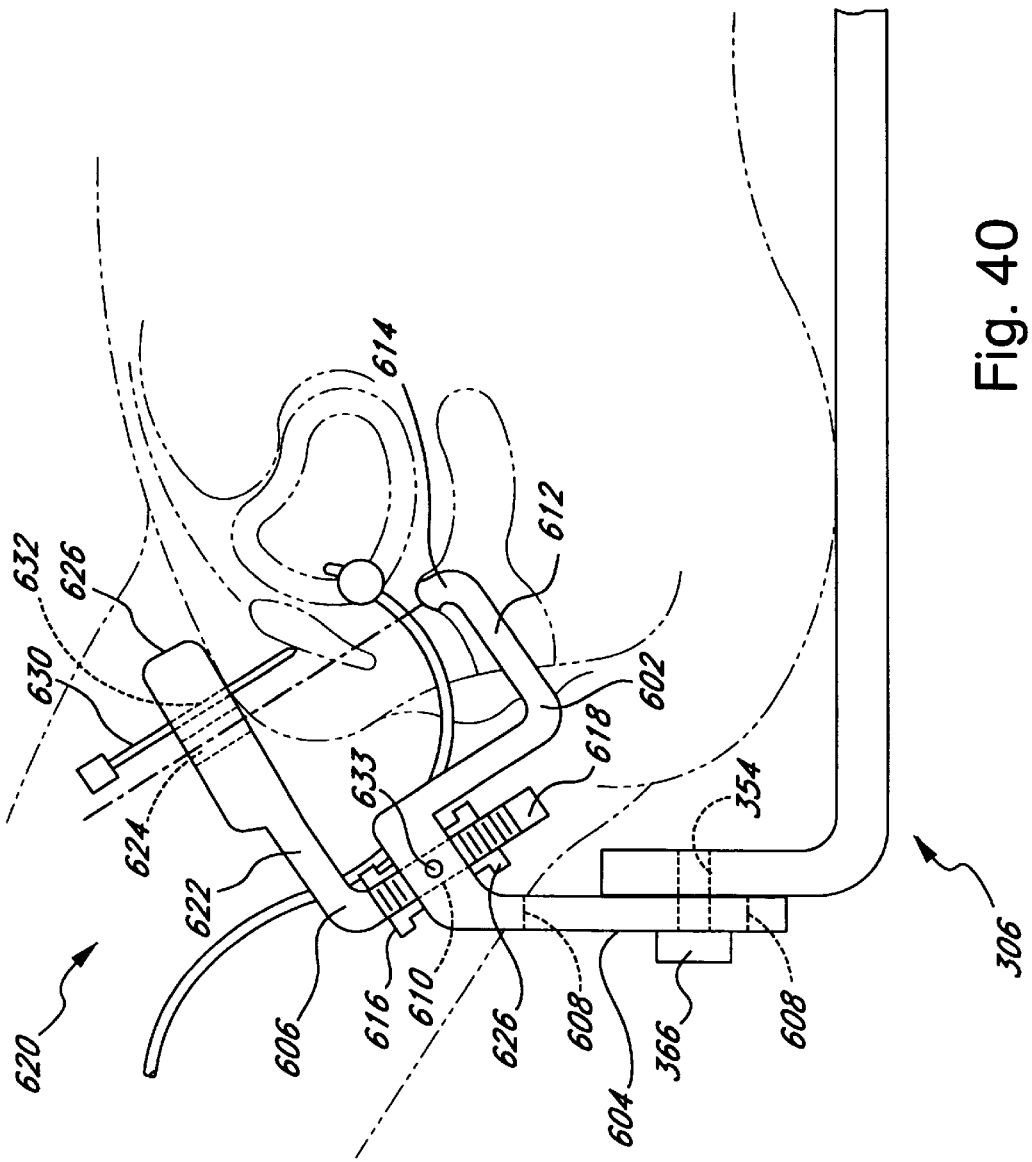
FIG. 40 is an elevational side view of a "C" clamp in accordance with the present invention illustrated in body placement.

Referring to FIG. 40, there is disclosed a "C" clamp 600 for use in the bladder neck suspension procedure of the present invention. The "C" clamp 600 generally comprises a support arm 602, attachment member 604, and guide arm 606.

The attachment member 604 is a generally rectangular plate or arm preferably having a slot 608 extending axially therethrough to permit adjustment as will become apparent. The member 604 in one embodiment is about 40 mm in width, 5 mm in thickness, and about 100 mm in length. The slot 608 is approximately 100 mm long and at least 7 mm in width, so that a bolt connected to the knob 366 which fits into the buttock plate 306 bore 354 will pass through the slot 608.

The support arm 602 is mounted to the attachment member 604. The support arm 602 is generally L shaped, having one end which attaches to the attachment member 604, a bore 610 for acceptance of the guide arm 606, and a distal end 612 which has a drill stop 614 thereon.

The support arm 602 is about 6 mm in diameter along most of its length, except where the bore 610 is located, where the arm 602 becomes flat, being about 40 mm wide and 5 mm thick. The support arm 602 extends outward to the drill stop 614 a distance of about 60 mm, so that when the support arm 602 is in place, the drill stop 614 is inside the vagina and the attachment member 604 and bore 610 are outside of the body. In one embodiment, the drill stop 614 located on the distal end 612 of the arm 602 is shaped like a half sphere, being about the same diameter as the arm 602.

The guide arm 606 is also somewhat L shaped, having a threaded shaft 616 on one side, and a drill guide 620 on the other. The shaft 616 has a diameter of about 8 mm and is about 80 mm in length. The shaft 616 is threaded along about 60 mm of its length from a distal end 618 of the shaft towards its connection with the drill guide 620. Threaded knobs 626 having an inner diameter corresponding to the outer diameter of the shaft 616 are provided for axially adjustably securing the guide arm 606 to the support arm 602, thus forming the "C" of the "C" clamp. A pin 633 is inserted through a hole in the attachment member 604 and into a corresponding in the shaft 616 so as to prevent rotation of the arm 606 relative to the support arm 602.

The drill guide 620 extends from the shaft 616 nearly perpendicular to the axis of the shaft 616. The drill guide 620 extends from a narrow neck 622 which is also about 8 mm in diameter, to a rectangular block 626 which is about 25 mm in thickness. A drill guide bore 624 passes through block 626, and is preferably about 4 mm in diameter so as to allow the passage of a drill bit.

A bone probe 630 is preferably axially movably extendable through a bore 632. Bore 632 is preferably located about 5 mm from the drill guide bore 624 on the side of the guide arm 606 farthest from the shaft 616. The bore 632 is substantially parallel to the bore 610 so that the bone probe 630 may be used to aid in locating the bone through which the hole is to be drilled, as well as aids in temporarily anchoring the guide 620 to the bone. Alternatively, the bone probe 630 may be inserted through the drill guide bore 624 to verify the bone location.

A second bone probe (not shown) be provided for extension through a second bore (not shown) located on the other side of the drill guide bore 624. In this manner, two bone probes may be used to locate the bone in a fashion similar to the drill guides 10, 210 described above and shown in FIGS. 1–4 and 19–20.

The length of the drill guide 620 and orientation of the bore 624 are preferably such that when the shaft 616 is inserted into the bore 610 in the support member 606, a drill bit passing through the bore 624 in the block 626 will encounter the drill stop 614 on the support arm 602.

In operation, the distal end 612 of the "C" clamp 600 is inserted into the vagina of the patient and the drill stop 614 is placed alongside the bladder neck. At this time the guide arm 606 will either be extended fully, or will be removed from the "C" clamp 600 altogether. The slot 608 in the attachment member 604 is then aligned with the bore 354 in the buttock plate 306 and the threaded shaft on knob 366 is passed through the slot 608 and into the bore, at which time the support arm 602 is secured into place.

The guide arm 606 is then inserted into the bore 610 in the support arm 602, or if already in place, lowered down. The guide arm 606 is securely stationed by tightening the knobs 626 on the threaded shaft 616 until the drill guide 620 portion of the guide arm 606 is snugly against the patient: The bone probe 630 is then extended into the tissue until it contacts the bone. The bone probe 630 may also, as described above, be inserted into the drill guide bore 624 to verify the bone location. A drill bit may then be inserted into the bore 624 so as to drill a bore through the pubic bone and into the vaginal area, where the drill stop 614 will prevent the bit from further travel.

When the drill bit is removed, the bone probe 630 aids, along with the attachment to the buttock plate 306, in securely stationing the "C" clamp 600 so that it does not move. In this manner, the hole which was drilled through the tissue and bone is easily locatable by the surgeon when the drill bit has been removed. In this manner, implements such as a tube to facilitate the passage of sutures and or bone anchors can readily be directed through the hole.

EXAMPLE I

A. Patient History

The records of 30 women with SUI who were treated with modified endoscopic bladder neck suspensions consecutively by the author were reviewed. Twenty-eight patients underwent modified endoscopic bladder neck suspensions alone, while two patients had modified endoscopic bladder neck suspensions with concomitant vaginal procedures such as rectocele and/or cystocele repairs. The patients' ages ranged from 38 to 74. The grading of SUI, based on the Stamey system[2], was grade 1 in 13 patients and grade 2 in 17 patients. There were no grade 3 patients. Patients had a median of 2 vaginal deliveries. Fifty-seven percent of patients had had a previous hysterectomy. Twenty percent of patients had had at least one previous surgical procedure to correct urinary incontinence.

All patients had a history demonstrating bothersome urinary leakage with activities and physical examination demonstrating a hypermobile urethra and pliable pubocervical fascia. Complaints preoperatively included urgency in 63% and urgency incontinence in 40% of patients. Preoperative testing in all patients included 1) a Marshall test that demonstrated leakage with coughing and one finger control of leakage with bladder neck elevation and 2) a cystometrogram that did not demonstrate uninhibited contractions.

B. Technique

All patients received gentamicin and ampicillin preoperatively unless an allergy existed. Anesthesia was regional in 16 patients and general in 14 patients. A surgical assistant was not used. The patients were placed in the lithotomy position. Preparation emphasized isolation of the anus with a stapled towel or plastic drape. A Foley catheter was passed.

Figure 8:
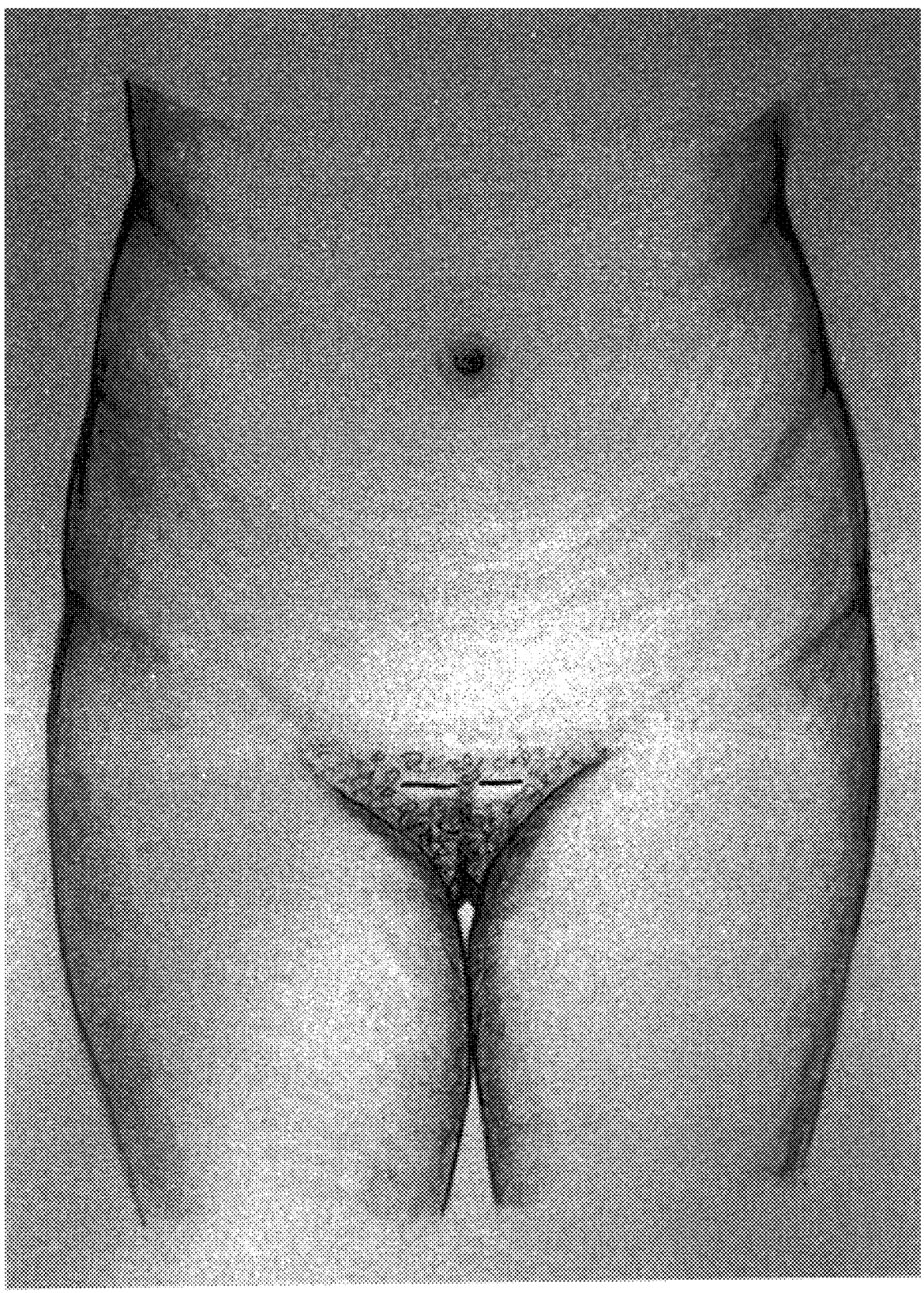
FIG. 8 illustrates the location of incision sites for the method of the present invention.
Figure 9A:
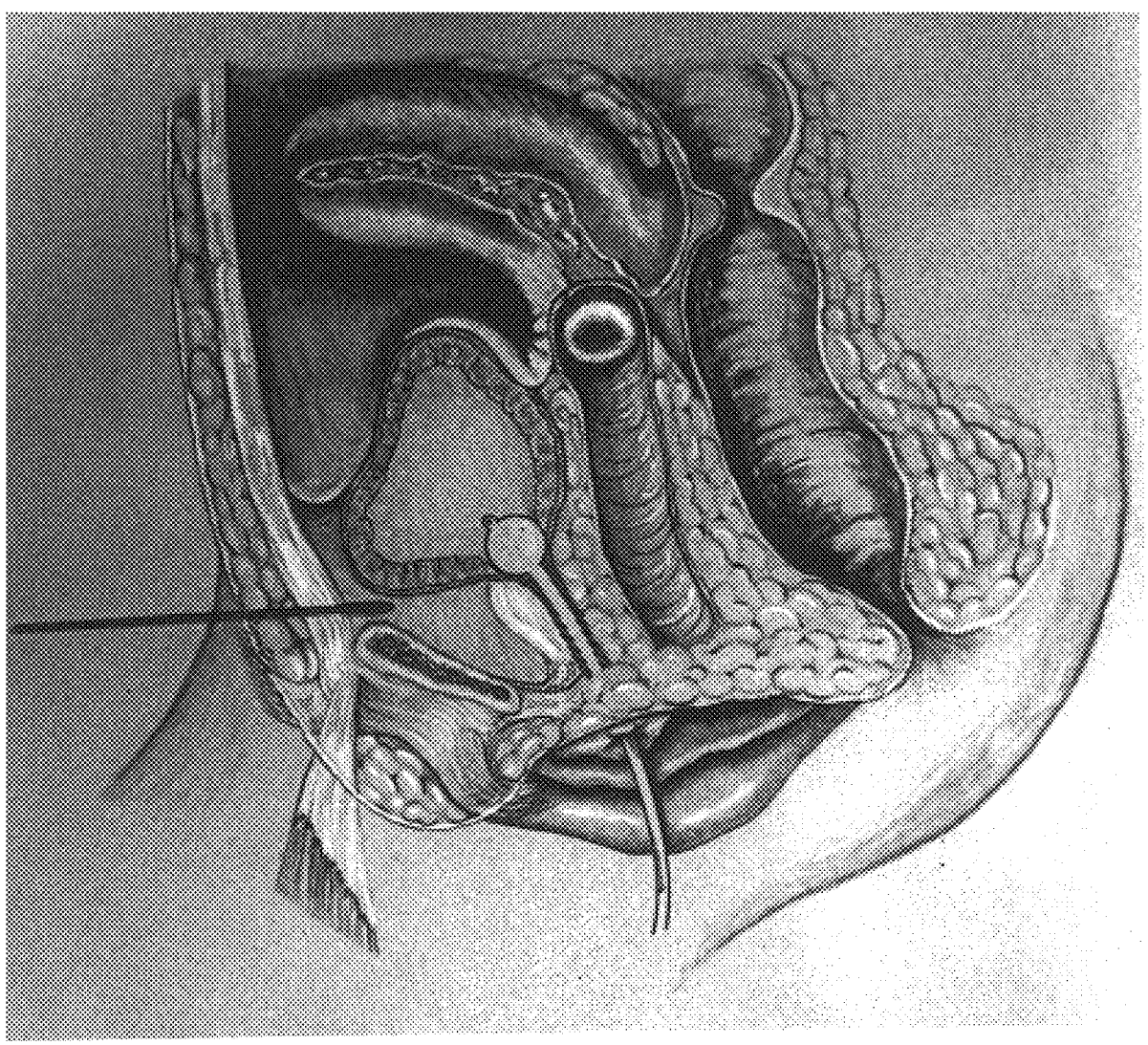
FIG. 9a represents the positioning of the vertical passage of a Stamey needle to just below the rectus fascia.
Figure 9B:
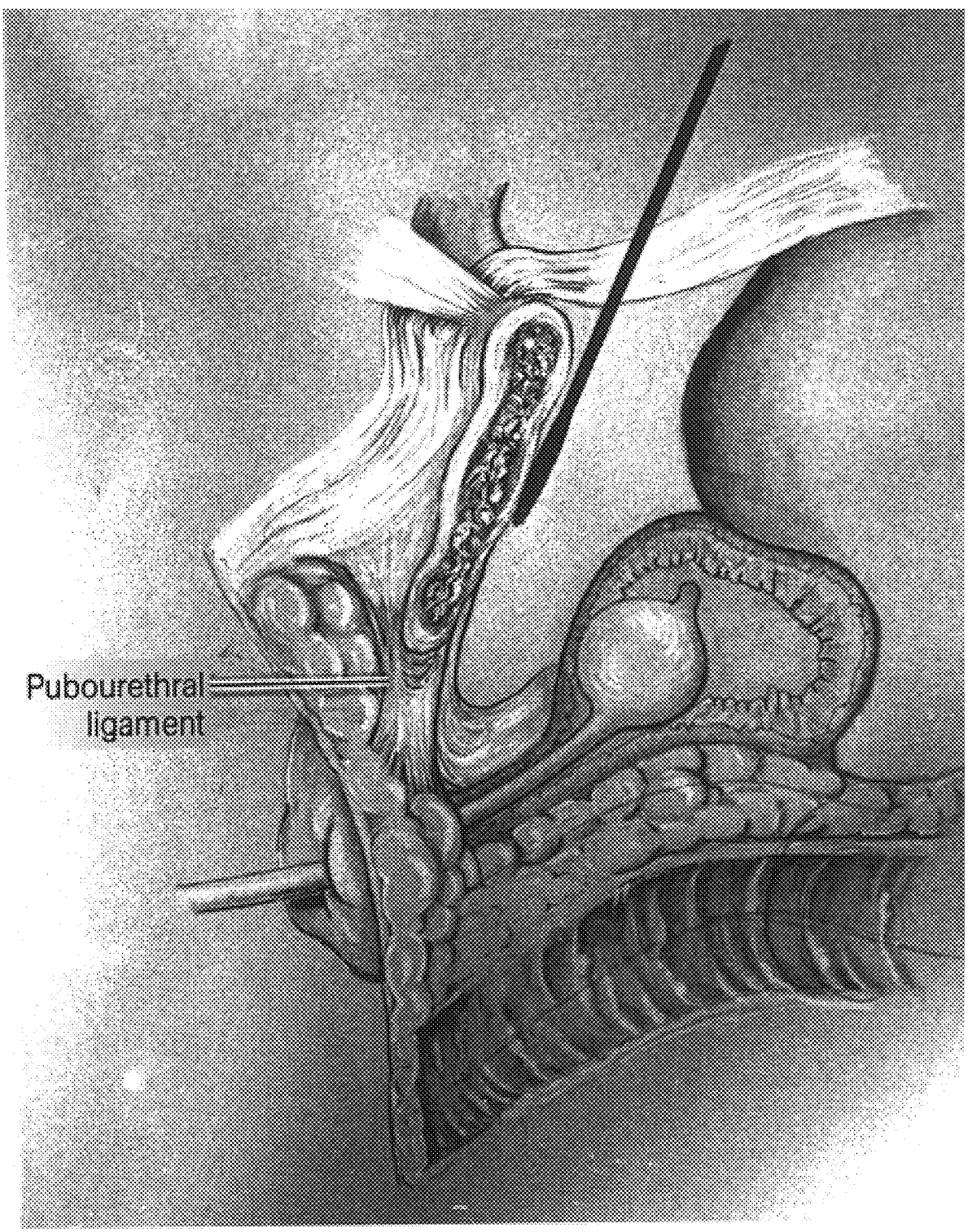
FIG. 9b illustrates the placement of a needle point on the underside of the pubic bone.

Two separated, one inch transverse incisions were made over the pubic bone (FIG. 8) and dissection was carried down to the area of the rectus fascia. Beginning on the right side, the wound was stretched cephalad to allow the vertical passage of a Stamey needle (Pilling Company, Fort Washington, Pa.) through the rectus fascia (FIG. 9A). The needle was then sharply angled onto the abdomen so that the point rested on the underside of the pubic periosteum (FIG. 9B).

Figure 9C:
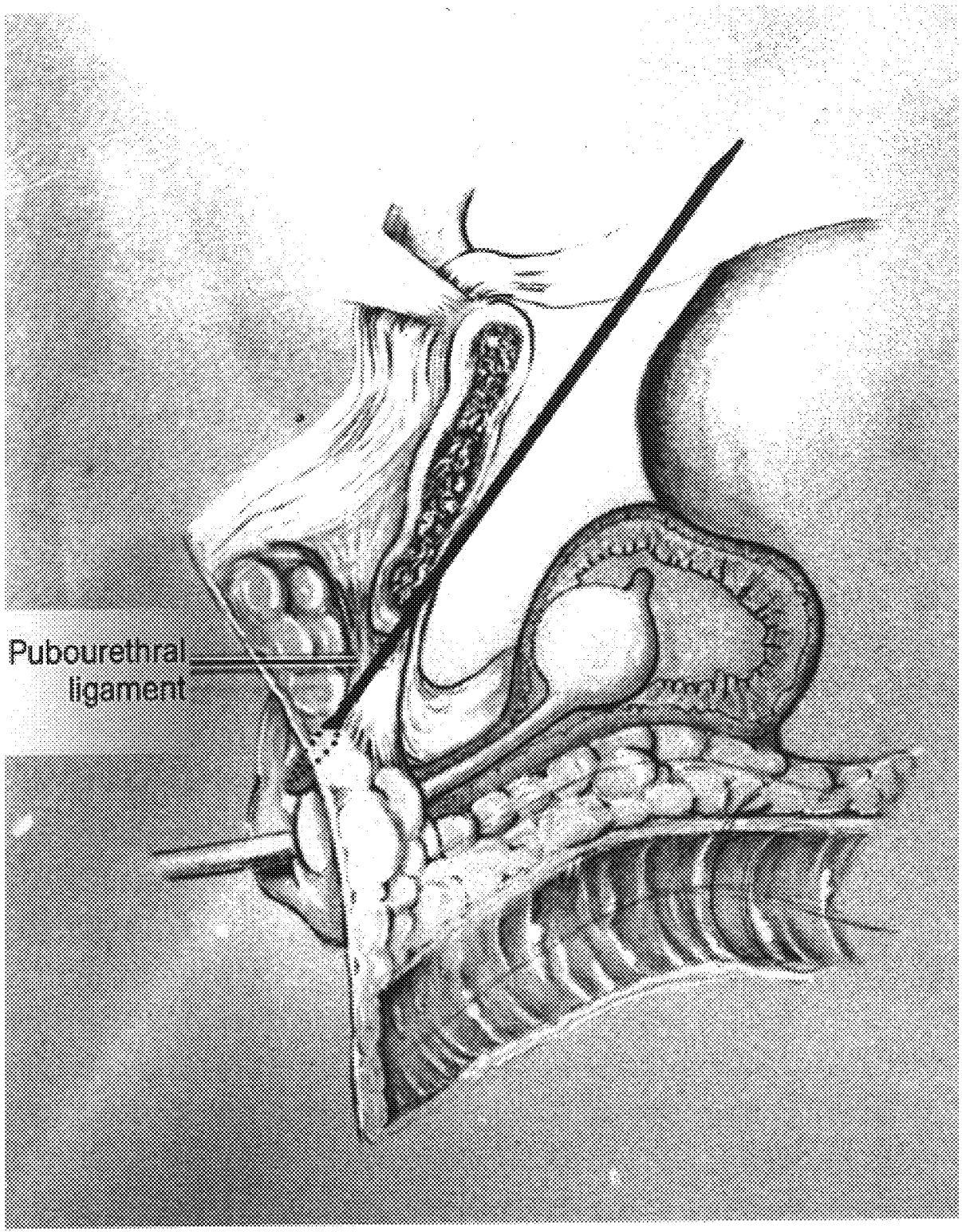
FIG. 9c represents the distal passage of the needle to the level of the introitus.
Figure 9D:
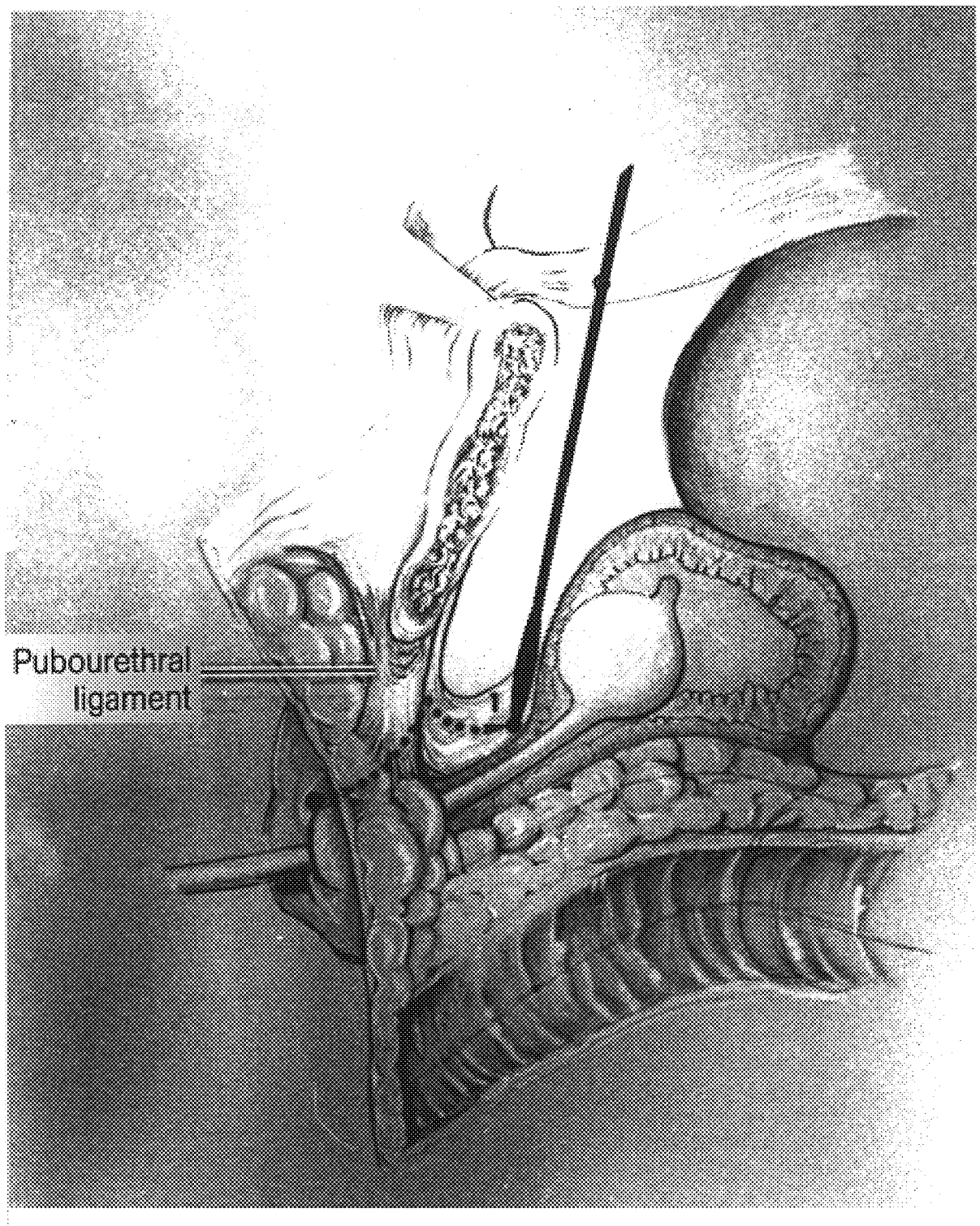
FIG. 9d represents the withdrawal of the needle from the pubourethral ligament and the path of the sweep back along the pubocervical fascia to the area of the bladder neck and first entry site.

The point of the needle, while maintaining contact with the underside of the pubis, was thereafter passed distally toward the introitus. At the completion of this distal passage,. the needle could be palpated through the introitus to the right of the urethra (FIG. 9C). Palpation through the vagina was avoided during this distal passage of the needle to avoid pushing the bladder or urethra into the path of the needle. The tip of the needle was withdrawn from the pubourethral ligament and gently swept along the pubocervical fascia to the area of the bladder neck (FIG. 9D) under the guidance of a finger within the vagina.

Figure 10A:
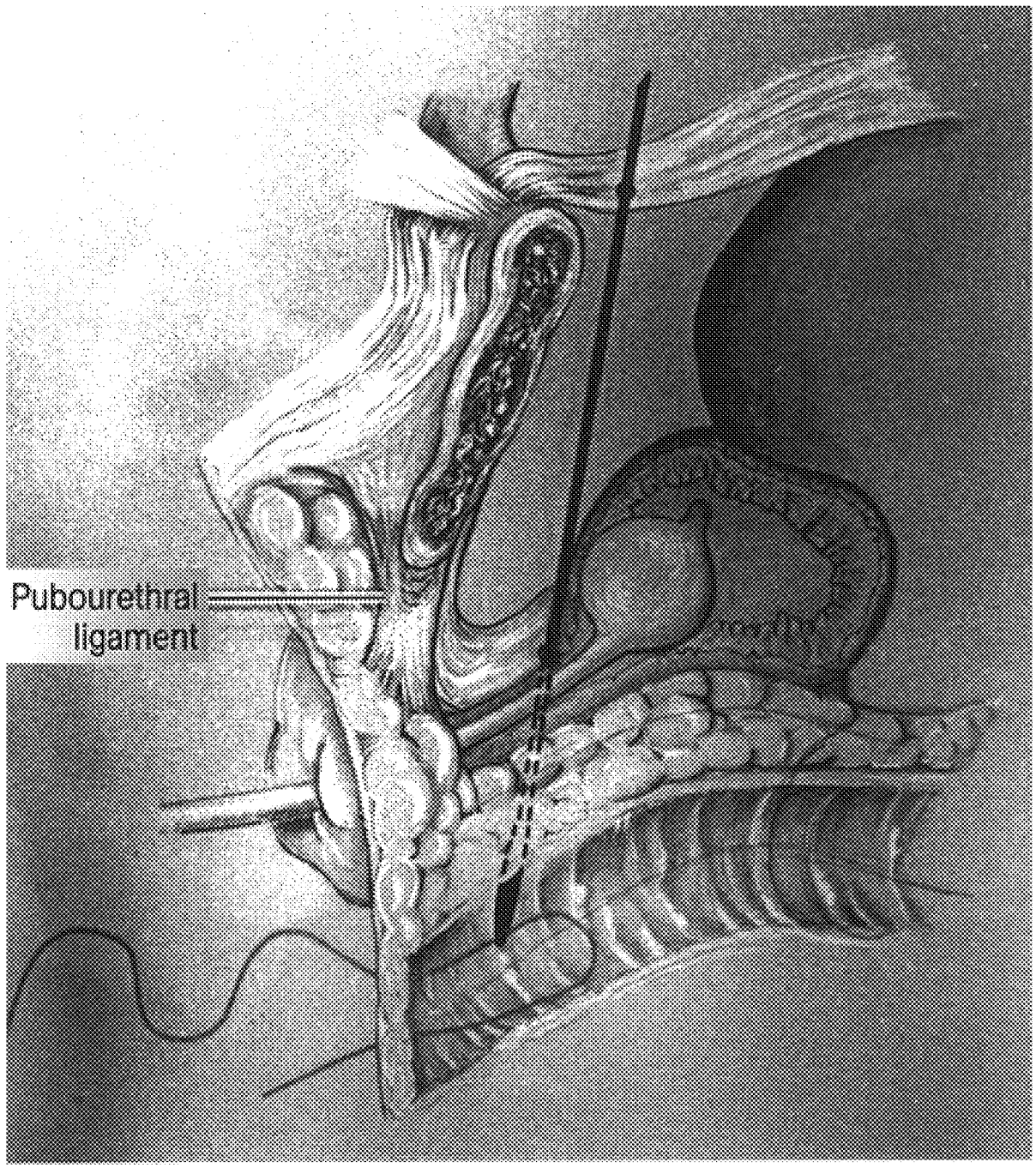
FIG. 10a illustrates the initial passage of the needle through the pubocervical fascia at point 1 (proximal and medial).
Figure 10B:
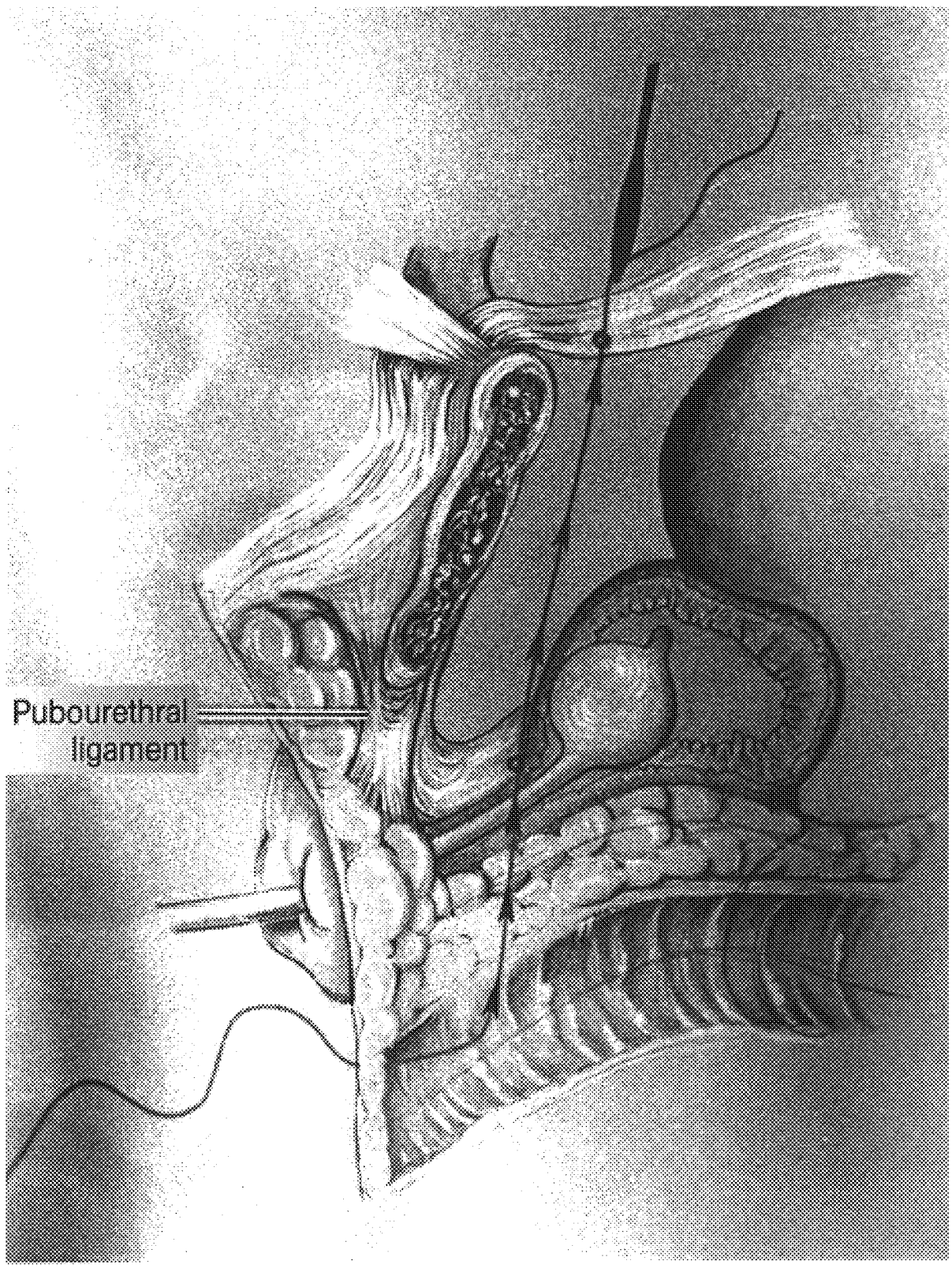
FIG. 10b represents the withdrawal of the suture through the pubic wound.
Figure 10C:
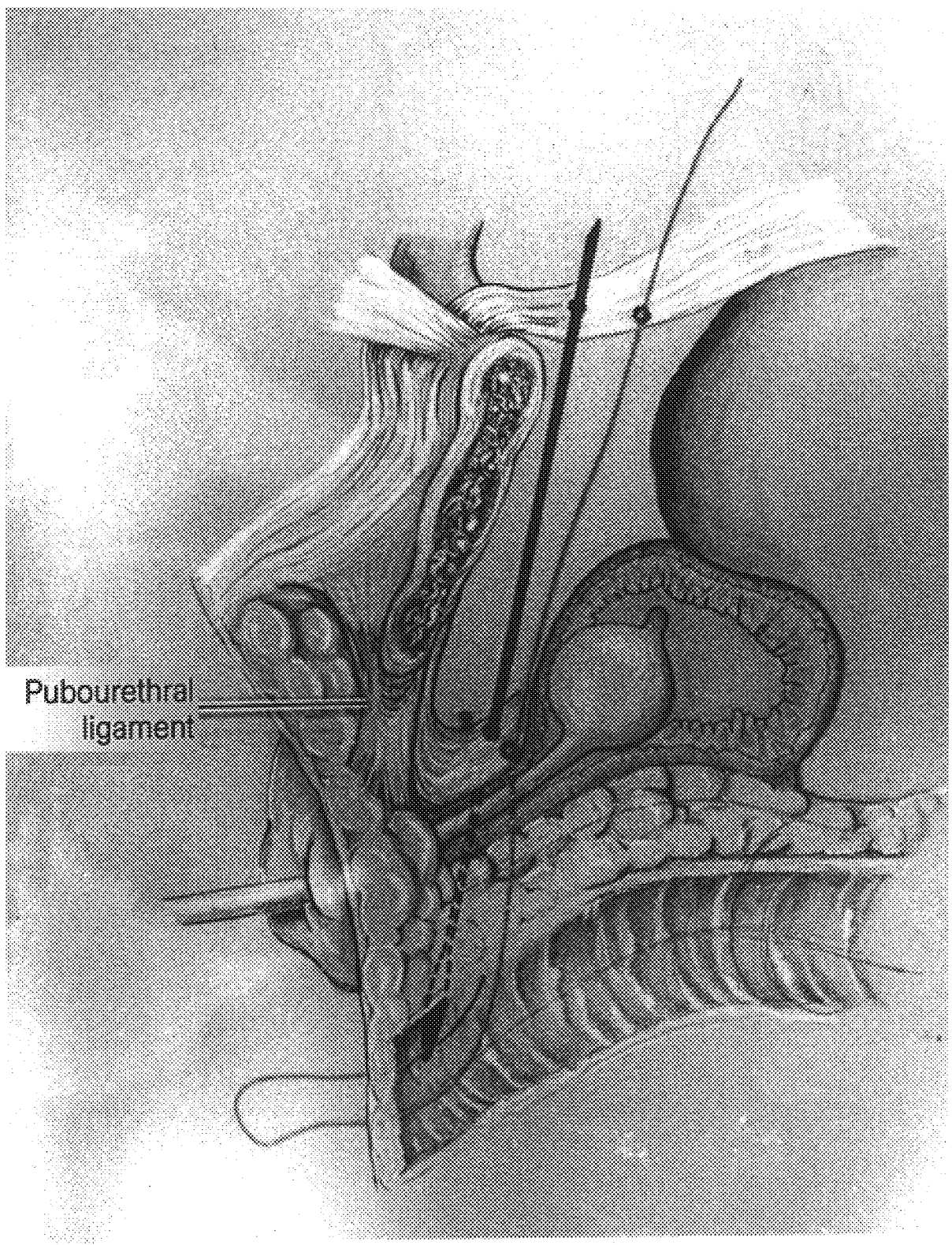
FIG. 10c illustrates the passage of the needle through the lateral aspect of the pubic wound and through the pubocervical fascia at point 2 (proximal and lateral).
Figure 10D:
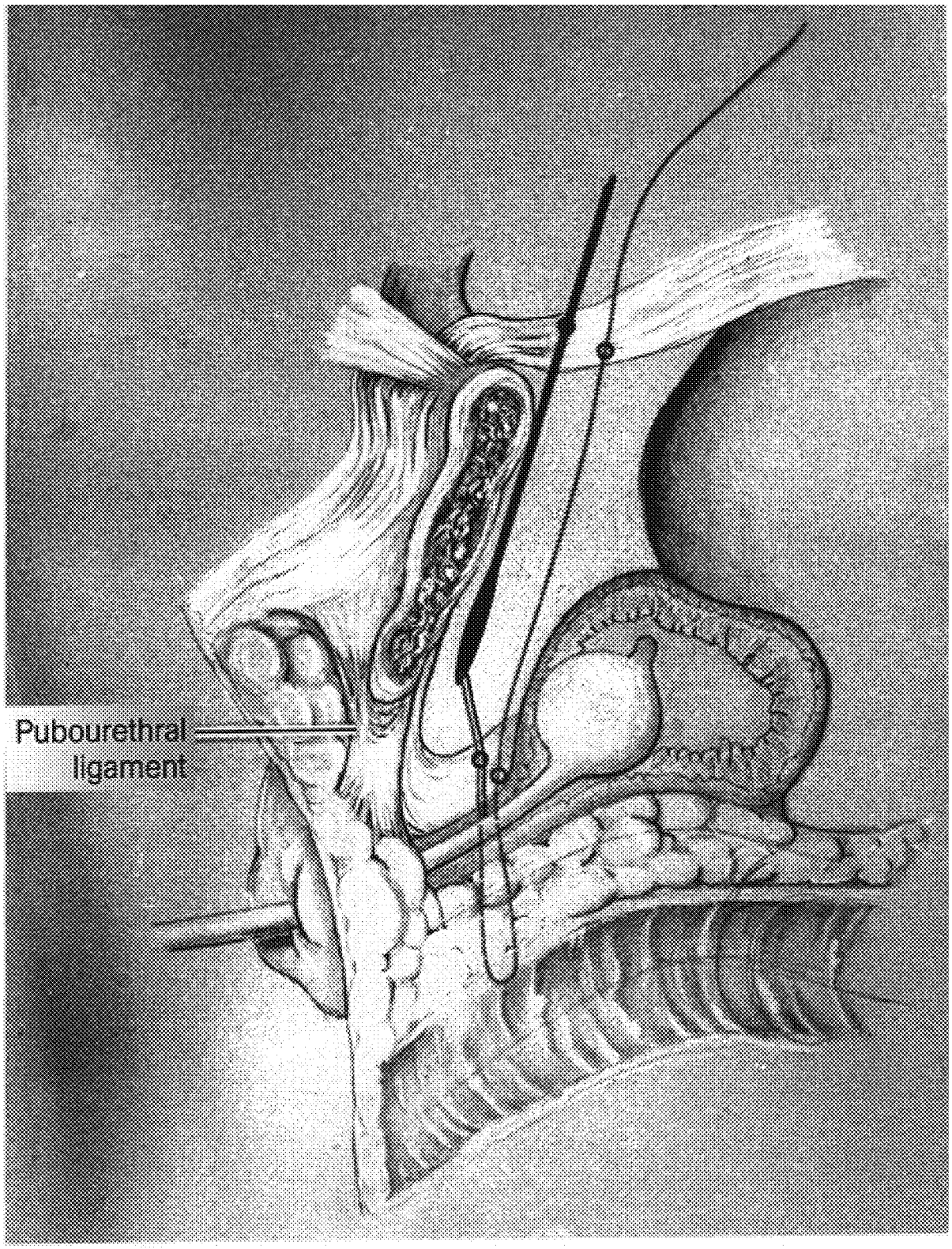
FIG. 10d illustrates the withdrawal of the suture into the retropubic space.
Figure 10E:
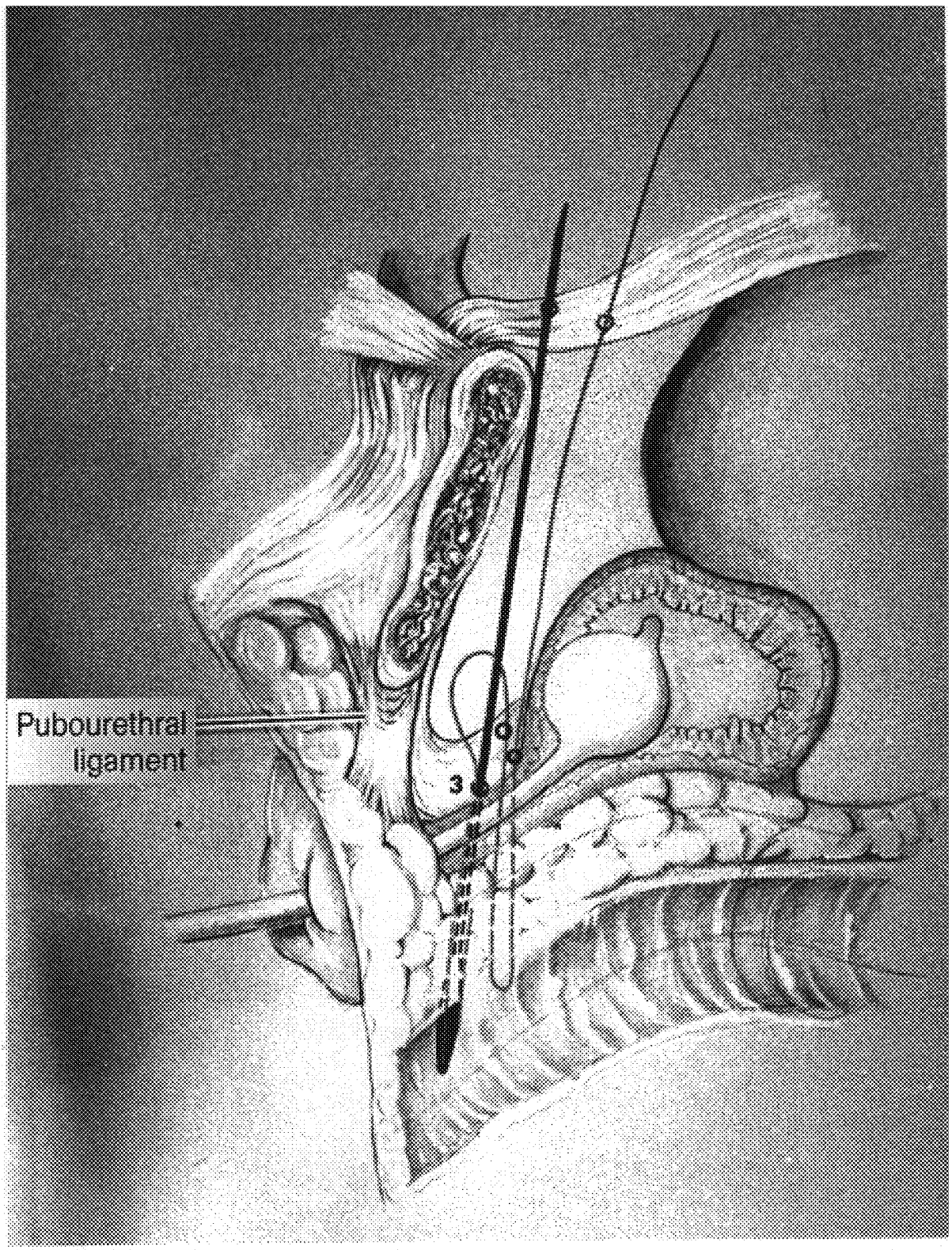
FIG. 10e illustrates the passage of the needle and suture through point 3 (distal and medial).

The needle was then passed through the pubocervical fascia and vaginal mucosa at point 1 (FIG. 10A). A number 1 polypropylene suture was passed through the needle hole and withdrawn with the needle through the pubic wound (FIG. 10B). The needle was then reintroduced through the rectus fascia 2 cm. lateral to the initial passage and through the vaginal mucosa at point 2 (FIG. 10C) using the same needle passage technique described above (FIG. 9A–D). The tip of the needle with the vaginal end of the suture was then withdrawn into the retropubic space (FIG. 10D) and then advanced to point 3 where it was passed through the vaginal mucosa and passed distal to the introitus (FIG. 10E).

Figure 10F:
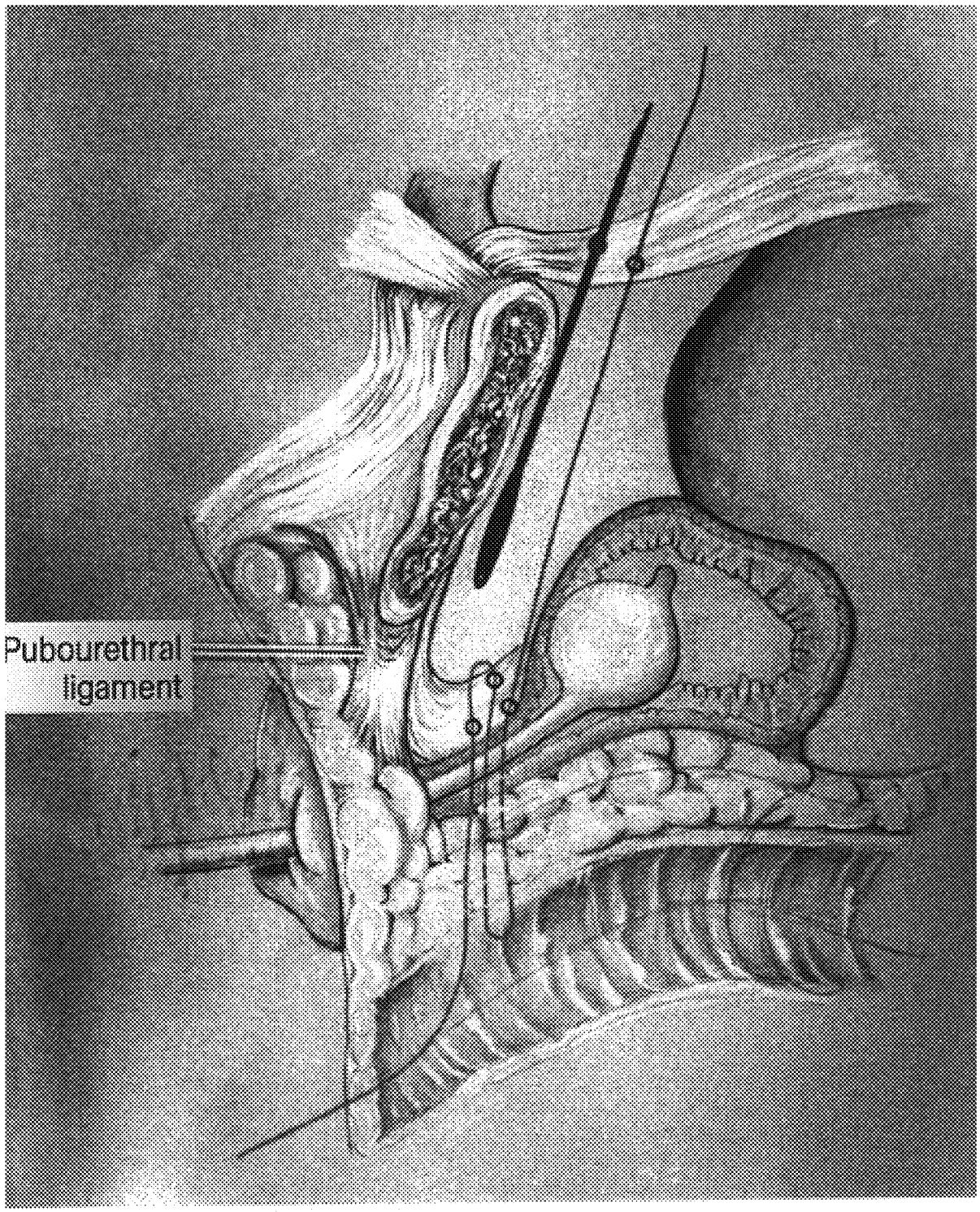
FIG. 10f illustrates withdrawal of the needle into the retropubic space.
Figure 10G:
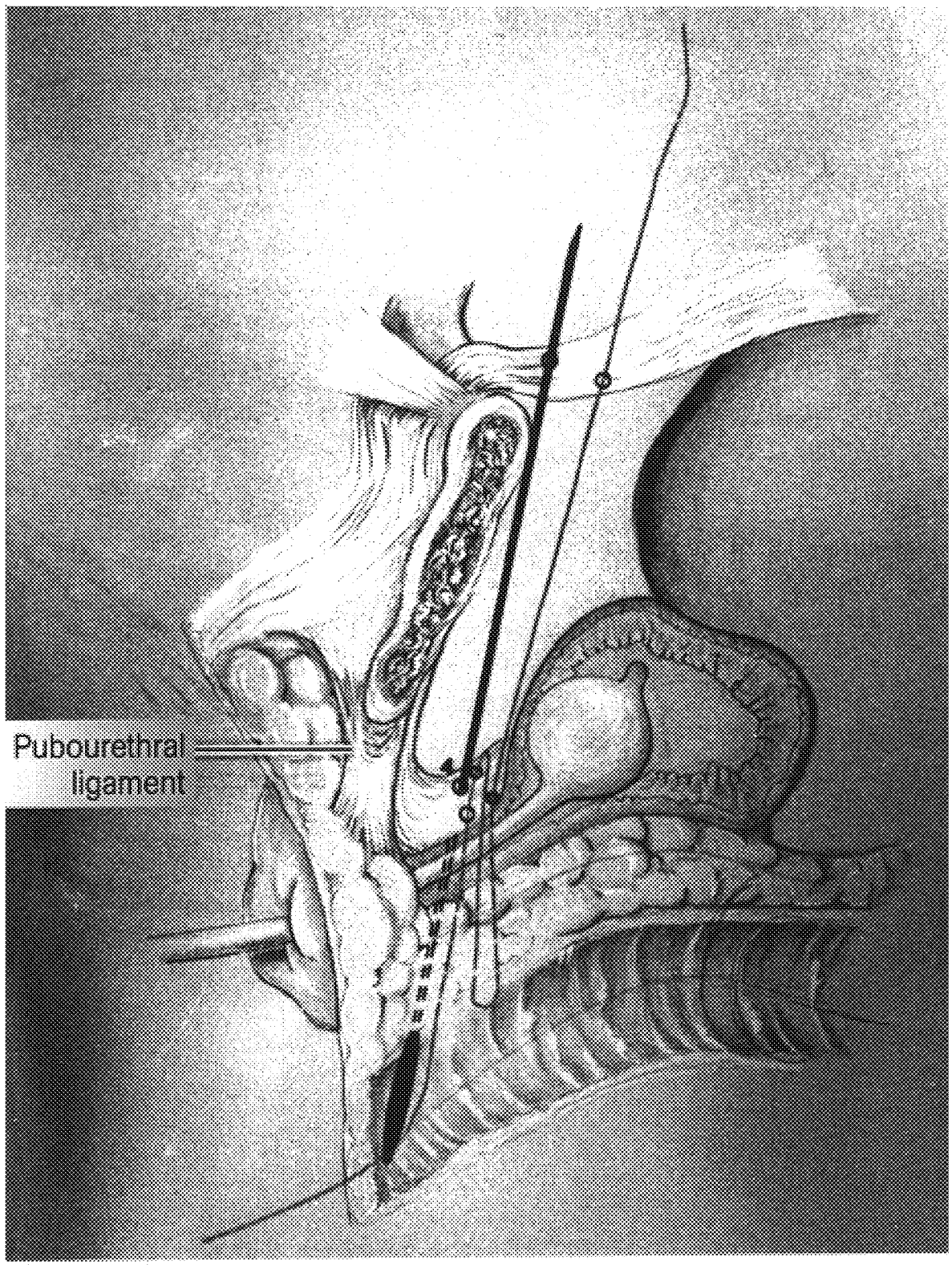
FIG. 10g illustrates the passage of the needle through point 4 (distal and lateral).
Figure 10H:
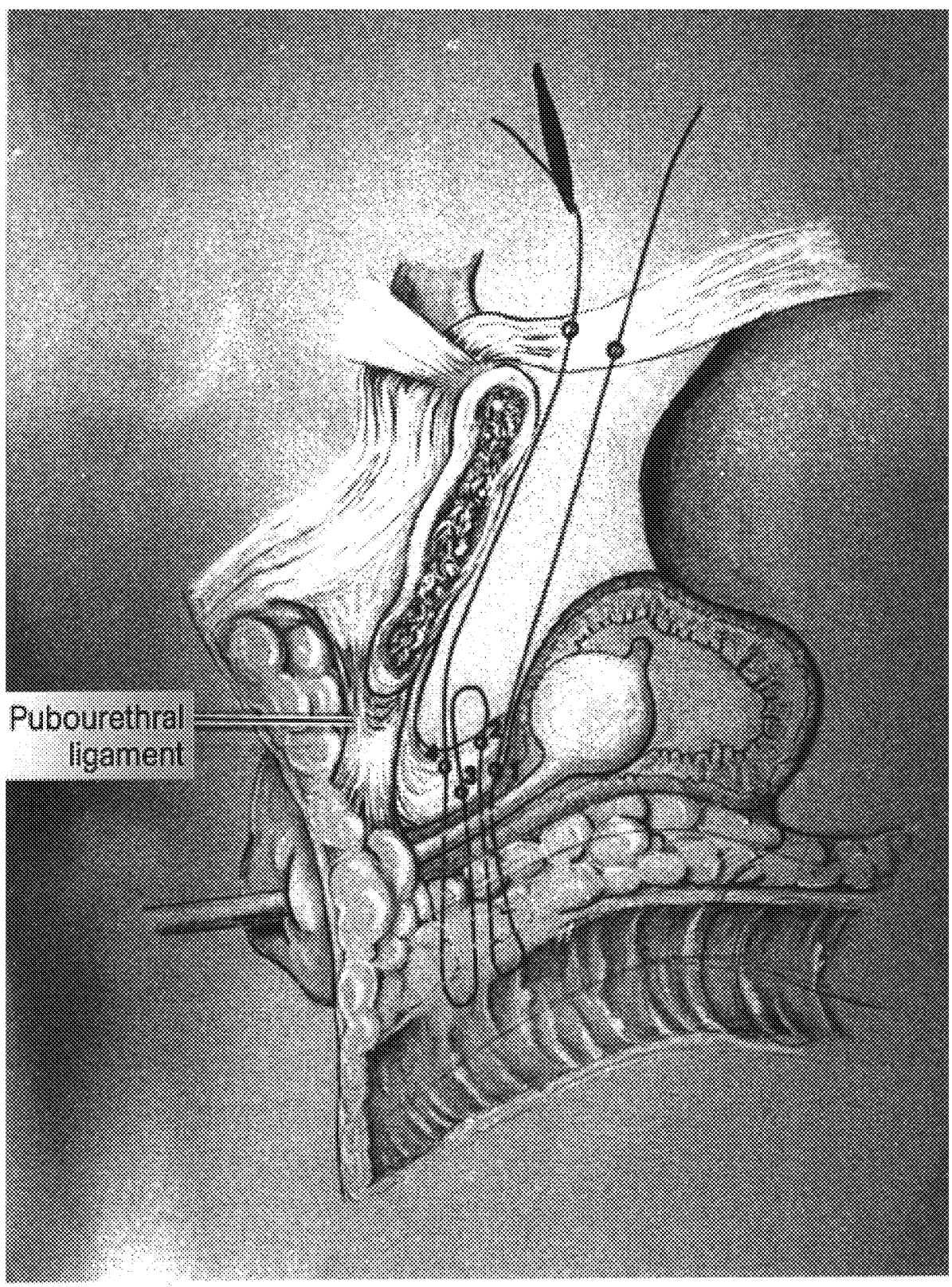
FIG. 10h illustrates the withdrawal of the suture through the pubic wound.

The suture was then removed from the needle and the needle tip was once again withdrawn to the retropubic space (FIG. 10F) and passed through the vaginal mucosa at point 4 (FIG. 10G). The vaginal end of the suture was then passed into the needle and pulled up through the pubic wound using the needle (FIG. 10H). An attempt was made with the 4 entry points through the pubocervical fascia to maximize 1) their separation (approximately 2 cm. apart), and 2) their laterialization from the bladder neck and urethra (approximately 2 cm. away) (FIG. 13A).

The identical procedure was performed on the left side. Direct or video cystoscopic confirmation of suture position was performed on the left side. Direct or video cystoscopic confirmation of suture position was performed with special attention to avoid handling the contaminated eyepiece of the cystoscope (when video cystoscopy was not done).

Figure 11B:
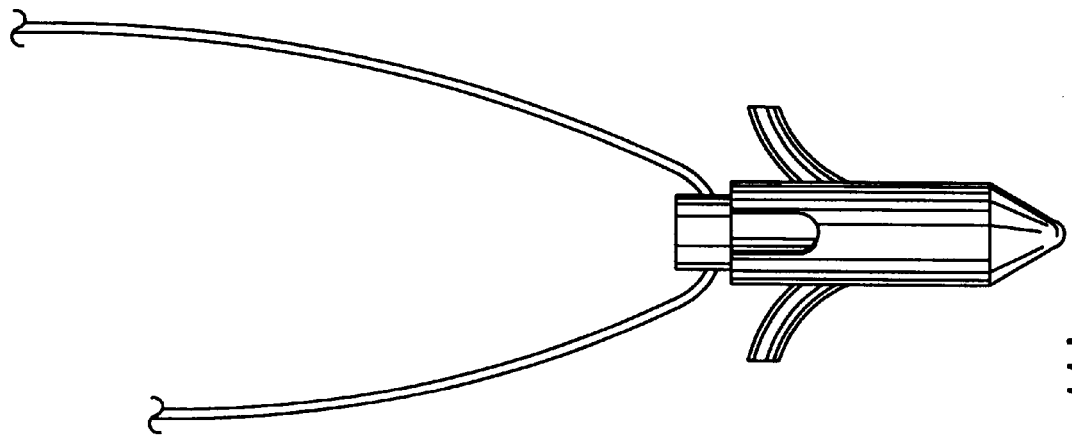
FIG. 11b illustrates a Mitek G2 anchor.
Figure 11A:
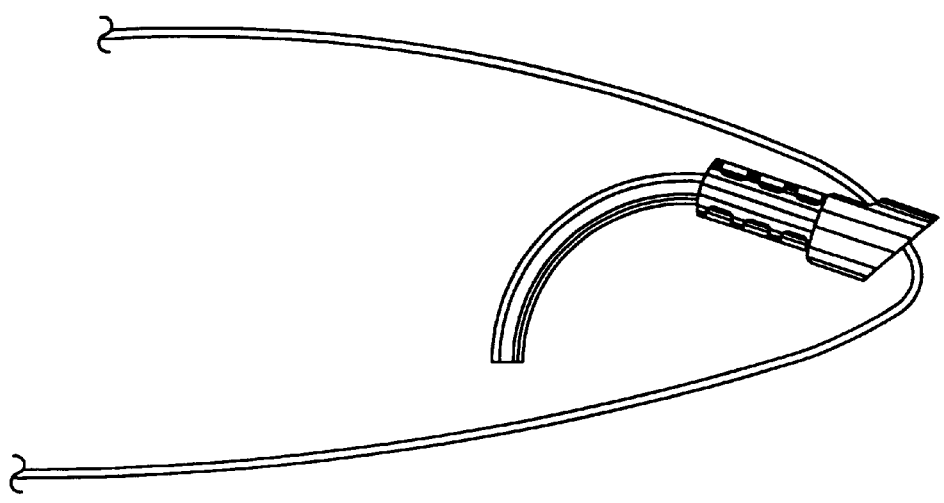
FIG. 11a illustrates an early generation Mitek G1 anchor.
Figure 12A:
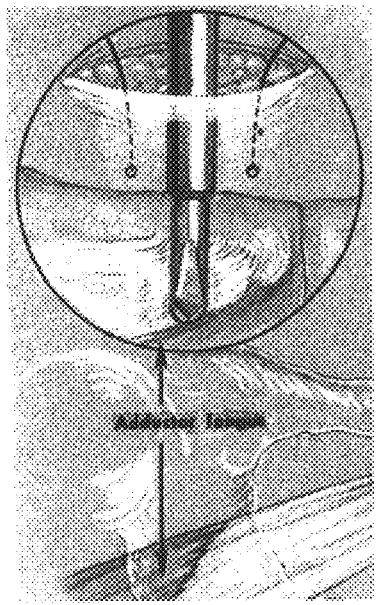
FIG. 12a illustrates drilling a hole in the pubic bone for placement of an anchor.
Figure 12B:
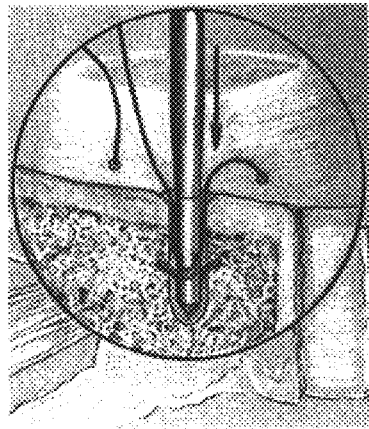
FIG. 12b illustrates placement of an anchor with a suture into the pubic bone using an anchor inserter.
Figure 12C:
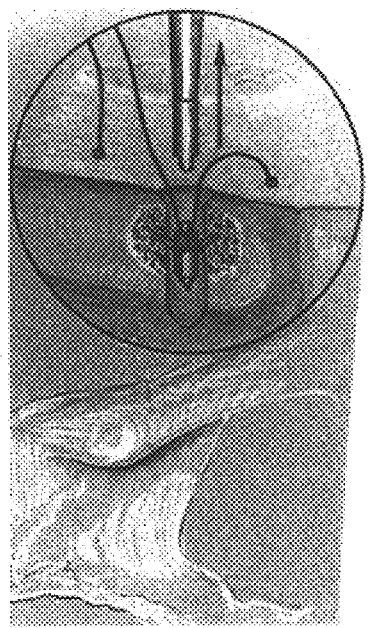
FIG. 12c illustrates extraction of the inserter leaving an anchor and suture in place.

The Mitek Anchor System (Mitek Surgical Products, Inc., Northwood, Mass.) was then used in all patients for pubic bone fixation of the suspensory sutures. Mitek G1 anchors (FIG. 11A) were used in the first seven patients and the newer Mitek G2 anchors (FIG. 11B) were used in the remaining 23 patients. Two holes were drilled into the pubic bone approximately 2 cm. lateral to the symphysis (FIG. 12A). One anchor for each side (2 per patient) was loaded with a medical suture end (which had had less vaginal contact than the lateral ends, thereby, potentially reducing the chance of bacterial contamination). Each anchor was placed into its hole using an inserter (FIG. 12B). The inserter was extracted leaving each anchor in place (FIG. 12C). Traction was placed on the sutures to assure adequate fixation of the anchors.

Figure 13A:
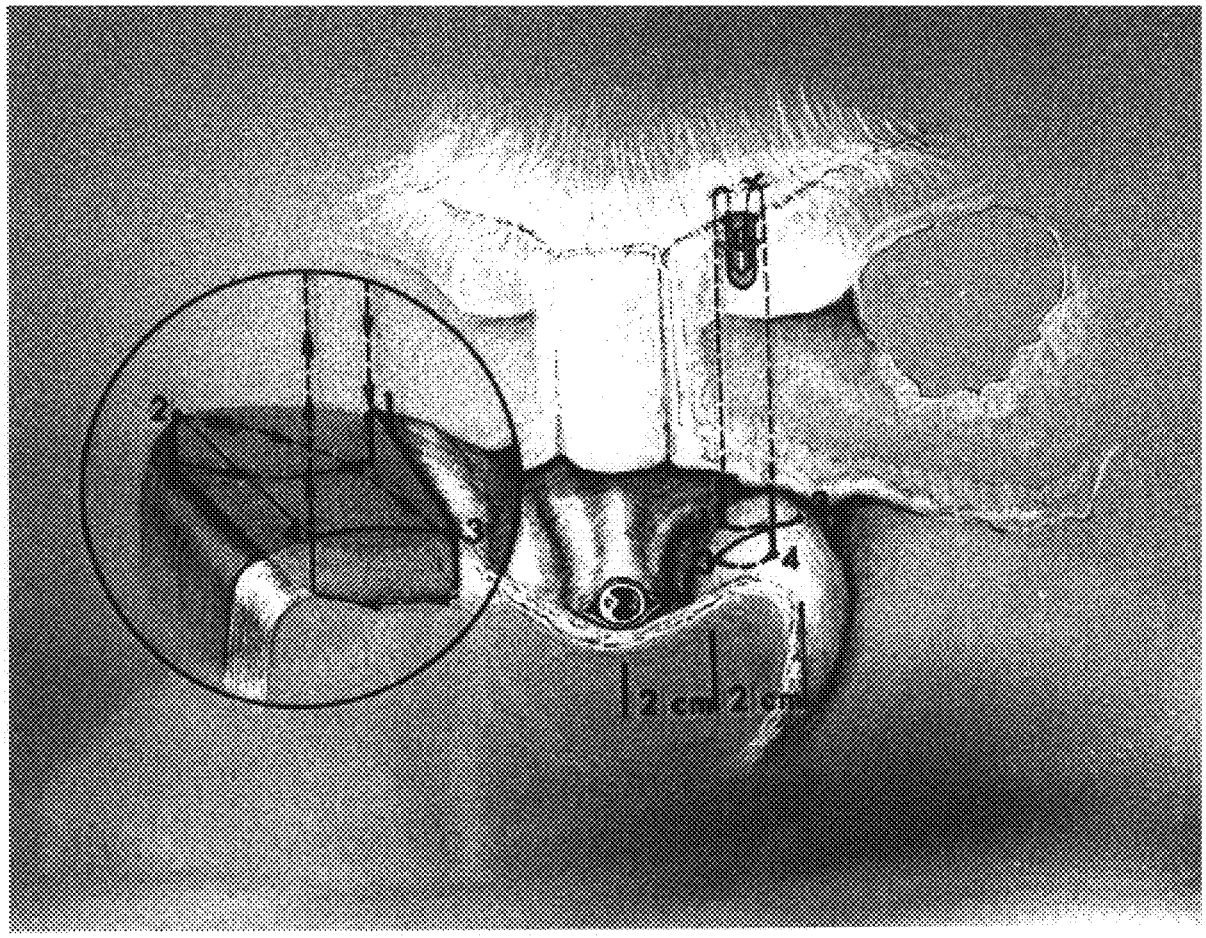
FIG. 13a is an end-on view of the urethra emphasizing volume of pubocervical fascia captured and showing relative locations of suture entry points.
Figure 13B:
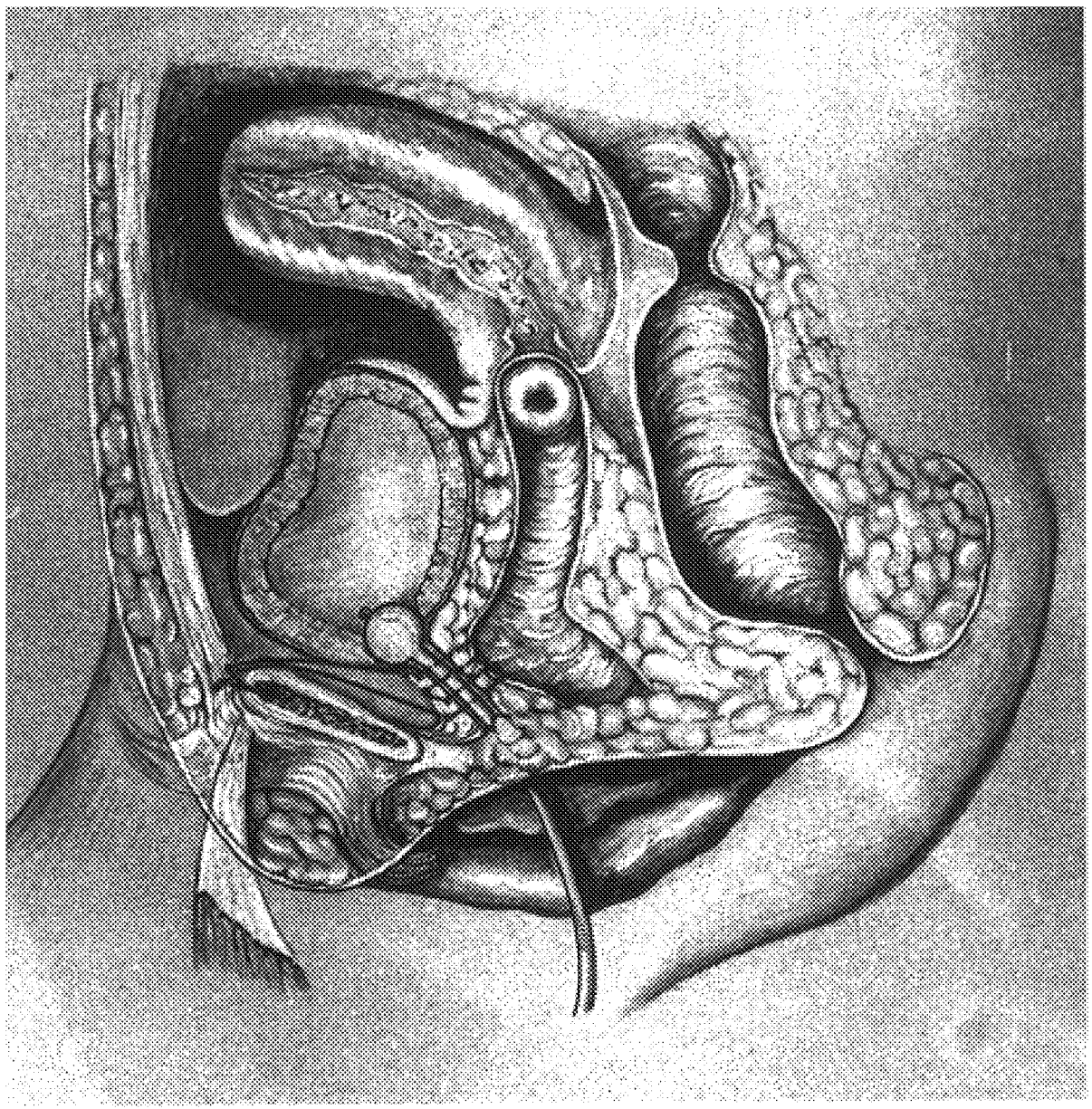
FIG. 13b is a lateral view emphasizing the length of pubocervical fascia captured from the bladder neck to the pubourethral ligament.
Figure 14:
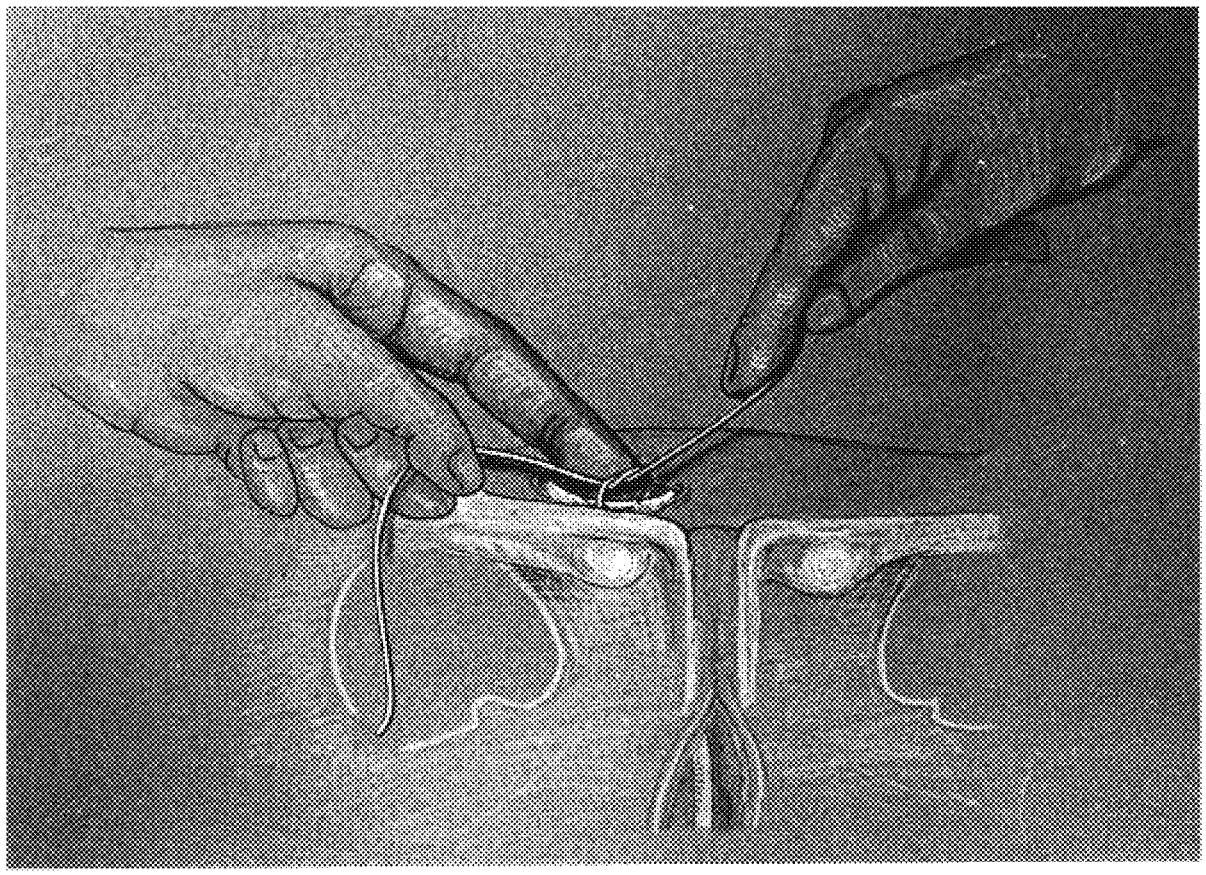
FIG. 14 illustrates the tying of the suspension suture on pulp of finger leaving a small amount of suture slack.

The sutures on each side were then tied down with sufficient tension so as to develop a gentle elevation and cradle-like support of the bladder neck (FIG. 13A and 13B). A modification to limit and control the tension on the suspending suture web in a reproducible manner was instituted in the last 17 patients within the study. The sutures in these patients were tied down snugly on the distal pulp of the index finger (FIG. 14).

The wounds were irrigated with a bacitracin solution. The wound edges and the rectus fascia at the suture entry points were infiltrated with bupivacaine. A Foley catheter was placed in 80% of the patients. The remaining patients had a suprapubic tube placed because of the dexterity problems or their aversion to learning intermittent catheterization.

Following surgery, patients were given either ciprofloxacin or ofloxacin for 10 days. The patients' Foley catheters were removed one week following surgery. The patients performed intermittent catheterization as necessary until the post-void residuals were less than 75 cc. on two consecutive catheterization. Patients with suprapubic tubes generally began voiding trials at 4 days following surgery. The suprapubic tubes were removed when the post-void residuals were less than 75 cc. following two consecutive urinations.

C. Results

Figure 15:
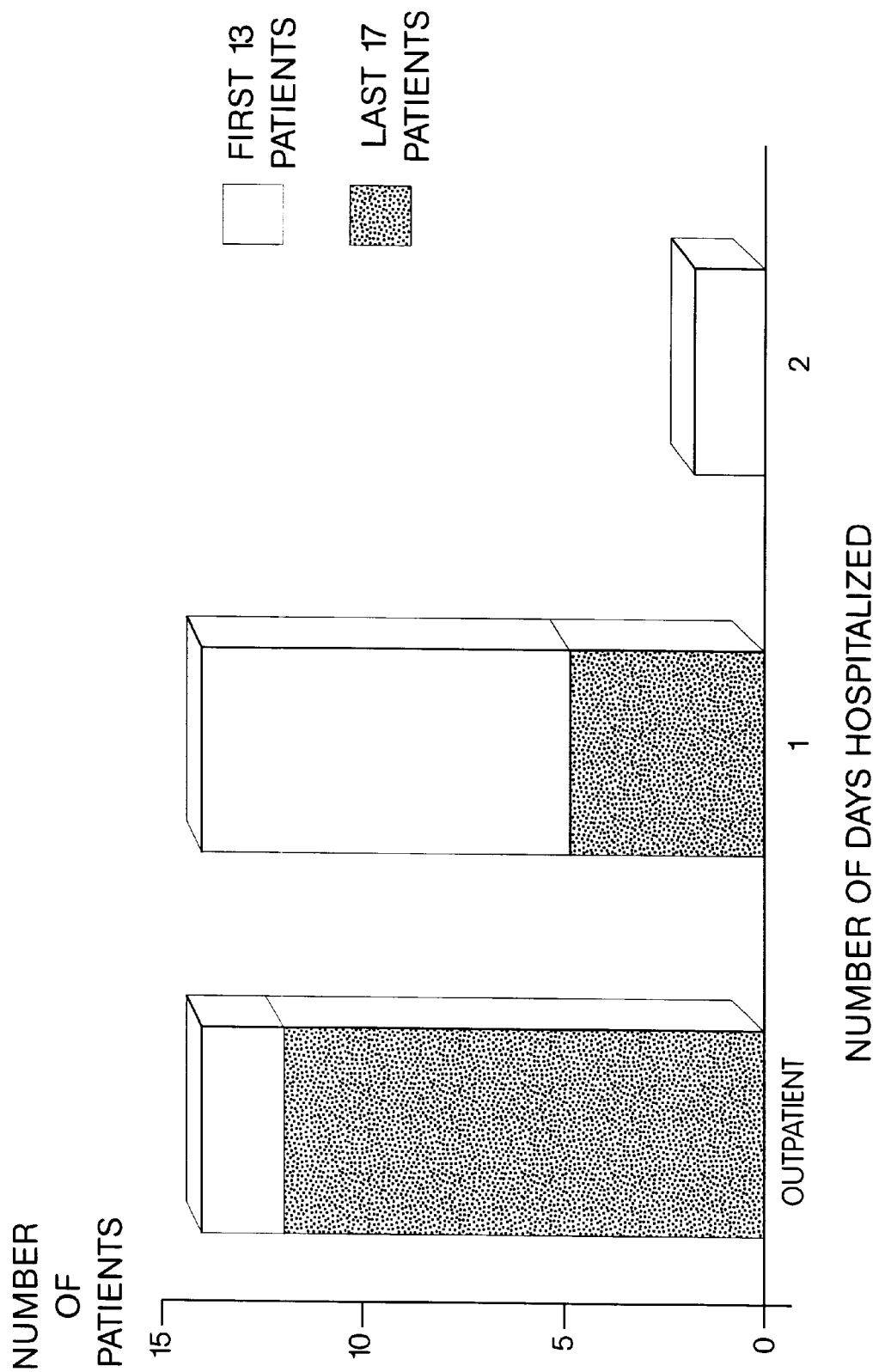
FIG. 15 illustrates the duration of hospitalization following surgery of the patients discussed in Example 1.
Figure 16:
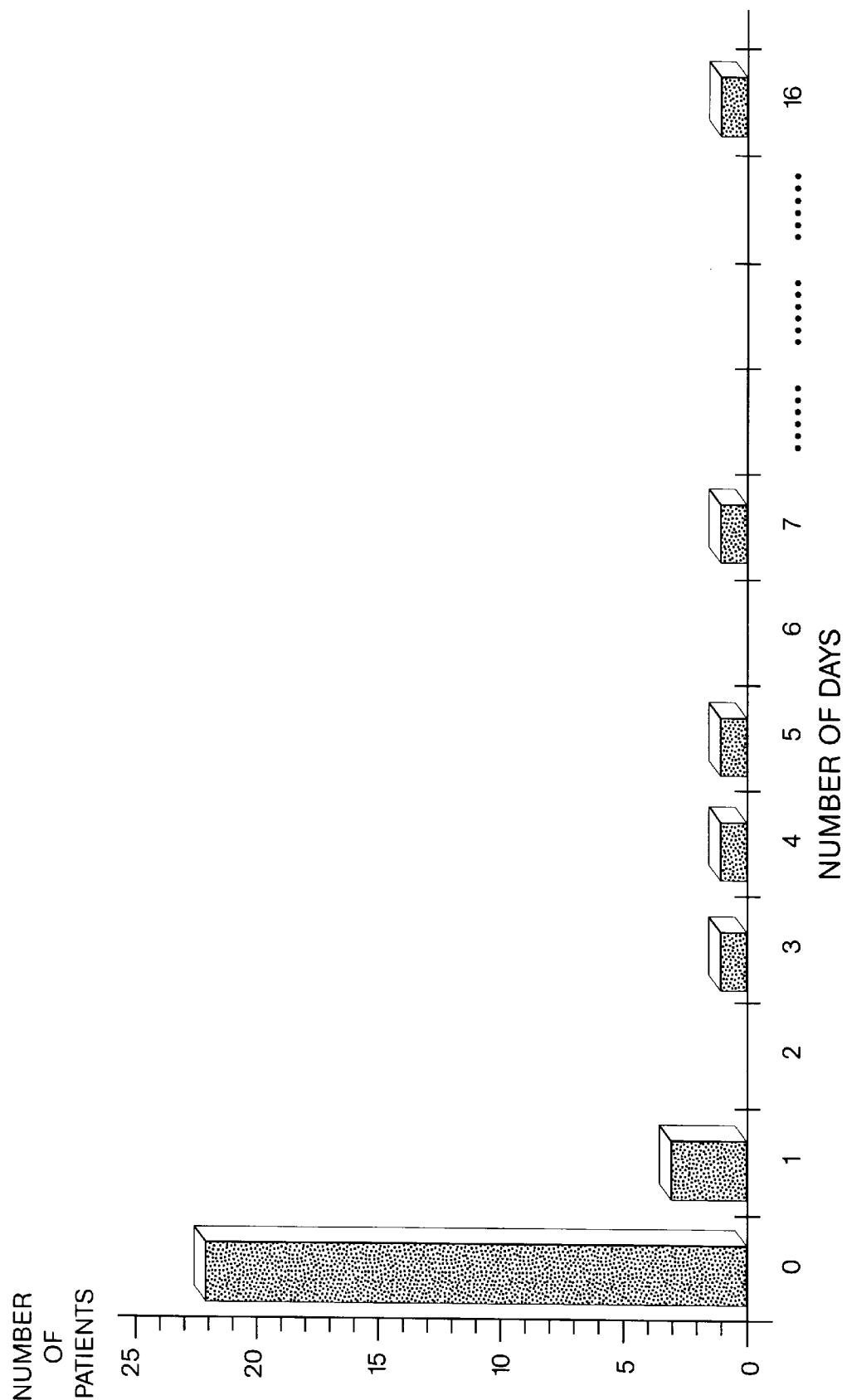
FIG. 16 illustrates the period of intermittent catheterization following removal of in-dwelling catheter for the patients discussed in Example 1.
Figure 17:
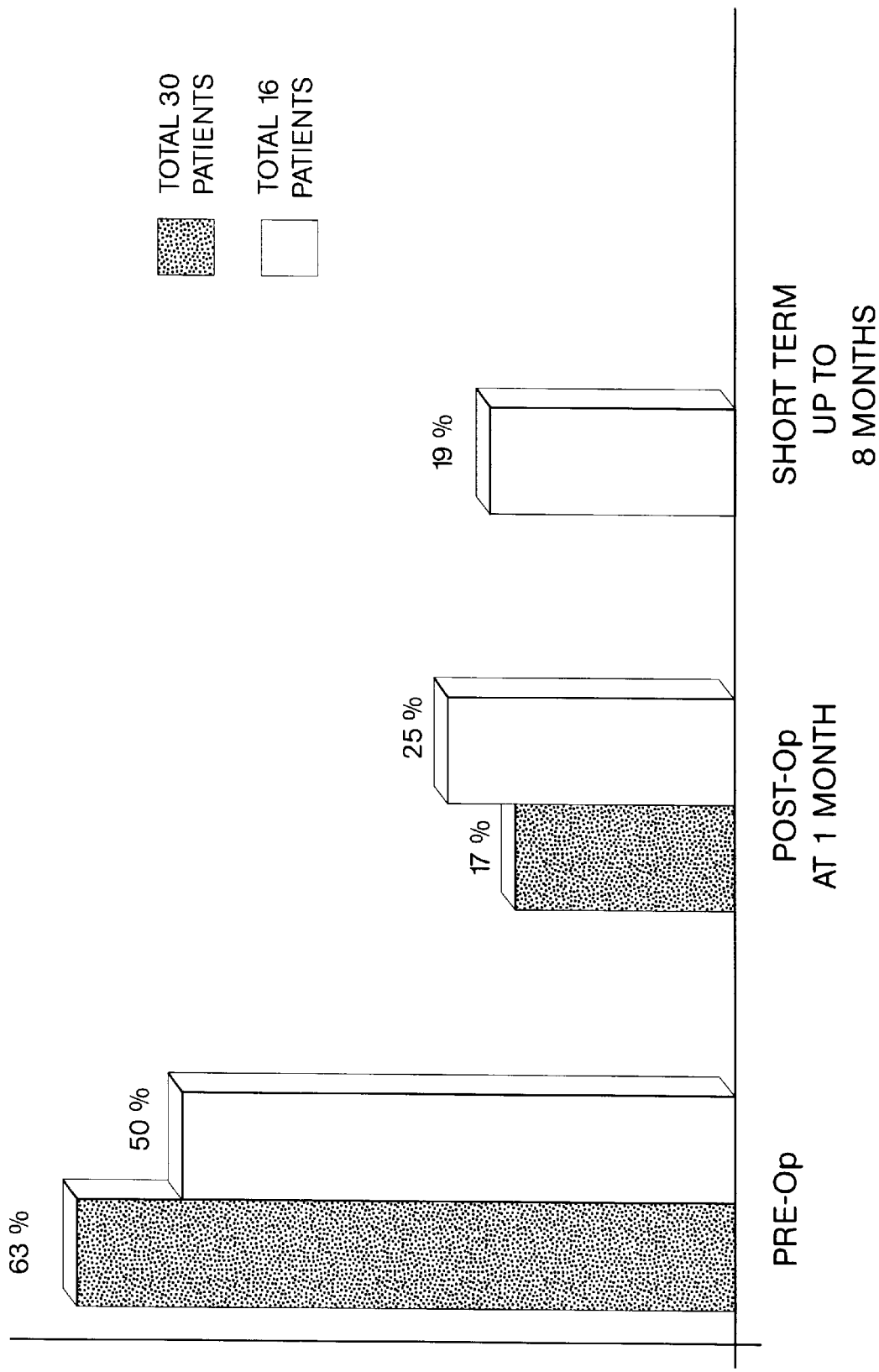
FIG. 17 illustrates urinary urgency before and after surgery for the patients discussed in Example 1.
Figure 18:
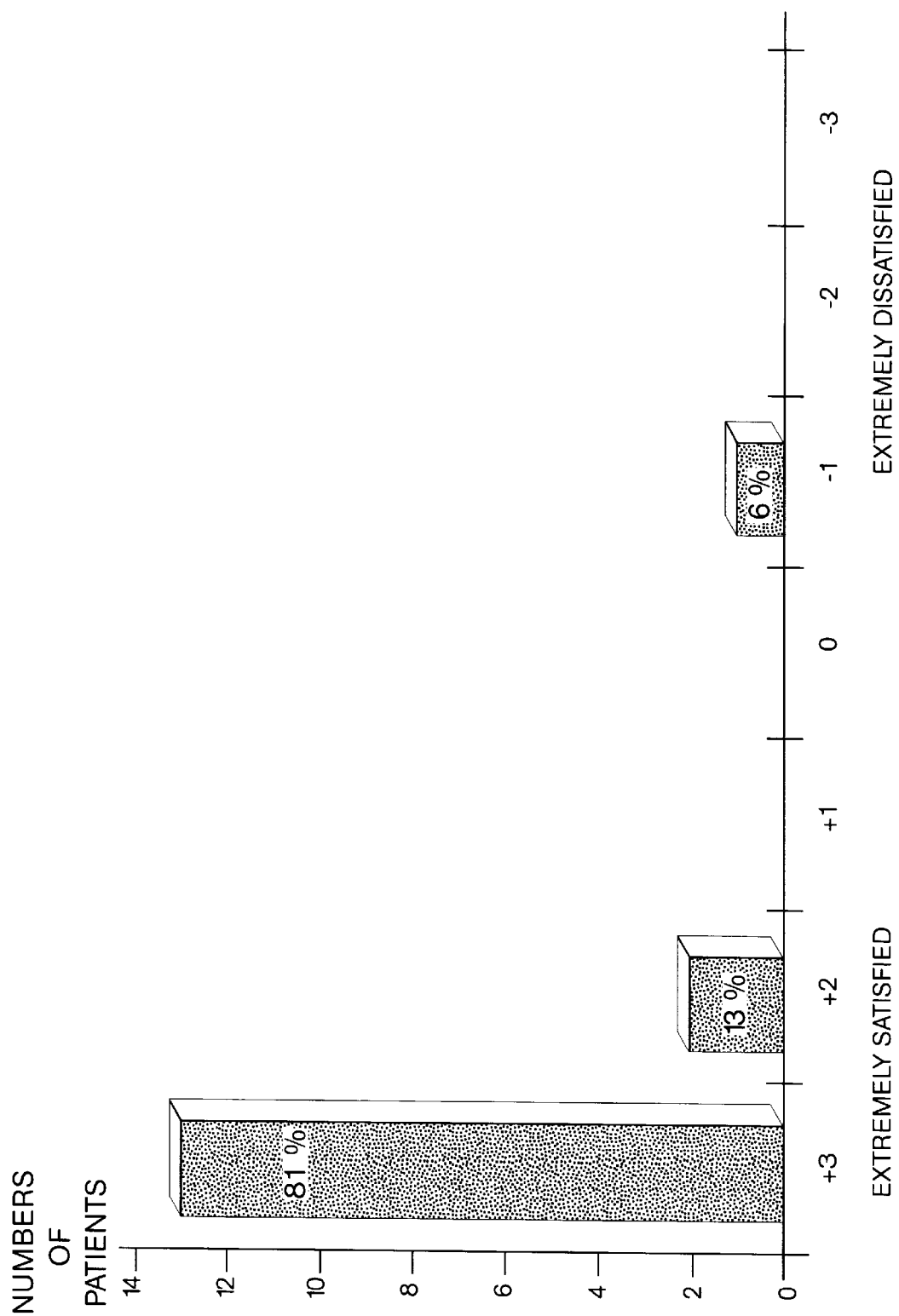
FIG. 18 illustrates patient subjective satisfaction with results of the procedure conducted in accordance with the present invention, for patients discusses in Example 1.

All 30 women who underwent this procedure were evaluated within the first month post-operatively ("post-op" followup). The initial 16 consecutive patients of this group were evaluated up to eight months after surgery by mail questionnaires ("short-term" follow-up). Three patients who did not return their questionnaires were contacted by phone. The procedure was performed on an outpatient basis in 12 of the last 17 patients with the suture tension limiting technique (71%) compared to 2 of the first 13 patients without the technique (15%) (FIG. 15). Many patients did not require narcotic analgesics following discharge. Seventy-three percent of patients did not require intermittent catheterization beyond the day that their indwelling catheter was removed (FIG. 16). All patients became catheter free. The prevalence of urinary urgency was similar at the post-op and short term follow-ups at 17 and 19 percent, respective (FIG. 17). Six percent of patients complained of urgency incontinence on short term follow-up. Twenty-nine of 30 patients (97%) had cure of stress incontinence on follow-up; all 30 patients on post-op follow-up and 15 of 16 (94%) on short-term follow-up. Cure was defined as the lack of urinary leakage with activity. One woman developed urinary leakage three months following her surgery. She had the first set of G1 anchors placed and also had the suspending suture tied without the technique of tension limitation. That patient's anchors appeared to be within the pubic bone on an anterior-posterior view of the pelvis. FIG. 18 indicates the patients' satisfaction with the results of their procedure as taken from their short term questionnaire. There were no wound or bone infections.

EXAMPLE II

A group of patients are prepared in the manner described in Example I. Two separated, one inch transverse incisions are made over the pubic bone (FIG. 8) and dissection is carried down to the area of the rectus fascia. Beginning on the right side, the wound is stretched cephalad to allow the vertical passage of a suture passer of the type illustrated in FIGS. 5 and 6 through the rectus fascia with the probe tip fully exposed (FIG. 9A). Distal advancement of the suture passer is accomplished with the needle (probe) tip proximally retracted within the probe guide. The suture passer is acutely angled into the abdomen so that the point rests on the underside of the pubic periosteum (FIG. 9B).

While maintaining contact with the underside of the pubis, the suture passer with the probe tip retracted is thereafter passed distally toward the introitus. At the completion of this distal passage, the suture passer can be palpated through the introitus to the right of the urethra (FIG. 9C). The distal end tip of the suture passer is withdrawn from the surface of pubourethral ligament and gently swept along the pubocervical fascia to the area of the bladder neck (FIG. 9D) under the guidance of a finger within the vagina. Palpation through the vagina may be safely preformed to assist in localization of suture passer tip.

The probe tip is then distally extended. The suture passer is then passed through the pubocervical fascia and vaginal mucosa at point 1 (FIG. 10A). The probe is then retracted maximally to the unlocked position to allow a number 1 polypropylene suture to be manually placed into the suture channel. The probe is moved distally to lock the suture therein. The suture passer is thereafter withdrawn through the pubic wound (FIG. 10B) and the suture is released from the suture channel by manually retracting the probe.

The suture passer with the probe tip extended is then reintroduced through the rectus fascia 2 cm. lateral to the initial passage and through the vaginal mucosa at point 2 (FIG. 10C) using the same passage technique described above (FIG. 9A–D). The vaginal end of the suture is then placed into the open end of the suture channel and locked. The suture passer is then withdrawn into the retropubic space (FIG. 10D) and then advanced to point 3 where it is passed through the vaginal mucosa as with point 1 and 2 and passed out of to the introitus (FIG. 10E).

The suture is then removed from the suture passer by maximally retracting the probe tip to the "unlocked" position to align the suture channel and opening in the probe guide, and the suture passer is once again withdrawn into the retropubic space (FIG. 10F). The probe tip is then extended and the suture passer is pushed through the vaginal mucosa at point 4 (FIG. 10G). The vaginal end of the suture is then placed into the unlocked suture channel and locked into place, and pulled up through the pubic wound. An attempt is made with the 4 entry points through the pubocervical fascia to maximize 1) their separation (approximately 2 cm. apart), and 2) their lateralization from the bladder neck and urethra (approximately 2 cm. away) (FIG. 6A).

The identical procedure is performed on the left side. Direct or video cystoscopic confirmation of suture position is performed on the left side. Direct or video cystoscopic confirmation of suture position is performed with special attention to avoid handling the contaminated eyepiece of the cystoscope when video cystoscopy is done.

The Mitek G2 Anchor System (Mitek Surgical Products, Inc., Northwood, Massachusetts) is then used in all patients for pubic bone fixation of the suspensory sutures. Drill sites are located by placing a drill guide 25 illustrated in FIG. 1 over the pubic bone and extending the bone probes distally until both bone probes have made contact with the pubic bone. A 2.5 mm drill bit is advanced through the drill guide to produce two holes drilled into the pubic bone approximately 2 cm. lateral to the symphysis (FIG. 5A). One anchor for each side (2 per patient) is loaded into the drill guide channel and advanced into its hole before removing the drill guide after drilling. Traction is placed on the sutures to assure adequate fixation of the anchors.

The sutures on each side are then tied down with sufficient tension so as to develop a gentle elevation and cradle-like support of the bladder neck (FIG. 6A and 6B). Tension is regulated by tying the sutures across a suture tensioner as illustrated in FIG. 7, and thereafter removing the tensioner.

The patients are thereafter postoperatively treated as described in Example I.

EXAMPLE III

The use of a number of the above described tools will now be described as used in conjunction with a bladder neck suspension procedure. The first procedure involves suspending the bladder neck with tissue staples. The use of the staples allow the bladder neck suspension procedure to be accomplished entirely intravaginally.

The patient is first prepared by placing the pubic drape 300 as described above. The surgeon then properly locates the site at which the staple 500 is to be placed with the staple applier 502. The staple 500 is loaded into the applier 502 in between the support members 512. The applier 502 is then extended into the vagina with the handles 518 still slightly apart. Once aligned to one side of the bladder neck, the probes 512 and staple 500 are pressed through the vaginal mucosa and upward into the iliopectineal or other nearby ligament.

The handles 518 are then closed, pressing the support members 512 together and closing the staple 500 about the ligament securely. The handles 518 are then opened again, spreading the support members 512 apart. The applier 502 is then removed from the vagina and the foregoing procedure is repeated on the opposite side of the bladder neck.

In this fashion, the bladder neck suspension procedure is accomplished in a purely intravaginal procedure in which only the staple and no suture is needed. Further, there is no need for drilling, suture, anchoring, or other surgery to accomplish the procedure, thus resulting in less trauma to the patient. Lastly, since there the procedure is accomplished intravaginally, there is no scar or other visual evidence that the procedure was performed.

EXAMPLE IV

The use of a number of the above described tools will now be described as used in performing a bladder neck suspension procedure. This procedure involves using one or more sutures, the suture supports, the suture passer or the drill guide, and anchors, to suspend the bladder neck.

The patient is first prepared by installing the pubic drape 300 as was described above. Once in place, a small one inch transverse incision is made over the pubic bone. The tip 120 of the suture passer 105 is passed through the rectus fascia and then sharply angled onto the abdomen so that the point rested on the underside of the pubic periosteum. The tip 120 of the suture passer 105, while maintaining contact with the underside of the pubis, was thereafter passed distally to the pubourethral ligament and gently swept along the pubocervical fascia to the area of the bladder neck under the guidance of a finger in the vagina. The suture passer 105 is then passed through the pubocervical fascia and vaginal mucosa into the vagina.

A suture is then tied off to a suture support 450 on one end (if the end of the suture is not integrally molded onto the support 450 already), and the other end is then captured by a suture capturing device, such as in the suture channel 130 of the suture passer 105 as previously described. The suture is then withdrawn upward through the rectus fascia and out through the incision. In this manner, the suture is easily passed through the tissue of the patient with exact placement. The suture should be pulled slightly taut. At this time the suture support 450 will be pulled against the vaginal wall.

A Mitek anchor is then used to fix the suture to the bone. This is accomplished by one of the methods described above for placing the anchors.

EXAMPLE V

The procedure similar to that in Example IV is performed, except that the procedure is accomplished through the use of the "C" clamp type drill guide, the suture support, and a plug or anchor. In this procedure, the "C" clamp type drill guide 600 is positioned as described above. The "C" clamp 600 is again used to site a pathway from the pubic area to the vagina. A drill bit is passed through the bore 624 of the "C" clamp 600, penetrating the pubic bone and passing into the vagina. A suture pre-tied to a suture support 450, as described above, is passed through the passageway created up through the wound to the abdomen surface. The suture is again supported against the vaginal wall by one of the suture supports 450 described above.

The free end of the suture may then be tied off to secure it at the proper length by tying a knot in the suture sufficiently large to prevent it from pulling back through the hole, or by securing it to a plug. The plug may be used to secure the suture, the plug having the added advantage that the suture tension may then be adjustable. The plug may be a short shaft or tube member which is nearly the same size as the hole drilled. Once the suture is pulled through the bone, the plug may be inserted into the hole, pressing the suture between the bone and the plug, thus securing it tightly. If the plug does not securely station the suture, the suture may be wound around the plug one or more times and tied off in order to aid in securing the suture. If the plug is tubular, the suture is knotted at the proper length and any excess suture may be stored in the hollow area so that the suture length may be adjusted at a future date.

More than one suture may be used in conjunction with the above devices, as is believed apparent to one skilled in the art given the above disclosure.

Although this invention has been described in terms of certain preferred embodiments, other embodiments that are apparent to those of ordinary skill in the art in view of the foregoing are also within the scope of this invention. Accordingly, the scope of the invention is intended to be defined only by reference to the appended claims.

REFERENCES

[1] Pereyra, A. J.: A simplified surgical procedure for the correction of stress incontinence in women. West. J. Surg., 67:223, 1959.
[2] Stamey, T. A.: Endoscopic Suspension of the vesical neck for urinary incontinence in females: Report on 203 consecutive patients. Ann. Surg., 192:465, 1980.
[3] Raz, S.: Modified bladder neck suspension for female stress incontinence. Urology, 17:82, 1981.
[4] Leach, G. E.: Bone fixation technique for transvaginal needle suspension. Urology, 31:388, 1988.
[5] Gittes, R. F. and Loughlin, K. R.: No-incision pubovaginal suspension for stress incontinence. J. Urol. 138:568, 1987.
[6] Winter, C. C.: Peripubic urethropexy for urinary stress incontinence in women. Urology, 20:408, 1982.
[7] McKiel, C. F., Jr., Graf, E. C. and Callahan, D. H.: Marshall-Marchetti procedure: modification. J. Urol., 96:737, 1966.
Hancock, R., Brandstetter, L. H. and Hodgins, T. E.: Transpubic suspension of the bladder neck for urinary incontinence. J. Urol., 123:667, 1980.
[9] Richmond, J. C., Donaldson, W. R., Fu, F. and Harner, C. D.: Modification of the Bankart reconstruction with a suture anchor: report of a new technique. Am. J. Sports Med., 19:343, 1991.
[10] Pederson, B., Tesoro, D., Wertheimer, S. J. and Coraci, M.: Mitek anchor system: a new technique for tenodesis and ligamentous repair of the foot and ankle. J. Foot Surg., 30:48, 1991.
[11] Spencer, J. R., O'Conor, V. J. and Schaeffer, A. J.: A comparison of endoscopic suspension of the vesical neck with suprapubic vesicourethropexy for treatment of stress urinary incontinence. J. Urol., 137:411, 1987.
[12] Araki, T., Takamoto, H., Hara, T. Jujimoto, H., Yoshida, M. and Katayama, Y.: The loop loosening procedure for urination difficulties after Stamey suspension of the vesical neck. J. Urol., 144: 1990.
[13] Webster, G. D. and Kreder, K. J.: Voiding dysfunction following cystourethropexy: Its evaluation and management. J. Urol., 144:1990.

We claim:

1. A bone anchor implantation device for directing a bone anchor at a selected site, permitting introduction of the bone anchor through tissue and into a bone, comprising:
   a housing;
   a textured soft tissue restraining structure on a distally facing tissue contacting surface of the housing;
   at least one probe axially slidably connected to the housing, said probe being movable from a proximal retracted position to a distal extended position, said probe having a proximal end and a distal bone-contacting end, the distal bone-contacting end of said probe being shielded within the housing when said probe is in the retracted position, and the distal bone-contacting end of said probe being exposed outside the housing when said probe is in the extended position; and
   a guide channel having a longitudinal axis extending through the housing substantially in parallel with the longitudinal axis of said probe.

2. The bone anchor implantation device of claim 1, wherein the housing comprises an elongate generally tubular structure.

3. The bone anchor implantation device of claim 1, further comprising a generally transversely extending handle attached to the housing.

4. The bone anchor implantation device of claim 1, wherein said probe is disposed in a probe channel, the probe channel being stationary relative to the guide channel.

5. The bone anchor implantation device of claim 4, wherein the diameter of the guide channel is larger than the diameter of the probe channel.

6. The bone anchor implantation device of claim 1, further comprising means for releasably retaining said probe in the retracted position.

7. The bone anchor implantation device of claim 1, further comprising a releasable lock for releasably retaining said probe in the retracted position.

8. The bone anchor implantation device of claim 1, wherein said probe comprises an elongate solid wire.

9. The bone anchor implantation device of claim 1, further comprising means for providing a limit to distal travel of said probe.

10. The bone anchor implantation device of claim 1, further comprising a stop attached to the proximal end of said probe, said stop providing a mechanical limit to distal travel of said probe when said stop comes in contact with the housing.

11. The bone anchor implantation device of claim 1, further comprising a drill bushing extending through the guide channel.

12. The bone anchor implantation device of claim 1, wherein the guide channel has a slot extending through a wall of the guide channel and longitudinally throughout substantially the entire length of the guide channel.

13. The bone anchor implantation device of claim 1, further comprising a bone anchor installation tool removably positioned in the guide channel and a bone anchor releasably secured to the bone anchor installation tool.

14. The bone anchor implantation device of claim 1, comprising two probes.

15. The bone anchor implantation device of claim 14, wherein the guide channel is situated generally in between the two probes such that a line extending transversely between the two probes intersects at least a portion of the guide channel.

16. The bone anchor implantation device of claim 14, wherein the center line of the two probes are separated by a distance within the range of from about 5 mm to about 20 mm.

17. A method of percutaneously positioning a bone anchor implantation device over an unexposed bone, comprising the steps of:

providing a bone anchor implantation device comprising a housing, at least one axially extendable probe within the housing, the probe being extendable from a retracted position to an extended position, and a guide channel extending through the housing;

positioning the guide channel over the unexposed bone;

advancing the probe through a first tissue path until the probe contacts the unexposed bone, or until the probe reaches the extended position without contacting the unexposed bone;

if the probe does not contact the unexposed bone, retracting the probe from the extended position to the retracted position, adjusting the position of the bone anchor implantation device, and then reextending the probe through at least a second tissue path until the probe contacts the unexposed bone to assure that the guide channel is properly positioned over the unexposed bone.

18. The method of claim 17, wherein the step of positioning the guide channel over the unexposed bone comprises positioning the guide channel over a pubic bone.

19. The method of claim 17, further comprising the step of advancing a bone anchor through the guide channel to implant the bone anchor into the unexposed bone.

20. The method of claim 19, wherein the step of advancing the anchor further comprises advancing a drill bit into the bone through the guide channel of the bone anchor implantation device to provide a recess in the bone and advancing the anchor into the recess.

21. The method of claim 19, further comprising the step of selecting an anchor having a suture secured thereto.

22. A bone anchor implantation device for directing a bone anchor at a selected site, permitting introduction of the bone anchor through tissue and into a bone comprising:

a housing having a tissue contacting surface on a distal portion thereof;

at least one probe mounted to the housing;

a drill guide channel extending through the housing; and a tissue retention structure on the tissue contacting surface of the housing.

23. The bone anchor implantation device of claim 22, wherein the tissue retention structure comprises a plurality of serrations on the tissue contacting surface.

* * * * *